US012655465B2

(12) United States Patent
Jarvius et al.

(10) Patent No.: US 12,655,465 B2
(45) Date of Patent: Jun. 16, 2026

(54) SYSTEM FOR DETECTING AND CHARACTERIZING A MICROORGANISM

(71) Applicant: Q-Linea AB, Uppsala (SE)

(72) Inventors: Jonas Jarvius, Uppsala (SE); Anders Lind, Tarnsjo (SE); Henrik Soderstrom, Knivsta (SE); Jan Grawe, Uppsala (SE)

(73) Assignee: Q-LINEA AB, Uppsala (SE)

( * ) Notice: Subject to any disclaimer, the term of this patent is extended or adjusted under 35 U.S.C. 154(b) by 179 days.

(21) Appl. No.: 18/385,099

(22) Filed: Oct. 30, 2023

(65) Prior Publication Data

US 2024/0368670 A1 Nov. 7, 2024

Related U.S. Application Data

(62) Division of application No. 16/094,699, filed as application No. PCT/EP2017/059542 on Apr. 21, 2017, now Pat. No. 11,845,978.

(30) Foreign Application Priority Data

Apr. 21, 2016 (GB) ...................................... 1606991
Apr. 21, 2016 (WO) ................. PCT/EP2016/058952
Oct. 13, 2016 (GB) ...................................... 1617353

(51) Int. Cl.

| | |
|---|---|
| *C12Q 1/6806* | (2018.01) |
| *A01N 1/142* | (2025.01) |
| *A01N 1/148* | (2025.01) |
| *C12Q 1/6837* | (2018.01) |
| *C12Q 1/686* | (2018.01) |

(52) U.S. Cl.
CPC ........... *C12Q 1/6806* (2013.01); *A01N 1/142* (2025.01); *A01N 1/148* (2025.01); *C12Q 1/6837* (2013.01); *C12Q 1/686* (2013.01)

(58) Field of Classification Search
None
See application file for complete search history.

(56) References Cited

U.S. PATENT DOCUMENTS

| | | |
|---|---|---|
| 3,159,384 A | 12/1964 | Davis |
| 3,764,780 A | 10/1973 | Ellis |
| 3,975,001 A | 8/1976 | Moore et al. |
| 4,004,883 A | 1/1977 | Meyer et al. |
| 4,523,078 A | 6/1985 | Lehmann |
| 4,629,686 A | 12/1986 | Gruenberg |
| 4,652,517 A | 3/1987 | Scholl et al. |
| 4,666,850 A | 5/1987 | Mehl et al. |
| 4,851,330 A | 7/1989 | Kohne |
| 4,886,071 A | 12/1989 | Mehl et al. |
| 5,052,812 A | 10/1991 | Tannenbaum et al. |
| 5,143,854 A | 9/1992 | Pirrung et al. |
| 5,183,994 A | 2/1993 | Bowles, Sr. et al. |
| 5,217,876 A | 6/1993 | Turner et al. |
| 5,238,302 A | 8/1993 | Rohan |
| 5,316,146 A | 5/1994 | Graff |
| 5,378,633 A | 1/1995 | von Behrens et al. |
| 5,405,783 A | 4/1995 | Pirrung et al. |
| 5,445,934 A | 8/1995 | Fodor et al. |
| 5,510,267 A | 4/1996 | Marshall |
| 5,577,837 A | 11/1996 | Martin et al. |
| 5,744,305 A | 4/1998 | Fodor et al. |
| 5,770,394 A | 6/1998 | Berndt |
| 5,789,173 A | 8/1998 | Peck et al. |
| 5,817,508 A | 10/1998 | Berndt |
| 5,882,918 A | 3/1999 | Goffe |
| 5,945,334 A | 8/1999 | Besemer et al. |
| 5,994,066 A | 11/1999 | Bergeron et al. |
| 6,028,293 A | 2/2000 | Nagle et al. |
| 6,059,446 A | 5/2000 | Dschida |

(Continued)

FOREIGN PATENT DOCUMENTS

| | | |
|---|---|---|
| CN | 2436459 Y | 6/2001 |
| CN | 101130808 A | 2/2008 |

(Continued)

OTHER PUBLICATIONS

Brown, Deborah A. et al., "Sorting of GPI-Anchored Proteins to Glycolipid-Enriched Membrane Subdomains During Transport to the Apical Cell Surface," Cell, vol. 68 (1992) pp. 533-544.

(Continued)

*Primary Examiner* — Carla J Myers

(74) *Attorney, Agent, or Firm* — Lippes Mathias LLP

(57) ABSTRACT

A clinical sample testing system includes a portable apparatus for transport and incubation of a clinical sample in a culture vessel. The apparatus includes a sealable container having a thermally insulated compartment for receiving the vessel and a heater for heating the clinical sample to a temperature suitable for pre-culturing it. The system further includes a microorganism detection device which receives the vessel and cultures the clinical sample. The device includes a) a test aliquot extraction device for removing a test aliquot from the vessel and/or from a second culture vessel sampled therefrom, and a DNA testing device for separating DNA from the test aliquot and performing nucleic acid tests on the DNA to identify the microorganism and detecting genetic antimicrobial resistance markers therein and/or b) an antimicrobial susceptibility test device for performing an antimicrobial susceptibility test on the cultured clinical sample or portion thereof by monitoring microbial growth.

20 Claims, 12 Drawing Sheets

(56) References Cited

U.S. PATENT DOCUMENTS

| | | | |
|---|---|---|---|
| 6,060,266 A | 5/2000 | Naqui et al. | |
| 6,083,763 A | 7/2000 | Balch | |
| 6,093,551 A | 7/2000 | Raithel et al. | |
| 6,096,532 A | 8/2000 | Armstrong et al. | |
| 6,143,495 A | 11/2000 | Lizardi et al. | |
| 6,183,960 B1 | 2/2001 | Lizardi | |
| 6,225,625 B1 | 5/2001 | Pirrung et al. | |
| 6,235,472 B1 | 5/2001 | Landgren et al. | |
| 6,255,467 B1 | 7/2001 | Lindner et al. | |
| 6,261,776 B1 | 7/2001 | Pirrung et al. | |
| 6,291,183 B1 | 9/2001 | Pirrung et al. | |
| 6,310,189 B1 | 10/2001 | Fodor et al. | |
| 6,329,143 B1 | 12/2001 | Stryer et al. | |
| 6,403,957 B1 | 6/2002 | Fodor et al. | |
| 6,406,844 B1 | 6/2002 | Pirrung et al. | |
| 6,465,201 B1 | 10/2002 | Presente et al. | |
| 6,465,448 B1 | 10/2002 | Gerson et al. | |
| 6,630,308 B2 | 10/2003 | Stryer et al. | |
| 6,646,243 B2 | 11/2003 | Pirrung et al. | |
| 6,660,234 B2 | 12/2003 | Stryer et al. | |
| 6,747,143 B2 | 6/2004 | Stryer et al. | |
| 6,803,208 B2 | 10/2004 | Seaver et al. | |
| 7,008,788 B2 | 3/2006 | Schremp et al. | |
| 7,087,732 B2 | 8/2006 | Fodor et al. | |
| 7,223,363 B2 | 5/2007 | McNeely et al. | |
| 7,235,400 B2 | 6/2007 | Adey | |
| 7,334,516 B2 | 2/2008 | Ho et al. | |
| 7,341,841 B2 | 3/2008 | Metzger et al. | |
| 7,387,883 B2 | 6/2008 | Walsh et al. | |
| 7,547,526 B2 | 6/2009 | Ladisch et al. | |
| 7,687,239 B2 | 3/2010 | Goldberg et al. | |
| 7,790,388 B2 | 9/2010 | Landegren et al. | |
| 7,893,251 B2 | 2/2011 | Lorenz | |
| 8,071,319 B2 | 12/2011 | Metzger et al. | |
| 8,074,465 B2 | 12/2011 | Heroux et al. | |
| 8,288,522 B2 | 10/2012 | Luo et al. | |
| 8,460,887 B2 | 6/2013 | Goldberg et al. | |
| 8,481,265 B2 | 7/2013 | Peytavi et al. | |
| 8,603,769 B2 | 12/2013 | Feng et al. | |
| 8,609,024 B2 | 12/2013 | Ronsick et al. | |
| 8,652,800 B2 | 2/2014 | Walsh et al. | |
| 8,709,344 B2 | 4/2014 | Bishop et al. | |
| 8,709,748 B2 | 4/2014 | Walsh et al. | |
| 8,780,181 B2 | 7/2014 | Olesen et al. | |
| 8,841,118 B2 | 9/2014 | Robinson et al. | |
| 8,846,897 B2 | 9/2014 | Euting et al. | |
| 8,895,255 B1 | 11/2014 | Goldberg et al. | |
| 8,911,987 B2 | 12/2014 | Robinson et al. | |
| 8,937,174 B2 | 1/2015 | Rothmann et al. | |
| 9,310,291 B2 | 4/2016 | Schulz et al. | |
| 10,995,311 B2 * | 5/2021 | Jarvius | C12M 41/24 |
| 2001/0007742 A1 | 7/2001 | Landegren | |
| 2002/0055101 A1 | 5/2002 | Bergeron et al. | |
| 2003/0098271 A1 | 5/2003 | Somack et al. | |
| 2003/0143580 A1 | 7/2003 | Straus | |
| 2003/0235853 A1 | 12/2003 | Stryer et al. | |
| 2004/0121313 A1 | 6/2004 | Ecker et al. | |
| 2004/0121335 A1 | 6/2004 | Ecker et al. | |
| 2004/0229268 A1 | 11/2004 | Hogan et al. | |
| 2005/0037408 A1 | 2/2005 | Christensen et al. | |
| 2005/0042144 A1 | 2/2005 | Hubbard | |
| 2005/0048599 A1 | 3/2005 | Goldberg et al. | |
| 2005/0064469 A1 | 3/2005 | Schulz et al. | |
| 2005/0095665 A1 | 5/2005 | Williams et al. | |
| 2005/0148027 A1 | 7/2005 | Pirrung et al. | |
| 2005/0202487 A1 | 9/2005 | Klepp et al. | |
| 2005/0214828 A1 | 9/2005 | Pirrung et al. | |
| 2005/0244918 A1 | 11/2005 | Walsh et al. | |
| 2005/0244943 A1 | 11/2005 | Ladisch et al. | |
| 2006/0020579 A1 | 1/2006 | Freedman et al. | |
| 2006/0029972 A1 | 2/2006 | Lorenz | |
| 2006/0094034 A1 | 5/2006 | Brousseau et al. | |
| 2006/0127924 A1 | 6/2006 | Hellyer et al. | |
| 2006/0223098 A1 | 10/2006 | Lane et al. | |
| 2008/0029247 A1 | 2/2008 | Nozaki et al. | |
| 2008/0139865 A1 | 6/2008 | Galliher et al. | |
| 2008/0145919 A1 | 6/2008 | Franklin et al. | |
| 2008/0160528 A1 | 7/2008 | Lorenz | |
| 2008/0286757 A1 | 11/2008 | Gaisford et al. | |
| 2009/0148829 A1 | 6/2009 | Ecker et al. | |
| 2009/0209031 A1 | 8/2009 | Stopek | |
| 2010/0112549 A1 | 5/2010 | Rey et al. | |
| 2010/0124763 A1 | 5/2010 | Walsh et al. | |
| 2010/0129814 A1 | 5/2010 | Walsh et al. | |
| 2010/0129858 A1 | 5/2010 | Walsh et al. | |
| 2010/0184210 A1 | 7/2010 | Rossmanith et al. | |
| 2010/0255474 A1 | 10/2010 | Russwurm et al. | |
| 2010/0288060 A1 | 11/2010 | Ronsick et al. | |
| 2010/0291615 A1 | 11/2010 | Ronsick et al. | |
| 2010/0291618 A1 | 11/2010 | Robinson et al. | |
| 2010/0291619 A1 | 11/2010 | Robinson et al. | |
| 2010/0291669 A1 | 11/2010 | Robinson et al. | |
| 2010/0297645 A1 | 11/2010 | Pierik et al. | |
| 2010/0311108 A1 | 12/2010 | Bishop et al. | |
| 2011/0092691 A1 | 4/2011 | Euting et al. | |
| 2011/0124028 A1 | 5/2011 | Robinson et al. | |
| 2011/0124029 A1 | 5/2011 | Remes et al. | |
| 2011/0124030 A1 | 5/2011 | Philipak et al. | |
| 2011/0124038 A1 | 5/2011 | Bishop et al. | |
| 2011/0124096 A1 | 5/2011 | Philipak et al. | |
| 2011/0125314 A1 | 5/2011 | Robinson et al. | |
| 2011/0269130 A1 | 11/2011 | Shi et al. | |
| 2011/0281754 A1 | 11/2011 | Fischer et al. | |
| 2011/0294128 A1 | 12/2011 | Peytavi et al. | |
| 2012/0009577 A1 | 1/2012 | Luo et al. | |
| 2012/0070823 A1 | 3/2012 | Rothmann | |
| 2012/0077206 A1 | 3/2012 | Metzger et al. | |
| 2012/0115183 A1 | 5/2012 | Clay | |
| 2012/0149599 A1 | 6/2012 | Williams et al. | |
| 2012/0231446 A1 | 9/2012 | Heckel et al. | |
| 2013/0011905 A1 | 1/2013 | Rapoport et al. | |
| 2013/0045532 A1 | 2/2013 | Hyman et al. | |
| 2013/0065223 A1 | 3/2013 | Klein et al. | |
| 2013/0071615 A1 | 3/2013 | Murata et al. | |
| 2013/0171615 A1 | 7/2013 | Van Meerbergen et al. | |
| 2013/0183717 A1 | 7/2013 | Marble et al. | |
| 2013/0184446 A1 | 7/2013 | Marble et al. | |
| 2013/0190196 A1 | 7/2013 | Onderdonk et al. | |
| 2013/0217063 A1 | 8/2013 | Metzger et al. | |
| 2013/0224729 A1 | 8/2013 | Church et al. | |
| 2013/0226032 A1 | 8/2013 | Mitsuhashi et al. | |
| 2013/0252271 A1 | 9/2013 | Ullery | |
| 2013/0261196 A1 | 10/2013 | Diamond et al. | |
| 2014/0072998 A1 | 3/2014 | Ronsick et al. | |
| 2014/0087361 A1 | 3/2014 | Dobbelaer et al. | |
| 2014/0186832 A1 | 7/2014 | Fuchs et al. | |
| 2014/0278136 A1 | 9/2014 | Shamsheyeva et al. | |
| 2014/0287408 A1 | 9/2014 | Su et al. | |
| 2014/0323340 A1 | 10/2014 | Goldberg et al. | |
| 2015/0031074 A1 | 1/2015 | Robinson et al. | |
| 2015/0132793 A1 | 5/2015 | Penterman et al. | |
| 2015/0225762 A1 | 8/2015 | Metzger et al. | |
| 2015/0344973 A1 | 12/2015 | Rolfe et al. | |
| 2016/0010138 A1 | 1/2016 | Shamsheyeva | |
| 2016/0053219 A1 | 2/2016 | Walker et al. | |
| 2016/0257991 A1 | 9/2016 | Jarvius | |
| 2016/0281130 A1 | 9/2016 | Dahl et al. | |
| 2016/0304827 A1 * | 10/2016 | Parikh | C12M 33/00 |
| 2016/0376642 A1 | 12/2016 | Landegren et al. | |
| 2017/0121759 A1 | 5/2017 | Jarvius et al. | |
| 2017/0127665 A1 | 5/2017 | Jaffal | |
| 2017/0152510 A1 | 6/2017 | Lorenz | |
| 2017/0320054 A1 | 11/2017 | Crum et al. | |
| 2018/0127703 A1 | 5/2018 | Jarvius et al. | |
| 2018/0223327 A1 | 8/2018 | Jarvius et al. | |
| 2020/0318164 A1 | 10/2020 | Jarvius | |

FOREIGN PATENT DOCUMENTS

| | | | |
|---|---|---|---|
| CN | 101745440 A | 6/2010 | |
| CN | 101845390 A | 9/2010 | |
| CN | 204255722 U | 4/2015 | |
| EP | 0122581 A2 | 10/1984 | |
| EP | 0745849 A2 | 12/1996 | |

(56)                    References Cited

FOREIGN PATENT DOCUMENTS

| EP | 0964704 A1 | 12/1999 |
|----|-----------|---------|
| EP | 1527172 A1 | 5/2005 |
| EP | 1945821 A1 | 7/2008 |
| EP | 2942394 A1 | 11/2015 |
| JP | H08285839 A | 11/1996 |
| JP | 2001-103981 A | 4/2001 |
| JP | 2001-169778 A | 6/2001 |
| JP | 2013-255445 A | 12/2013 |
| RU | 2228735 C2 | 1/2004 |
| WO | WO 1988/006189 A1 | 8/1988 |
| WO | WO 2000/036142 A1 | 6/2000 |
| WO | WO 2000/72970 A1 | 12/2000 |
| WO | WO 2003/097831 A1 | 11/2003 |
| WO | WO 2016/170086 A1 | 10/2016 |
| WO | WO 2016/207065 A1 | 12/2016 |

OTHER PUBLICATIONS

Chandler, Darrell P. et al., "Integrated Amplification Microarrays for Infectious Disease Diagnostics," Microarrays, 1 (2012) pp. 107-124.

Dahl, Fredrik et al., "Circle-to-Circle Amplification for Precise and Sensitive DNA Analysis," PNAS, vol. 101, No. 13 (2004) pp. 4548-4553.

De Jong, Ymke, "A Fast Antibiotic Susceptibility Test by Direct Staining," Uppsala Universitet, Thesis Report (2014) pp. 1-23.

Fire, Andrew et al., "Rolling Replication of Short DNA Circles," Proc. Natl. Acad. Sci. USA, vol. 92 (1995) pp. 4641-4645.

Fredborg, Marlene et al., "Real-Time Optical Antimicrobial Susceptibility Testing," Journal of Clinical Microbiology, vol. 51, No. 7 (2013) pp. 2047-2053.

GE Healthcare Lifesciences Handbook, "Nucleic Acid Sample Preparation for Downstream Analyses" (2013) 168 pages.

Giacomazzi, C. G., et al., "Rapid diagnosis of tuberculosis and multidrug resistance with the microscopic observation drug susceptibility assay in Ecuador." Int. J. Tuberc. Lung Dis., vol. 14, No. 6, pp. 786-788 (2010).

Göransson et al., "Rapid Identification of Bio-Molecules Applied for Detection of Biosecurity Agents Using Rolling Circle Amplification," Plos One, vol. 7, No. 2, (2012), pp. 1-9.

Gyarmati, Peter, et al., "Simultaneous Genotyping of All Hemagglutinin and Neuraminidase Subtypes of Avian Influenza Viruses By Use of Padlock Probes," Journal of Clinical Microbiology, vol. 46, No. 5 (2008) pp. 1747-1751.

Handschur, M. Karlic, et al., "Preanalytic Removal of Human DNA Eliminates False Signals in General 16S rDNA PCR Monitoring of Bacterial Pathogens in Blood," Comp. Immun. Microbiol. Infect. Dis., vol. 32 (2009) pp. 207-219.

Hardenbol, Paul, et al., "Multiplexed Genotyping With Sequence-Tagged Molecular Inversion Probes," Nature Biotechnology, vol. 21, No. 6 (2003) pp. 673-678.

Harrison, Susan T. L., "Bacterial Cell Disruption: A Key Unit Operation in the Recovery of Intracellular Products," Biotech. Adv., vol. 9 (1991) pp. 217-240.

Hu, Wenqi, et al., "Application of Nucleic Acid Hybridization Technology in Detection of Environmental Microorganism," Microbiology China, vol. No. 22, Issue No. 6, Dec. 31, 1995 (w/English Translation) 15 pages.

Ishii, Reina et al., "Counting Single DNA Molecule by On-Bead Rolling Circle Amplification for Quantitative Analyses," 15th International Conference on Miniaturized Systems for Chemistry and Life Sciences (2011) pp. 70-72.

Ichiyama, Satoshi et al. "*Mycobacterium* Growth Indicator Tube Testing in Conjunction with the AccuProbe or the AMPLICOR-PCR Assay for Detecting and Identifying Mycobacteria from Sputum Samples," J. Clin. Microbial., vol. 35, No. 8, Aug. 1997, pp. 2022-2025.

Ichiyama, Satoshi, "A Protocol for the Rapid Diagnosis of Pulmonary Tuberculosis," Medical Technology, 2000, vol. 28, No. 12, pp. 1324-1329 (with English Translation).

Jarvius, Jonas et al., "Digital Quantification Using Amplified Single-Molecule Detection," Nature Methods, vol. 3, No. 9 (2006) pp. 725-727 (with Supplementary note—16 pages).

Jorgensen et al., "Antimicrobial Susceptibility Testing: A Review of General Principles and Contemporary Practices," Clinical Infectious Diseases, vol. 49, No. 11 (2009), pp. 1749-1755.

Kagan, Robert L., et al., "Rapid Automated Diagnosis of Bacteremia by Impedance Detection," Journal of Clinical Microbiology, vol. 5, No. 1 (1977) pp. 51-57.

Ke, Rongqin, et al., "Colorimetric Nucleic Acid Testing Assay for RNA Virus Detection Based on Circle-To-Circle Amplification of Padlock Probes," Journal of Clinical Microbiology, vol. 49, No. 12 (2011) pp. 4279-4285.

Kesberg, Anna Isabella, et al., "Improved Protocol For Recovery of Bacterial DNA From Water Filters: Sonication and Backflushing of Commercial Syringe Filters," Journal of Microbiological Methods, 93, 2 (2013) pp. 1-7.

Kiran, S, et al., "Synthesis and studies of Nanoporous TiO2 using Self Designed low cost Magnetic Stirrer with Hot Plate," Int'l J. of Advanced Information Science and Technology (IJAIST), vol. 31, No. 31 (2014), pp. 112-114.

Koltai, Hinanit, et al., "Survey and Summary—Specificity of DNA Microarray Hybridization: Characterization, Effectors and Approaches for Data Correction," Nucleic Acids Research, vol. 36, No. 7 (2008) pp. 2395-2405.

Kumar MD, Anand, et al., "Duration of Hypotension Before Initiation of Effective Antimicrobial Therapy is the Critical Determinant of Survival in Human Septic Shock," Critical Care Medicine, vol. 34, No. 6 (2006) pp. 1589-1596.

Lahanas, Sophie, et al., "Evaluation of the Alfred 60/AST as a Screening Test for Urinary Tract Infections," Journal of Clinical Microbiology (2013) pp. 1-13.

Landegren, Ulf et al., "A Ligase-Mediated Gene Detection Technique," Science, vol. 241 (1988) pp. 1077-1080.

Larsson, Chatarina et al., "In Situ Genotyping Individual DNA Molecules by Target-Primed Rolling-Circle Amplification of Padlock Probes," Nature Methods, vol. 1, No. 3 (2004) pp. 227-232.

Liesenfeld, O. et al., "Molecular Diagnosis of Sepsis: New Aspects and Recent Developments," European Journal of Microbiology and Immunology, 4, 1 (2014) pp. 1-25.

Liu, Quanjun et al., "Microarray-In-A-Tube for Detection of Multiple Viruses," Clinical Chemistry, 53:2 (2007) pp. 188-194.

Lizardi, Paul M. et al., "Mutation Detection and Single-Molecule Counting Using Isothermal Rolling-Circle Amplification," Nature Genetics, vol. 19 (1998) pp. 225-232.

Loonen, Anne J. M. et al. "Comparison of Pathogen DNA Isolation Methods From Large Volume of Whole Blood to Improve Molecular Diagnosis of Bloodstream Infections," PLOS One, vol. 8, Issue 8 (2013) pp. 1-7.

Lorenz, Michael, "SelectNA Plus—Walk-Away Automated Extraction of Microbial DNA From Clinical Samples," Molzym GmbH & Co. KG, Molzym's Tapas Symposium Direct Molecular Testing (2014) pp. 1-6.

Metzger, S. et al., "Direct Identification of Methicillin Resistant *Staphylococcus aureus* (MRSA) Using Small Numbers of Immobilized Cells and Response to Oxacillin (OXA) by Automated Growth Analysis," ASM, Accelr8 Technology Corporation (2007), 1 page.

Metzger, S. et al., "Rapid Identification of Resistance Phenotypes in Gram-Negative Bacilli Using Automated Digital Microscopy," ASM, Accelr8 Technology Corporation (2009), 1 page.

Metzger, S. et al., "Same-Day ID and Resistance Phenotyping Directly From Respiratory Specimens by Automated Microscopy," ASM, Accelr8 Technology Corporation (2011), 1 page.

Metzger, S. et al., "Rapid Simultaneous Identification and Quantitation of *Staphylococcus aureus* and Pseudomonas Aeruginosa Directly From Bronchoalveolar Lavage Specimens Using Automated Microscopy," Diagnostic Microbiology and Infectious Disease, 79 (2014) pp. 160-165.

(56) References Cited

OTHER PUBLICATIONS

Mezger, MSc, Anja et al., "Rapid Antibiotic Susceptibility Testing for Urinary Tract Infections," Uppsala Universitet, Science for Life Laboratory, 1 page, at least as early as Jun. 13, 2014.

Mitteregger et al., "Neutralization of Antimicrobial Substances in New BacT/Alert FA and FN Plus Blood Culture Bottles". Journal of Clinical Microbiology; 2013; 51: pp. 1534-1540. (Year: 2013).

Mothershed, Elizabeth A. et al., "Nucleic Acid-Based Methods for the Detection of Bacterial Pathogens: Present and Future Considerations for the Clinical Laboratory," Clinica Chimica Acta, 363 (2006) pp. 206-220.

Nilsson, Mats et al., "Padlock Probes: Circularizing Oligonucleotides for Localized DNA Detection," Science, vol. 265 (1994) pp. 2085-2088.

Olson, Walter C. et al., "Shipping Blood to a Central Laboratory in Multicenter Clinical Trials: Effect of Ambient Temperature on Specimen Temperature, and Effects of Temperature on Mononuclear Cell Yield, Viability and Immunologic Function," Journal of Translation Medicine, 2011, 9:26 (https://www.ncbi.nlm.nih.gov/pmc/articles/PMC3063218/pdf/1479-5876-9-26.pdf).

Pezzlo, M. T. et al., "High Recovery of Bacteria and Fungi in Low Concentrations From Liquid Samples," Pocared Diagnostics 2064, 7 pages, at least as early as Jun. 13, 2014.

Prere, M.-F. et al., "Rapid Identification of Bacteria, mecA and Van Genes From Blood Cultures," Pathologie Biologie 55 (2007) pp. 375-377.

Price et al., "Rapid Antibiotic Susceptibility Phenotypic Characterization of Staphylococcus aureus Using Automated Microscopy of Small Numbers of Cells," Journal of Microbiological Methods, 98 (2014) pp. 50-58.

Pulido et al., "Progress on the development of rapid methods for antimicrobial susceptibility testing," J. Antimicrob .Chemother; 2013; 68: 2710-2717. (Year: 2013).

Rajagopal, Soumitra et al., "Eight Gram-Negative Bacteria are 10 000 Times More Sensitive to Cationic Detergents Than to Anionic Detergents," Can. J. Microbiol. 49 (2003) pp. 775-779.

Ru, Na-dan et al., "Rapid Identification and Susceptibility Testing of Positive Blood Culture Cause by Gram Negative Bacteria," Chinese Journal of Microecology, vol. 24, No. 11 (Nov. 2012), pp. 1024-1026.

Sage, Jr., Burton H. et al., "Rapid Visual Detection of Microorganisms in Blood Culture," Journal of Clinical Microbiology, vol. 20, No. 1 (1984) pp. 5-8.

Sartor, Maureen et al., "Microarray Results Improve Significantly as Hybridization Approaches Equilibrium," BioTechniques, vol. 36, No. 5 (2004) pp. 790-796.

Sato, Kae et al., "Microbead-Based Rolling Circle Amplification in a Microchip for Sensitive DNA Detection," The Royal Society of Chemistry, Lab Chip, vol. 10 (2010) pp. 1262-1266.

Schweitzer, Barry et al., "Multiplexed Protein Profiling on Microarrays by Rolling-Circle Amplification," Nat Biotechnol., 20, 4 (2002) pp. 1-17.

Siemens, "MicroScan Dried Conventional Gram Negative Panels," Siemens Healthcare Diagnostics (2012) 4 pages.

Smith, James H. et al., "Detection of Nucleic Acid Targets Using Ramified Rolling Circle DNA Amplification: A Single Nucleotide Polymorphism Assay Model," PLOS One, vol. 8, Issue 5 (2013) pp. 1-8.

Smith, John A., et al., "Comparison of BACTEC 9420 and BacT/Alert Blood Culture Systems in an Adult Hospital," J Clinical Microbiology, vol. 33, No. 7 (Jul. 1995), pp. 1905-1908.

Spezzotti, Gianpiero, "Technical Notes on the Correct Configuration of the Alfred 60/AST Device for the Detection of Urinary Tract Infections," Journal of Clinical Microbiology, vol. 52, No. 5 (2014) pp. 1805-1806.

Sullivan, Nadine M. et al., "Practical Aerobic Membrane Filtration Blood Culture Technique: Development of Procedure," Journal of Clinical Microbiology, vol. 1, No. 1 (1975) pp. 30-36.

Sullivan, Nadine M. et al., "Practical Aerobic Membrane Filtration Blood Culture Technique: Clinical Blood Culture Trial," Journal of Clinical Microbiology, vol. 1, No. 1 (1975) pp. 37-43.

Tenover, Fred C. et al., "Vancomycin-Resistant Staphylococcus aureus Isolate From a Patient in Pennsylvania," Antimicrobial Agents and Chemotherapy, vol. 8, No. 1 (2004) pp. 275-280.

Torio, Celeste M. et al., "National Inpatient Hospital Costs: The Most Expensive Conditions by Payer, 2011," Agency for Healthcare Research and Quality, Rockville, MD, HCUP Statistical Brief #160 (2013) 12 pages.

Unico Catalog, Laboratory/MedicalNeterinary Equipment; 2012: p. 1-39. (Retrieved from internet: Accessorieshttps:// assets.tequipnnent. net/assets/1/7/UNICO-Lab-Equipment-Catalog.pdf, retrieved on Nov. 6, 2020). (Year: 2012).

Van Belkum, Alex, et al., "Next-Generation Antimicrobial Susceptibility Testing," Journal of Clinical Microbiology, vol. 51, No. 7 (2013) pp. 2018-2024.

Wei, Cheng-Wey et al., "Using a Microfluidic Device for 1 ul DNA Microarray Hybridization in 500 s," Nucleic Acids Research, vol. 33, No. 8 (2005) pp. 1-11.

Whittier, S. et al., "Evaluation of the BD Phoenix Automated Microbiology System for Antibiotic Susceptibility Testing of Streptococcus pneumoniae," American Society for Microbiology 106th General Meeting (2006) 4 pages.

Wiles, T. et al., "Rapid Antimicrobial Susceptibility Testing in Phoenix," American Society for Microbiology 99th General Meeting (1999) 3 pages.

Wu, S.-J. et al., "Preparation of Milk Samples for PCR Analysis Using a Rapid Filtration Technique," Journal of Applied Microbiology, 96 (2004) pp. 1342-1346.

Zierdt, Charles H. et al., "Development of a Lysis-Filtration Blood Culture Technique," Journal of Clinical Microbiology, vol. 5, No. 1 (1977) pp. 46-50.

Zierdt, Charles H., "Blood Lysing Solution Nontoxic to Pathogenic Bacteria," Journal of Clinical Microbiology, vol. 15, No. 1 (1982) pp. 172-174.

Zierdt, Charles H. et al., "Lysis-Filtration Blood Culture Versus Conventional Blood Culture in a Bacteremic Rabbit Model," Journal of Clinical Microbiology, vol. 15, No. 1 (1982) pp. 74-77.

Zierdt, Charles H., "Simplified Lysed-Blood Culture Technique," Journal of Clinical Microbiology, vol. 23, No. 3 (1986) pp. 452-455.

International Search Report and Written Opinion of International Application No. PCT/EP2016/058952 dated Aug. 24, 2016, 11 pages.

International Search Report and Written Opinion of International Application No. PCT/EP2017/059542 dated Jul. 17, 2017, 13 pages.

U.K. Search Report of British Application No. GB1507026.1 dated Oct. 27, 2014, 4 pages.

U.K. Search Report of British Application No. GB1606991.6 dated Jan. 26, 2017, 4 pages.

U.K. Search Report of British Application No. GB1617353.6 dated Jan. 31, 2018, 7 pages.

AliFax SRL, "Alfred 60^{AST}—First Automated System for Bacterial Culture and Susceptibility Testing", Alifax SRL, Italy (2015) 2 pages.

Anderson, Rolfe C. et al., "A Miniature Integrated Device for Automated Multistep Genetic Assays", Nucleic Acids Research, vol. 28, No. 12 (2000) pp. i-vi.

Antson, D.-O. et al., "PCR-Generated Padlock Probes Detect Single Nucleotide Variation in Genomic DNA", Nucleic Acids Research, vol. 28, No. 12 (2000) pp. i-vi.

Baker, Zelma et al., "The Bactericidal Action of Synthetic Detergents", Walter G. Zoller Memorial Dental Clinic, the Department of Bacteriology and Parasitology, and the Department of Medicine, The University of Chicago (1941) pp. 611-620.

Baner, Johan et al., "Signal Amplification of Padlock Probes by Rolling Circle Replication", Nucleic Acids Reasearch, vol. 26, No. 22 (1998) pp. 5073-5078.

Baner, Johan et al., "Parallel Gene Analysis With Allele-Specific Padlock Probes and Tag Microarrays", Nucleic Acids Research, vol. 31, No. 17 (2003) pp. 1-7.

Baner, Johan et al., "Microarray-Based Molecular Detection of Foot-And-Mouth Disease, Vesicular Stomatitis and Swine Vesicular

(56)          References Cited

OTHER PUBLICATIONS

Disease Viruses, Using Padlock Probes", Journal of Virological Methods, 143 (2007) pp. 200-206.

Barisic, Ivan et al., "Multiplex Detection of Antibiotic Resistance Genes Using Padlock Probes", Diagnostic Microbiology and Infectious Disease, 77 (2013) pp. 118-125.

BD Diagnostics, "BD Phoenix, Automated Microbiology System" (2008) 13 pages.

BD Diagnostics, "BD Phoenix ID/AST Manual Panel Inoculation" (2012) 1 page.

BD Phoenix, Laboratory Procedure, pp. 1-30, at least as early as Jun. 13, 2014.

BioMerieux SA, "Vitek 2 Instrument User Manual" (2008) 218 pages.

Birnboim, H. C. et al., "A Rapid Alkaline Extraction Procedure for Screening Recombinant Plasmid DNA", Nucleic Acids Research, vol. 7, No. 6 (1979) pp. 1513-1524.

Broeren, M. A. C. et al., "Antimicrobial Susceptibility Testing in 90 Min by Bacteria Cell Count Monitoring", Clinical Microbiology and Infection, vol. 19, No. 3 (2013) pp. 286-291.

Brookes, Mark et al., "Policy for the Transport of Pathology Samples", Pathology—Transport of Pathology Samples GP/MP6, Version 3.4, Aug. 2014, pp. 1-11.

U.S. Appl. No. 61/979,319, filed Apr. 14, 2014, Jarvius, et al.

Westh, et al., "Multiplex real-time PCR and blood culture for identification of Blood stream pathogens in patients with suspected sepsis" Clin. Microbiol. Infect., 15: 544-551 (2009).

Spaargaren, et al., "Effectiveness of Resins in Neutralising Antibiotic Activities in Bactec Plus Aerobic/F Culture Medium" American Society for Microbiology, Journal of Clinical Microbiology; vol. 36; Issue 12: 3731-3733 (1998).

* cited by examiner

SYSTEM FOR DETECTING AND CHARACTERIZING A MICROORGANISM

CROSS-REFERENCE TO RELATED APPLICATIONS

This application claims the benefit, as a Divisional, of U.S. application Ser. No. 16/094,699, filed Oct. 18, 2018, which is the National Stage of International Application PCT/EP2017/059542, filed Apr. 21, 2017, which claims the benefit of GB Application 1606991.6, filed Apr. 21, 2016, International Application PCT/EP2016/058952, filed Apr. 21, 2016, and GB Application 1617353.6, filed Oct. 13, 2016, the disclosures of each of which are incorporated herein by reference in their entireties.

BACKGROUND

The present invention relates to a method and a system for the identification of a pathological microorganism and a determination of its antimicrobial susceptibility profile.

Microbial infections represent a major class of human and animal disease with significant clinical and economic implications. Whilst various classes and types of antimicrobial agents are available to treat and/or prevent microbial infections, antimicrobial resistance is a large and growing problem in modern medicine. The numbers of antimicrobial-resistant strains of various microbial pathogens have proliferated in the past 20 years, and microorganisms continue to develop resistance to a growing number of antimicrobial, particularly antibiotic, classes. With the spread of resistance mechanisms to more organisms, the public health impact and costs associated with antimicrobial resistance are projected to increase rapidly in the years to come. In the context of treatment of a microbial infection, it can therefore be desirable, and indeed important, to have information regarding the nature of the infecting microorganism and its antimicrobial susceptibility profile in order both to ensure effective treatment and also to reduce the use of unnecessary or ineffective antibiotics and thereby to help control the spread of antibiotic, or more generally antimicrobial, resistance. This is particularly so in the case of serious or life-threatening infections in which rapid effective treatment is vital.

Sepsis, a potentially fatal whole-body inflammation caused by severe infection is the most expensive condition and driver of hospital costs in the US, comprising 5% of the total national hospital cost. Mortality increases 7% for every hour for severe sepsis, if not treated properly, and the rising prevalence of antimicrobial-resistant sepsis causing strains makes predictions of the correct treatment for sepsis increasingly difficult. The current gold standard for diagnosis of the microorganisms causing sepsis is based on phenotypic and biochemical identification techniques which require the isolation and culture of pure cultures of the infecting microorganisms. It can take several days to perform the microbial identification (ID) and antibiotic susceptibility (AST) tests to identify the infection and determine the susceptibility profile of antimicrobial resistant microorganisms. Current clinical practice requires treatment with a broad-spectrum antibiotic within 1 hour of suspicion of sepsis based on clinical symptoms. A second dose is required within 6-8 hours and this administration is continued every sixth to eighth hour until identification of the microorganism and its antibiotic susceptibility (ID/AST) is established.

Due to the lethal condition of sepsis physicians are unwilling to change treatment from broad-spectrum antibiotics initially if the patient experiences a clinical response until the nature of the microbial infection is determined and antimicrobial susceptibility established. This in turn leads to the unnecessarily high use of broad spectrum antibiotics, in turn fueling the rise of antimicrobial resistance among microorganisms.

Medical conditions caused by microbiological agents are generally diagnosed through the testing of a sample taken from a patient. A key objective (particularly with life-threatening conditions with a rapid progression rate, such as sepsis) is to have the sample analyzed as quickly as possible, so that the microbe can be identified and a rise of antimicrobial resistance among microorganisms.

Conventional testing methods utilize turbidity measurements or disc diffusion to assess the effect of antimicrobial agents on microorganism growth, and traditional biochemical and microbiological techniques to identify a microorganism. These techniques can take several days to identify and characterize a microorganism in a clinical sample, due to the requirement for prolonged periods of incubation to allow microbial growth. There is thus a requirement for techniques that can rapidly identify microorganisms and determine the antimicrobial susceptibility profile of antimicrobial resistant microorganisms, and various different techniques that reduce the time between sample collection and diagnosis have been developed in recent years.

Methods of enriching microorganisms in a clinical sample that bypass the requirement for long periods of incubation are described in U.S. Pat. No. 8,481,265; microbial cells can be enriched from clinical samples by the selective lysis of non-microbial cells, enriching the concentration of microbial cells in a sample and bypassing the requirement for prolonged incubation prior to testing a sample.

Methods of rapid microbial identification are described in US 2010/0124763, in which microbial cultures are enriched and microorganisms identified spectroscopically.

Rapid susceptibility testing techniques using flow cytometry (Broeren et al. 2013 Clin Microbiol Infect 19, 286-291) and automated microscopy (Price et al. 2014 JMM. 98 50-59) have been developed to reduce the time required for incubation prior to susceptibility being determined. Quantitative PCR of microbial DNA has also been used as a measure for microbial growth to determine antimicrobial susceptibility, as described in U.S. Pat. No. 5,789,173.

Combined microorganism identification and susceptibility testing methods have also been developed. Described in US 2005/0095665 A1 is a system in which panels of selected growth media and chromogenic and fluorogenic substrates are used in combination with turbimetric measurement of microbial growth in an automated microtiter well format to identify microorganisms and determine antimicrobial susceptibility. Automated microscopy methods have also been developed (Metzger et al. 2014 Diagnostic Microbiology and Infectious Disease 79 160-165). The BD Phoenix™ system also allows for the rapid simultaneous identification and characterization of microorganisms, and utilizes a variety of chromogenic and fluorogenic substrates to identify microorganisms in a sample and minor microbial growth to determine the antimicrobial susceptibility of microorganisms in a sample.

Further combined microorganism identification and susceptibility testing methods and devices therefor are described in the Applicant's commonly-owned and co-pending application WO2015/189390. A portion of a clinical sample is tested for the presence of a microorganism via molecular-based microbial identification methods, which are performed whilst the clinical sample is cultured to allow microbial growth to take place. Once a microorganism is identified, an antimicrobial susceptibility test (AST) assay may be performed on the cultured clinical sample in order to determine the susceptibility of the microorganism to one or more antimicrobial agents. Thus, the rapid identification of the causative agent of sepsis and information on its susceptibility to antimicrobial agents may quickly and efficiently be established.

However, despite these advances in the processing of clinical samples, there remain unnecessary delays in the processing of clinical samples, which hamper diagnostic efforts.

BRIEF DESCRIPTION

According to a first aspect of the present invention, there is provided a method for detecting and characterizing a microorganism in a clinical sample, said method comprising:
- a) introducing a clinical sample to a first culture vessel containing culture medium,
- b (i)) simultaneously transporting and incubating the clinical sample, wherein said transporting and incubating comprises placing the first culture vessel in a thermally insulated compartment of a sealable container and heating the clinical sample to a temperature suitable for pre-culturing of the sample, wherein the thermally insulated compartment and the heating are used to keep the clinical sample at the temperature suitable for pre-culturing during transport of the sample, thereby to pre-culture the clinical sample;
- b (ii)) optionally continuing to culture said clinical sample in said first culture vessel;
- b (iii)) optionally removing a portion of the clinical sample culture from said first culture vessel, and introducing said portion to a second culture vessel containing culture medium, and optionally preculturing said portion in said second culture vessel;
- c) removing a test aliquot from said first and/or second culture vessel, and continuing to culture said clinical sample and/or portion in said first and/or second culture vessel;
- and separating DNA from the test aliquot and performing nucleic acid tests on the DNA to identify a microorganism and/or to detect the presence or absence of one or more genetic antimicrobial resistance markers in the microorganism, and/or determining the antimicrobial susceptibility of a microorganism in the clinical sample.

Indeed, in any of the embodiments of this aspect of the present invention, ID and/or AST tests (e.g., further ID and/or AST tests), whether conventional or not, may be performed on the cultured sample or portion. The method therefore allows for culture of the clinical sample or portion to take place to allow additional identification and/or AST tests to be performed, for example simply to provide an additional result, e.g., as a back-up or confirmation. In a further embodiment, further (e.g., conventional) tests may be performed whether or not the identity and/or antimicrobial susceptibility of the microorganism are determined. In a preferred aspect, culturing of the clinical sample (i.e., of the first culture vessel) is continued to enable further microbial identification and antimicrobial susceptibility tests to be performed.

It will further be understood that identification and/or AST determination may be performed one or more times. That is to say aliquots may be removed from the first or second culture one or more times, e.g., at intervals, so that an ID and/or AST test may be performed one or more times (e.g., two or more times, e.g., 2 or 3 times).

As noted above, culture of the clinical sample in the first culture vessel may be continued, whilst an AST test is on-going, and optionally also after the test has been performed. Thus, the possibility exists of repeating the AST test or of continuing the culture further to allow conventional testing. As is clear from the context, an aliquot of the cultured clinical sample or portion removed therefrom in the first or second culture vessel is simply a portion, i.e., a part or fraction of the culture vessel contents. The aliquot may be removed and used directly for an ID and/or AST test, or it may be subjected to a period of culture before performing such tests. Further, a test aliquot removed from the first or second culture vessel may be divided into sub-aliquots or aliquot fractions, or a sub-aliquot or fraction may be removed therefrom, which may be subjected to testing or further culture. This culture of a removed test aliquot or aliquot fraction may be performed separately, or independently, of the culture or continued culture of the clinical sample in the culture vessel.

According to any one of the embodiments of the first aspect of the present invention outlined above, the nucleic acid tests may be performed using:
- i) one or more nucleic acid probes and/or primers for microbial identification, a probe or primer thereof being capable of hybridizing specifically to, or a primer thereof being capable of selectively amplifying, a nucleotide sequence which is identificatory of a given microorganism; and/or
- ii) one or more nucleic acid probes and/or primers for antimicrobial resistance marker detection, a probe or primer thereof being capable of hybridizing specifically to, or a primer thereof being capable of selectively amplifying, a nucleotide sequence representing a genetic antimicrobial resistance marker.

In an alternative embodiment, the method comprises performing an antimicrobial susceptibility test on a cultured clinical sample obtained from the first culture vessel after the continued culturing, wherein microbial growth in the antimicrobial susceptibility test is monitored by assessing growth or markers for growth.

In yet another embodiment, if a microorganism is identified in the nucleic acid tests, performing an antimicrobial susceptibility test on said cultured clinical sample and/or portion from step (c) after the continued culturing, wherein microbial growth in said antimicrobial susceptibility test is monitored by assessing growth or markers for growth, and wherein the type and concentration of antimicrobial agents used in said antimicrobial susceptibility test is determined by the identity of the microorganism and antimicrobial resistance markers detected in the nucleic acid test, and optionally continuing to culture said clinical sample and/or portion in said first culture vessel and/or second culture vessel.

Accordingly, according to another aspect of the present invention, there is provided a method for detecting and characterizing a microorganism in a clinical sample, said method comprising:
- a) introducing a clinical sample to a first culture vessel containing culture medium,
- b (i)) simultaneously transporting and incubating the clinical sample, wherein said transporting and incubating comprises placing the first culture vessel in a thermally insulated compartment of a sealable container, heating the clinical sample to a temperature suitable for pre-culturing of the sample, wherein the thermally insulated compartment and the heating are used to keep the clinical sample at the temperature suitable for pre-culturing during transport of the sample, thereby to pre-culture the clinical sample;

b (ii)) optionally continuing to culture said clinical sample in said first culture vessel;

b (iii)) optionally removing a portion of the clinical sample culture from said first culture vessel, and introducing said portion to a second culture vessel containing culture medium, and optionally preculturing said portion in said second culture vessel;

c) removing a test aliquot from said first and/or second culture vessel, and continuing to culture said clinical sample and/or portion in said first and/or second culture vessel;

d) separating DNA from said test aliquot;

e) performing nucleic acid tests on said DNA to identify the microorganism and to detect the presence or absence of one or more genetic antimicrobial resistance markers in said microorganism, wherein said nucleic acid tests are performed using:

i) one or more nucleic acid probes and/or primers for microbial identification, a said probe or primer being capable of hybridizing specifically to, or a said primer being capable of selectively amplifying, a nucleotide sequence which is identificatory of a given microorganism; and ii) one or more nucleic acid probes and/or primers for antimicrobial resistance marker detection, a said probe or primer being capable of hybridizing specifically to, or a said primer being capable of selectively amplifying, a nucleotide sequence representing a genetic antimicrobial resistance marker;

and it is detected whether or not said probes and/or primers have hybridized to said DNA and/or said primers have been extended (e.g., an amplification reaction has taken place); and f) if a microorganism is identified in step (e), performing an antimicrobial susceptibility test on said cultured clinical sample and/or portion from step (c), wherein microbial growth in said antimicrobial susceptibility test is monitored by assessing growth or markers for growth, and wherein the type and concentration of antimicrobial agents used in said antimicrobial susceptibility test is determined by the identity of the microorganism and antimicrobial resistance markers detected in step (e), and optionally continuing to culture said clinical sample and/or portion in said first culture vessel and/or second culture vessel.

BRIEF DESCRIPTION OF THE DRAWINGS

Preferred embodiments of the present invention will now be described by reference to the accompanying figures, in which:

FIG. 3 shows the relative growth of bacteria grown in MH broth supplemented with a number of different antibiotics, each at a range of different concentrations, relative to positive control samples grown in the absence of any antibiotics (A—Cefotaxime, B—Ciprofloxacin, C—Gentamicin, D—Meropenem, E—Ceftazidime, F—Piperacillin+Tazobactam).

Figure 4:
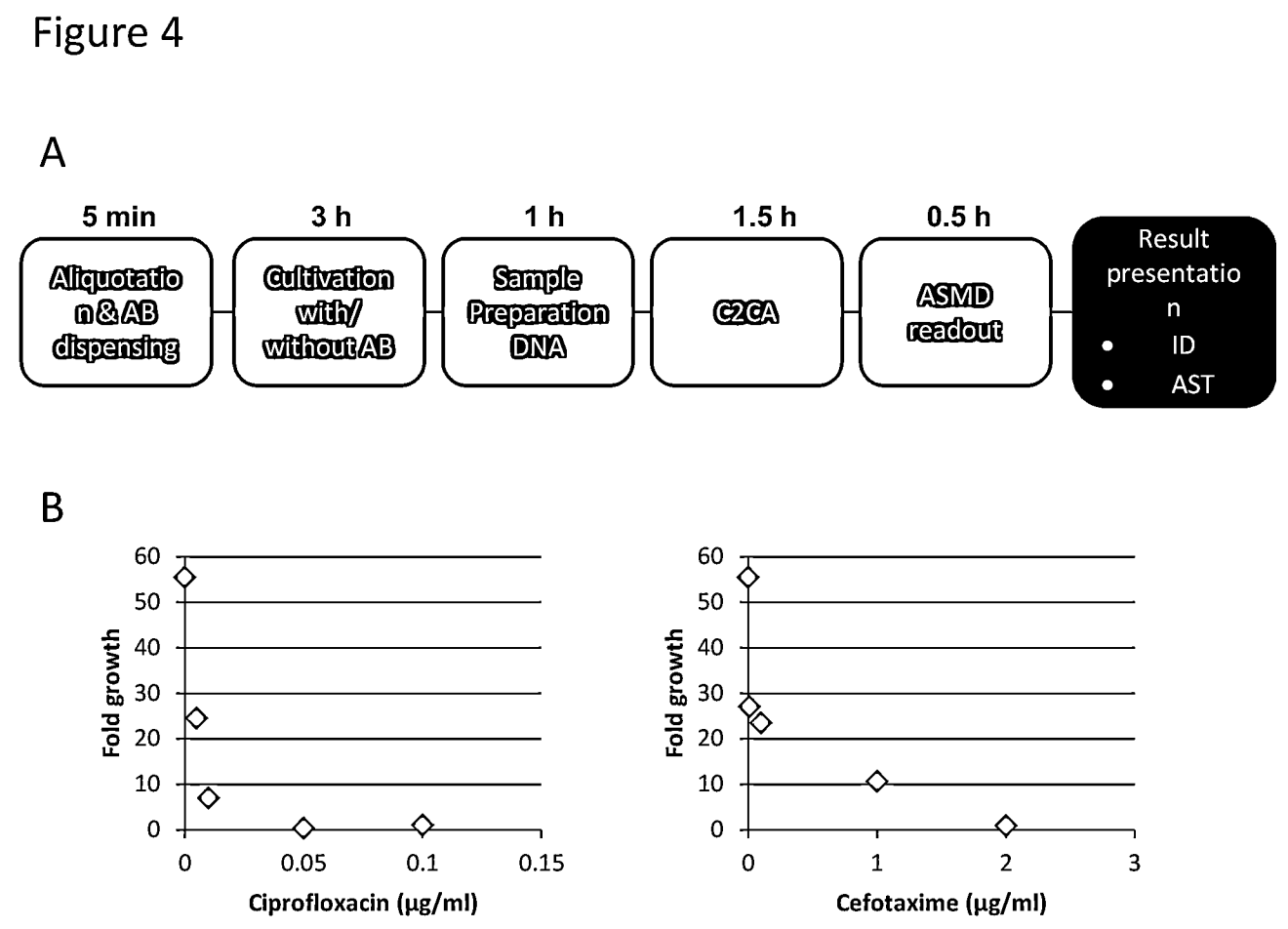

FIG. 4 depicts in (A) the workflow required for Amplified Single Molecule Detection (ASMD) of bacteria within a sample to determine antibiotic susceptibility of a microorganism, and in (B) shows the differential growth of bacteria grown in MH broth supplemented with Ciprofloxacin or Cefotaxime, relative to a positive control sample grown in the absence of either antibiotic.

Figure 5:
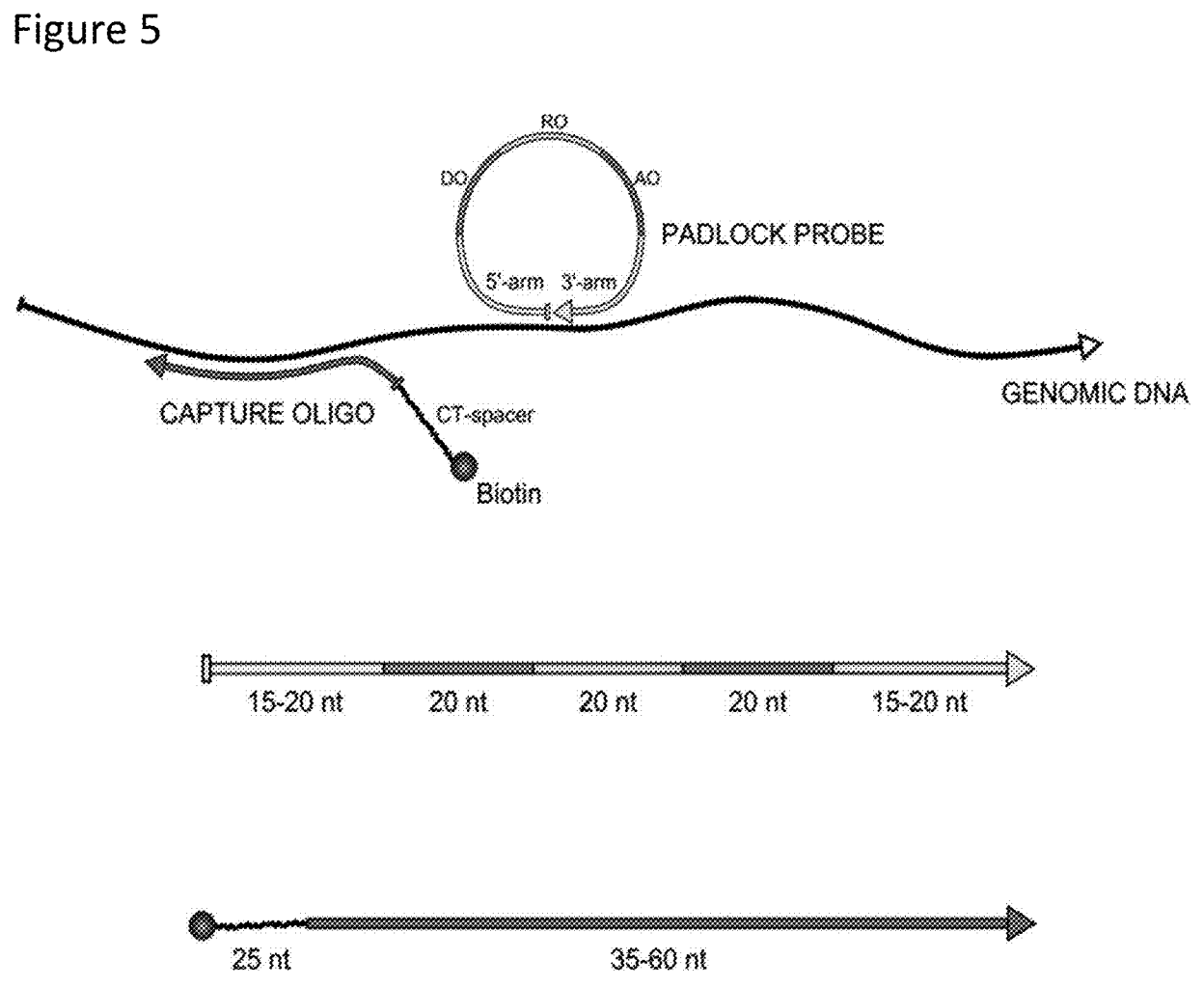

FIG. 5 depicts a scheme for detecting specific microbial DNA sequences for use in probe design.

Figure 6:
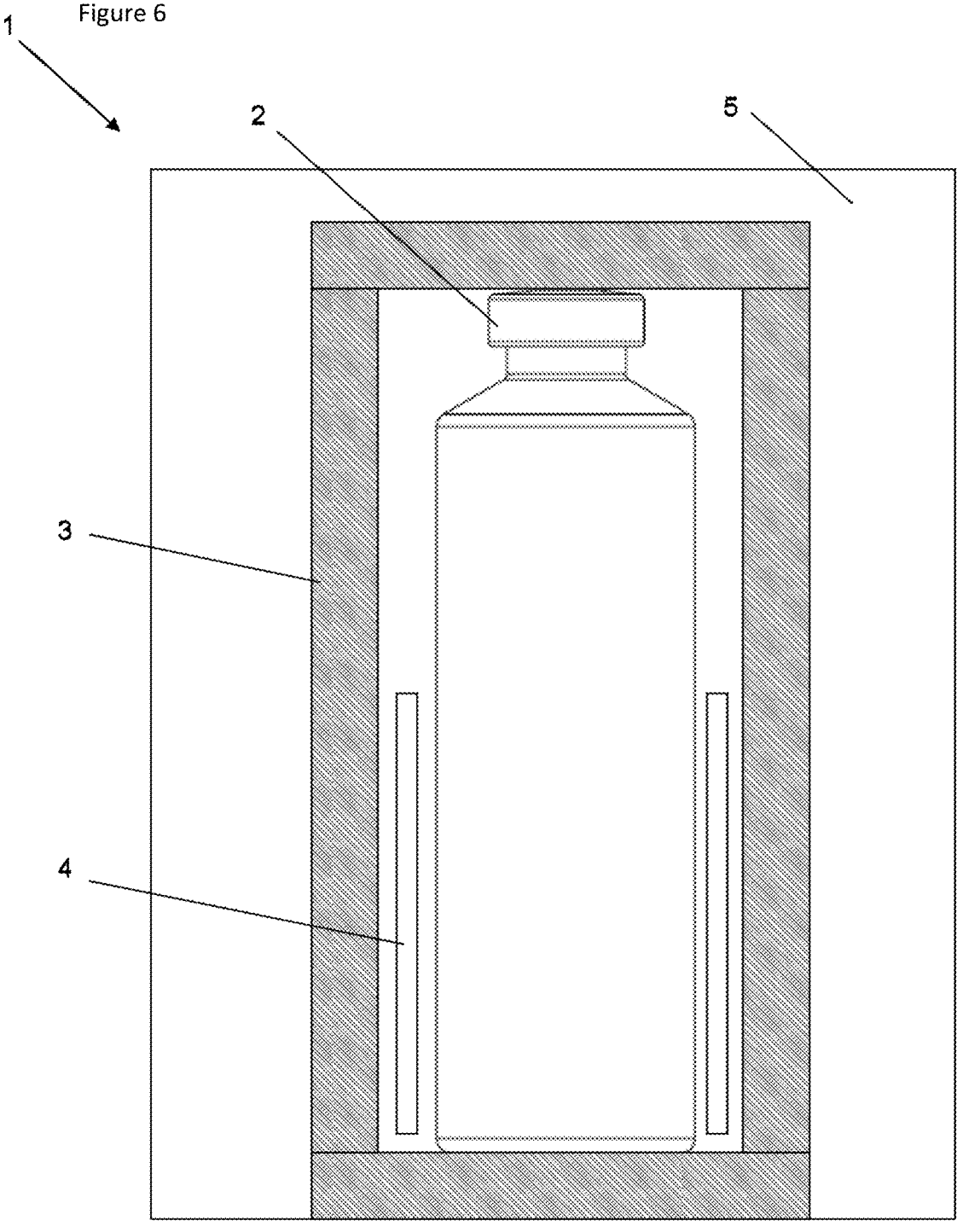

FIG. 6 shows a portable apparatus for transport of a clinical sample in a culture vessel.

Figure 7:
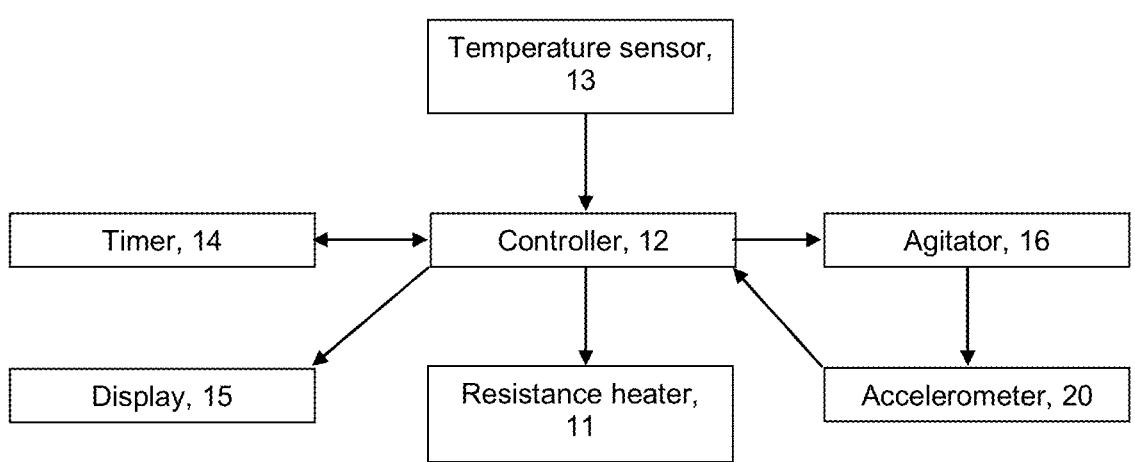

FIG. 7 shows a schematic of a controller, temperature sensor, heater, agitator, accelerometer, timer and display for use in a portable apparatus as shown in the Figures.

Figure 8A:
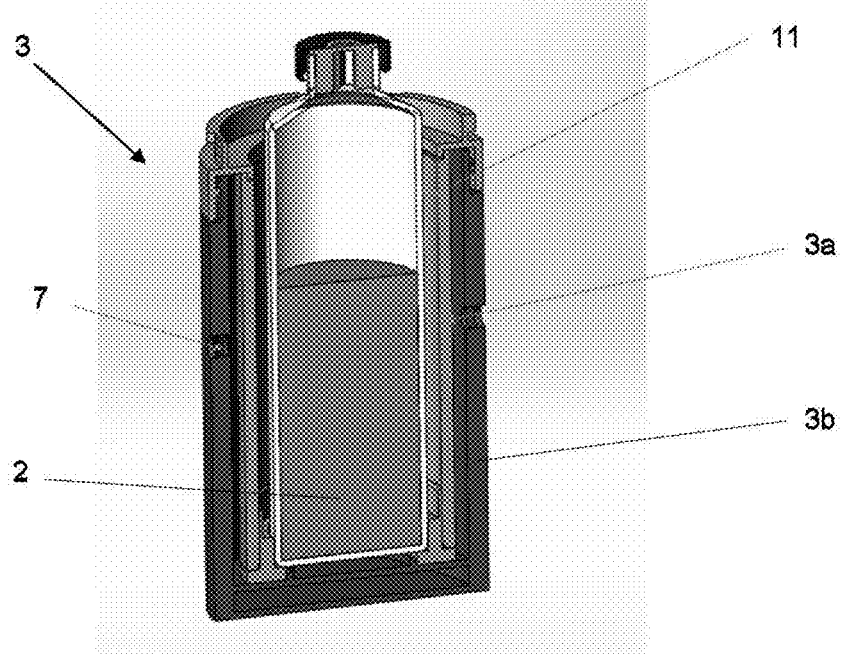
Figure 8B:
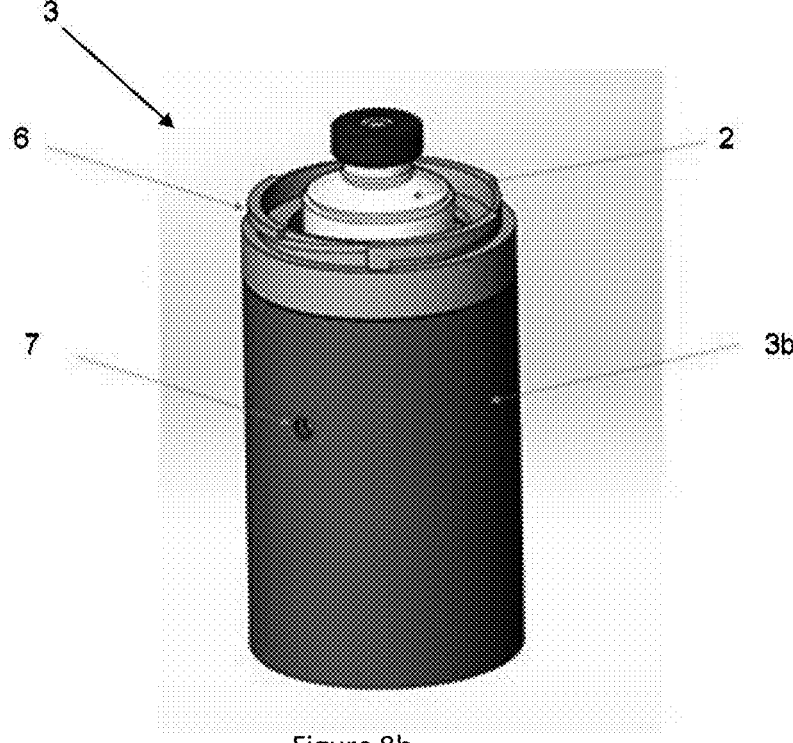

FIGS. 8a and 8b show further details of a part of another a portable apparatus for transport of a clinical sample in a culture vessel.

Figure 9:
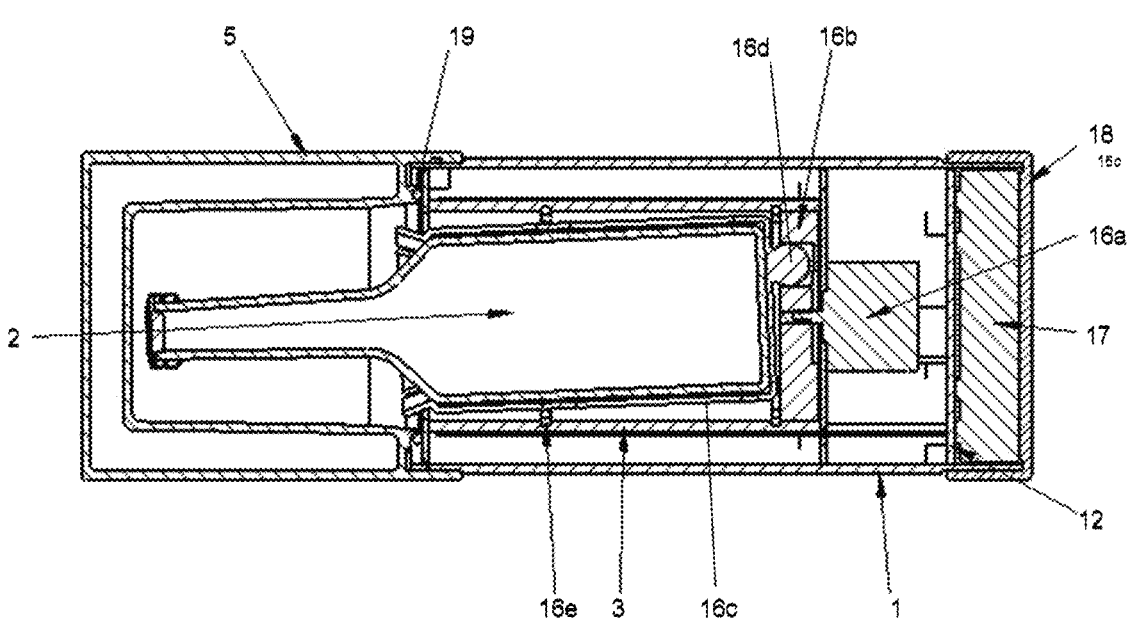

FIG. 9 shows a cross-section of another portable apparatus showing the details of a possible agitation mechanism.

Figure 10:
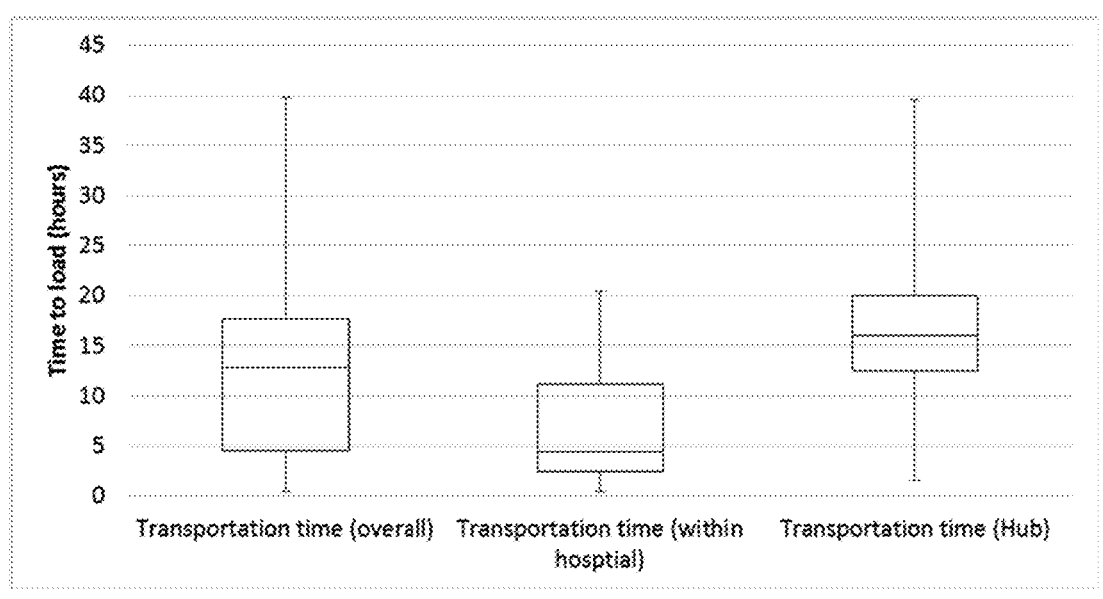

FIG. 10 is a box-whisker diagram showing typical times for transport of samples from a patient to a diagnostic system.

Figure 11A:
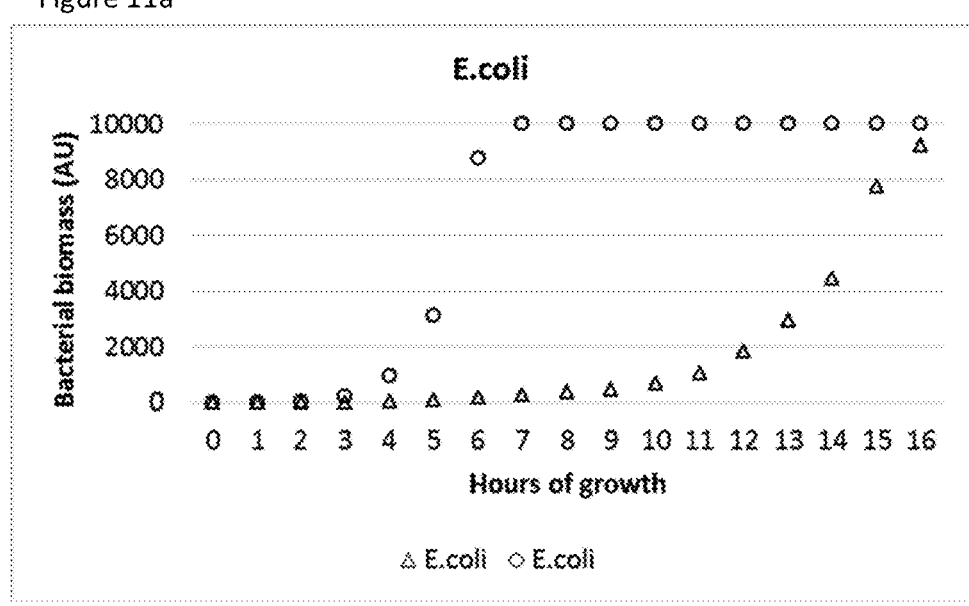
Figure 11B:
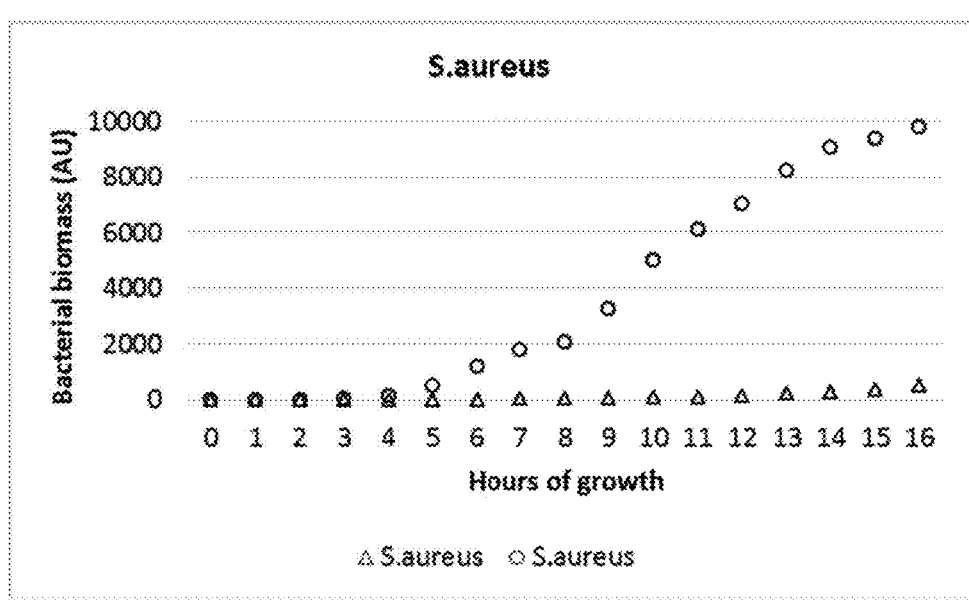
Figure 11C:
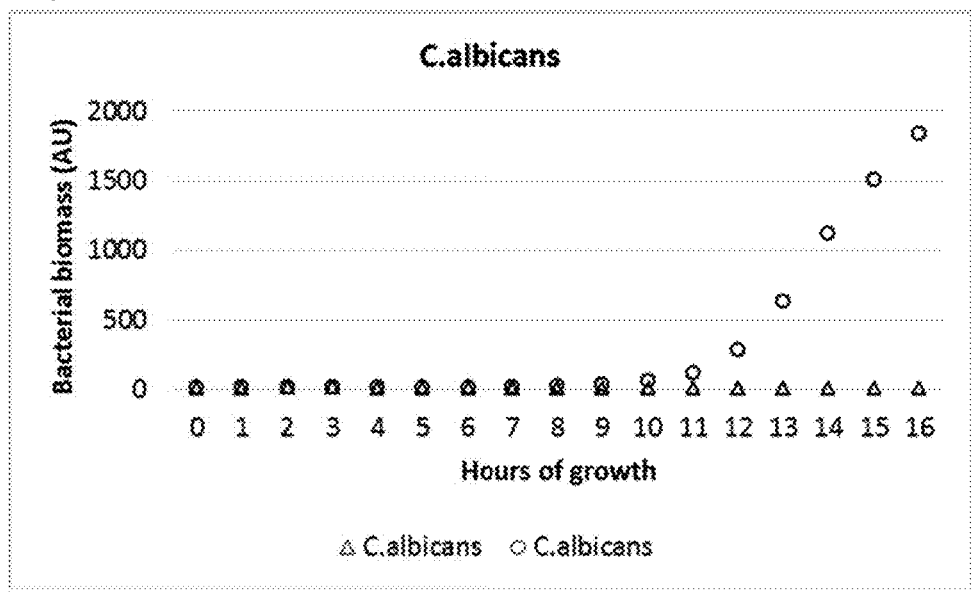

FIGS. 11a, 11b, and 11c show growth of bacteria at room temperature (triangular data points) as compared to at 35° C. (circular data points) for (a) E. coli, (b) S. aureus and (c) C. albicans.

DETAILED DESCRIPTION

The inventors have made the non-obvious realization that for some diagnostic systems, such as those described in WO 2015/189390, pre-culturing the clinical sample comprising the microorganism with heating and optionally agitation before it is introduced into a diagnostic system may be advantageous, as this allows the amount of time required for incubation of a sample in the system to be reduced, thereby allowing sample testing to be run sooner. In particular, there is often a long lead-time from the time that the sample (for example, blood) is taken from a patient to the time that the sample is placed in an automated culture cabinet in the microbiology laboratory. Blood samples are typically collected, transported and cultured in the culture cabinet within blood culture flasks (blood culture flasks). Examples of blood culture flasks are BacT/Alert® (Biomerieux), Bactec™ (Becton Dickinson) and VersaTrek® (Thermo Fisher).

Typically, methods for detecting a microorganism in a sample rely on detecting differences in the number of microbial cells present in a sample at two or more dime points, and thus rely on measuring microbial growth during the 'log-phase' of growth. Pre-culturing has therefore typically been avoided in the art, as there is a risk of yielding a false negative result for microbial growth in certain culture devices in cases where microbial growth has occurred before the sample is placed in an automated culture cabinet (i.e., pre-culturing), e.g., if the population of microbial cells has reached the 'stationary-phase' of growth. For this reason, samples are generally transported to the microbiology laboratory in containers (which may be insulated) which are either maintained at room temperature, or are cooled to below room temperature. However, pre-culturing is acceptable if the analysis is not dependent on a positive determination of microbial growth, i.e., on detecting a positive sample in a conventional culture cabinet, and where pre-culturing is acceptable, it is advantageous to pre-culture the sample as it is in transit to the laboratory. Many microbiology labs run around the clock, and yet still there are unnecessary delays in sample processing. The method of this aspect gets an advantage from the long lead-time from the time that the sample (for example, blood) is taken (from a patient) to the time that the sample is placed in an automated culture cabinet in a diagnostic system in a microbiology laboratory. The inventors have recognized that contrary to the prior art approach for this type of sample it is advantageous to heat the sample to above room temperature after it has been collected from a test subject and to thereby incubate the sample during transport, rather than cooling it or maintaining it at room temperature.

Prior art transport containers for culturing are known within the field of cell-culture and tissue transportation as the cost and need are higher in that field. One example of such a container is described in U.S. Pat. No. 8,074,465. This discloses a thermally insulated transport container system comprising: a closable container having a thermally insulated portion, the container being configured for storage or shipment of a skeletal myoblast cell-based product; a sealable canister within the container, the canister being configured for holding the skeletal myoblast cell-based product; and a refrigerant within the container, the refrigerant being configured to maintain an internal temperature in the canister in the range of −5° C. to 15° C. for a period of at least 72 hours. However, this prior art presents no suggestion to use such a container in the context of the method of the invention.

The prior art also includes containers that are designed for transport and heating of biological material in order to preserve the biological material. For example, GB 2055530 discloses an electrically heated case for transporting infusion solution and U.S. Pat. No. 6,028,293 discloses a temperature-controlled container for transporting biological tissue including human skin. It is however important to realize that the purpose of such devices is considerably different to the purpose of the device of U.S. Pat. No. 8,074,465 and the like, and is further very different to the purpose of the container in the current method, since preservation of biological materials is done for very different reasons than incubation of clinical samples to culture the sample. Indeed, one skilled in the art would not consider the use of a tissue preservation device as in GB 2055530 or U.S. Pat. No. 6,028,293 for incubation of a sample as proposed in U.S. Pat. No. 8,074,465.

An incubation device using heating in a portable device is described in US 2013/226032. The disclosure relates to stimulation of whole blood and then chilling of the blood in the same container during transport and storage of the blood. The blood is held in blood vacuum collection tubes and manual processing of these tubes is required to manually add active ingredients such as anticoagulants and stimulants, and to then introduce a leukocyte membrane to the tubes.

A portable apparatus as described below can be used for transportation of a clinical sample whilst pre-culturing the clinical sample. The portable apparatus described herein may be provided as a part of a broader testing system for testing a clinical sample. The portable apparatus is used for transporting and pre-culturing the clinical sample prior to testing, which provides significant benefits in relation to the time taken to obtain a final test result. Following the period of pre-culture (i.e., transportation), the first culture vessel, which is preferably a blood culture flask, may be introduced into a clinical sample processing system. An example embodiment of the present invention thus provides a clinical sample testing system comprising: the portable apparatus as described, for example, with reference to FIGS. 6 to 9, along with a clinical sample processing system for further testing of the clinical sample.

Advantageously, the portable apparatus allows the pre-culture of a clinical sample between the point at which the clinical sample is introduced into a culture vessel, and the point at which the culture vessel is introduced into a clinical sample processing system. This therefore allows a greater degree of microbial growth than would be achieved in the absence of incubation, thereby increasing the number of microbial cells in a sample available for testing. This may advantageously reduce the incubation time that is required before subsequent testing steps may be performed, and/or increase the efficacy and/or sensitivity of such steps. By pre-culturing the microbial cells during what would otherwise be dead time in a workflow for diagnosing sepsis, the present invention in effect brings forward the point at which culture of the clinical sample is initiated, thereby reducing the time required after obtaining a sample from a patient for a successful diagnosis. The simultaneous transporting and incubating of a clinical sample in such a portable apparatus thus advantageously may be incorporated into a method for detecting and characterizing a microorganism in a clinical sample.

Following a period of pre-culture (i.e., during transportation), the first culture vessel may be introduced into a clinical sample processing system. As mentioned above and explained further below a dedicated instrument or device may be provided to perform any one of or all of the steps following step (b)(i) of the first aspect of the present invention, or steps (b)(ii)-(f) of the second aspect of the invention, which may be designed to receive the first culture vessel containing the clinical sample culture for culturing and AST and ID testing.

It will be seen that the methods of the present invention rely upon culturing a clinical sample as it is transported from a test subject to a location for testing (e.g., a pathology laboratory). Aliquots of the clinical sample culture may be taken to enable firstly molecular tests and secondly a rapid AST to be performed with a reduced, or without, a subsequent period of incubation required before testing may take place. Furthermore, the method allows molecular tests to be performed whilst preserving the option of using the same clinical sample for further conventional tests.

According to the second aspect of the invention, this may be done by culturing it while the molecular tests (step (e)), and optionally also the AST of step (f), are performed. This can be a single culture (e.g., continuing to incubate the clinical sample) or a further culture may be set up e.g., which may be used to provide an aliquot for testing whilst the first or initial culture is maintained in culture (i.e., continues to be cultured). Indeed, by continuing to culture the sample or portion during the molecular tests of step (e), and optionally also during step (f), the culturing required for the further (e.g., conventional) tests is in effect being performed in parallel with the molecular and AST tests of steps (e) and (f). Accordingly, step (f) of the method may in certain embodiments be expressed as performing an antimicrobial susceptibility test on a further aliquot of the cultured clinical sample or portion from step (c).

Thus, in one embodiment, this aspect of the invention provides a method comprising:

a) introducing a clinical sample to a culture vessel containing culture medium;

b (i)) simultaneously transporting and incubating the clinical sample, wherein said transporting and incubating comprises placing the culture vessel in a thermally insulated compartment of a sealable container, heating the clinical sample to a temperature suitable for pre-culturing of the sample, wherein the thermally insulated compartment and the heating are used to keep the clinical sample at the temperature suitable for pre-culturing during transport of the sample, thereby to pre-culture the clinical sample;

b (ii)) optionally continuing to culture said clinical sample in said culture vessel;

c) removing a test aliquot from said culture vessel, and continuing to culture said clinical sample in said culture vessel;

d) separating DNA from said test aliquot;

e) performing nucleic acid tests on said DNA to identify the microorganism and to detect the presence or absence of one or more genetic antimicrobial resistance markers in said microorganism, wherein said nucleic acid tests are performed using:

i) one or more nucleic acid probes and/or primers for microbial identification, a said probe or primer being capable of hybridizing specifically to, or a said primer being capable of selectively amplifying, a nucleotide sequence which is identificatory of a given microorganism; and ii) one or more nucleic acid probes and/or primers for antimicrobial resistance marker detection, a said probe or primer being capable of hybridizing specifically to, or a said primer being capable of selectively amplifying, a nucleotide sequence representing a genetic antimicrobial resistance marker;

and it is detected whether or not said probes and/or primers have hybridized to said DNA and/or said primers have been extended (e.g., an amplification reaction has taken place); and f) if a microorganism is identified in step (e), performing an antimicrobial susceptibility test on said cultured clinical sample from step (c), wherein microbial growth in said antimicrobial susceptibility test is monitored by assessing growth or markers for growth, and wherein the type and concentration of antimicrobial agents used in said antimicrobial susceptibility test is determined by the identity of the microorganism and antimicrobial resistance markers detected in step (e), and optionally continuing to culture said clinical sample in said culture vessel.

In the above embodiment, the culture vessel represents the first culture vessel according to the methods of the invention.

As noted above, in a further aspect a further culture may be set up from the clinical sample. In one such embodiment a clinical sample may be introduced into a first culture vessel, and after the period of pre-culture of the clinical sample (i.e., during transportation), a portion of the content of the first culture vessel may be removed and used to inoculate a second culture vessel. As mentioned above and explained further below a dedicated instrument or device may be provided to perform the method of the invention, and this may be used alongside a conventional culture system or instrument for performing conventional tests if desired or necessary (e.g., a culture cabinet from Becton Dickinson or Biomerieux). Such a dedicated instrument/device may be designed to receive the first culture vessel containing the clinical sample, and to remove a portion from the first culture vessel and introduce it into the second culture vessel.

This may allow the first culture vessel to be placed in a further culture system (e.g., incubator) for testing via conventional means, whilst the portion of the clinical sample culture obtained therefrom is retained in the device of the present invention for culturing (including optional preculturing) and AST and ID testing.

The method of this aspect of the present invention may therefore comprise:

a) introducing a clinical sample to a first culture vessel containing culture medium;

b (i)) simultaneously transporting and incubating the clinical sample, wherein said transporting and incubating comprises placing the first culture vessel in a thermally insulated compartment of a sealable container, heating the clinical sample to a temperature suitable for pre-culturing of the sample, wherein the thermally insulated compartment and the heating are used to keep the clinical sample at the temperature suitable for pre-culturing during transport of the sample, thereby to pre-culture the clinical sample;

b (ii)) optionally continuing to culture said clinical sample in said first culture vessel;

b (iii)) removing a portion of the clinical sample culture from said first culture vessel, and introducing said portion to a second culture vessel containing culture medium and optionally preculturing said portion in said second culture vessel;

c) removing a test aliquot from said second culture vessel, and continuing to culture said portion in said second culture vessel;

d) separating DNA from said test aliquot;

e) performing nucleic acid tests on said DNA to identify the microorganism and to detect the presence or absence of one or more genetic antimicrobial resistance markers in said microorganism, wherein said nucleic acid tests are performed using:

i) one or more nucleic acid probes and/or primers for microbial identification, a said probe or primer being capable of hybridizing specifically to, or a said primer being capable of selectively amplifying, a nucleotide sequence which is identificatory of a given microorganism; and ii) one or more nucleic acid probes and/or primers for antimicrobial resistance marker detection, a said probe or primer being capable of hybridizing specifically to, or a said primer being capable of selectively amplifying, a nucleotide sequence representing a genetic antimicrobial resistance marker;

and it is detected whether or not said probes and/or primers have hybridized to said DNA and/or said primers have been extended (e.g., an amplification reaction has taken place); and f) if a microorganism is identified in step (e), performing an antimicrobial susceptibility test on said cultured portion from step (c), wherein microbial growth in said antimicrobial susceptibility test is monitored by assessing growth or markers for growth, and wherein the type and concentration of antimicrobial agents used in said antimicrobial susceptibility test is determined by the identity of the microorganism and antimicrobial resistance markers detected in step (e), and optionally continuing to culture said portion in said second culture.

Indeed, in any of the embodiments of this aspect of the present invention further ID and/or AST tests, whether conventional or not, may be performed on the cultured sample or portion irrespective of whether or not a positive identification result in step (e) is obtained. The method therefore allows for culture of the clinical sample or portion to take place to allow additional identification and/or AST tests to be performed, for example simply to provide an additional result, e.g., as a back-up or confirmation. In a further embodiment, further (e.g., conventional) tests may be performed whether or not there is a positive result from the ID tests of step (e) and/or the AST test of step (f). In a preferred aspect, culturing of the clinical sample (i.e., of the first culture vessel) is continued to enable further microbial identification and antimicrobial susceptibility tests to be performed.

It will further be understood that the tests of steps (e) and/or (f) may be repeated, or performed one or more times, that is to say aliquots may be removed from the first or second culture one or more times, e.g., at intervals, to perform the nucleic acid tests of step (f) one or more times (e.g., two or more times, e.g., 2 or 3 times). Optionally, the AST test of step (f) may also be performed more than once, should this be desired. As noted above, culture of the clinical sample in the first culture vessel may be continued, whilst the AST test of step (f) is going, and optionally also after the test has been performed. Thus, the possibility exists of repeating the AST test or of continuing the culture further to allow conventional testing. As is clear from the context, an aliquot of the cultured clinical sample or portion removed therefrom in the first or second culture vessel is simply a portion, i.e., a part or fraction of the culture vessel contents. The aliquot may be removed and used directly for the nucleic acid tests of step (e), (that is after separating DNA from the test aliquot in step (d)), or in an AST test of step (f), or it may be subjected to a period of culture before performing the tests of steps (d)/(e) and/or step (f). Further, a test aliquot removed from the first or second culture vessel may be divided into sub-aliquots or aliquot fractions, or a sub-aliquot or fraction may be removed therefrom, which may be subjected to testing or further culture. This culture of a removed test aliquot or aliquot fraction may be performed separately, or independently, of the culture or continued culture of the clinical sample in the culture vessel.

Analogously to the embodiments of the second aspect of the present invention described above, according to the first aspect of the present invention, the first culture vessel may be introduced into a clinical sample processing system, and any or all of the steps following the initial simultaneous transportation and incubation step (b)(i) may be performed in or using such a system. A dedicated instrument or device may be provided to perform any one or all of such steps, which device may be designed to receive the first culture vessel containing the clinical sample culture for testing.

Similarly, aliquots of the clinical sample culture may be taken to enable microbial identification and/or characterization tests to be performed with a reduced, or without, a subsequent period of incubation required before testing may take place. Furthermore, the method allows molecular tests to be performed whilst preserving the option of using the same clinical sample for further conventional tests.

This may, for example, be done by culturing the clinical sample while such tests are performed. This can be a single culture (e.g., continuing to incubate the clinical sample) or a further culture may be set up e.g., which may be used to provide an aliquot for testing whilst the first or initial culture is maintained in culture (i.e., continues to be cultured). Indeed, by continuing to culture the sample or portion whilst the test is performed, the culturing required for the further (e.g., conventional) tests is in effect being performed in parallel with the identification and/or characterization tests according to this aspect of the invention.

Thus, in one embodiment, this aspect of the invention provides a method comprising:
- a) introducing a clinical sample to a culture vessel containing culture medium;
- b (i)) simultaneously transporting and incubating the clinical sample, wherein said transporting and incubating comprises placing the culture vessel in a thermally insulated compartment of a sealable container, heating the clinical sample to a temperature suitable for pre-culturing of the sample, wherein the thermally insulated compartment and the heating are used to keep the clinical sample at the temperature suitable for pre-culturing during transport of the sample, thereby to pre-culture the clinical sample;
- b (ii)) optionally continuing to culture said clinical sample in said culture vessel;
- c) removing a test aliquot from said culture vessel, and continuing to culture said clinical sample in said culture vessel;
- and separating DNA from the test aliquot and performing nucleic acid tests on the DNA to identify a microorganism and/or to detect the presence or absence of one or more genetic antimicrobial resistance markers in the microorganism, and/or determining the antimicrobial susceptibility of a microorganism in the clinical sample.

In the above embodiment, the culture vessel represents the first culture vessel according to the methods of the invention.

In a further embodiment, a further culture may be set up from the clinical sample as described above according to the second aspect of the invention.

The method of this aspect of the present invention may therefore comprise:
- a) introducing a clinical sample to a first culture vessel containing culture medium;
- b (i)) simultaneously transporting and incubating the clinical sample, wherein said transporting and incubating comprises placing the first culture vessel in a thermally insulated compartment of a sealable container, heating the clinical sample to a temperature suitable for pre-culturing of the sample, wherein the thermally insulated compartment and the heating are used to keep the clinical sample at the temperature suitable for pre-culturing during transport of the sample, thereby to pre-culture the clinical sample;
- b (ii)) optionally continuing to culture said clinical sample in said first culture vessel;
- b (iii)) removing a portion of the clinical sample culture from said first culture vessel, and introducing said portion to a second culture vessel containing culture medium and optionally preculturing said portion in said second culture vessel;
- c) removing a test aliquot from said second culture vessel, and continuing to culture said portion in said second culture vessel;
- and separating DNA from the test aliquot and performing nucleic acid tests on the DNA to identify a microorganism and/or to detect the presence or absence of one or more genetic antimicrobial resistance markers in the microorganism, and/or determining the antimicrobial susceptibility of a microorganism in the clinical sample.

In the methods of the present invention, the pre-culture of the clinical sample (i.e., the pre-incubation during transport)

takes place within a portable apparatus comprising a sealable container having a thermally insulated compartment for receiving the first culture vessel; and a heater for heating the clinical sample to a temperature suitable for pre-culturing of the sample.

The clinical sample may preferably be maintained at a temperature suitable for pre-culturing of the sample. Suitable temperatures for pre-culturing the sample may vary depending on the microorganism present in the sample, however, contemplated preferred temperatures are from 20 to 40° C., or 25 to 40° C. e.g., 25 to 37° C., or 30 to 35° C. Here, maintaining the temperature means holding the temperature of the sample within a given range (at which pre-culturing can still take place) for a predetermined length of time, or until the culture vessel is removed from the container. Preferably the sample is maintained at a temperature which is within 5 degrees of the optimal temperature, more preferably within 2 degrees of the optimal temperature.

In certain embodiments, the first culture vessel may be agitated during transport, thereby to agitate the sample. Thus, in certain embodiments, the clinical sample may be agitated during transport. The culture vessel may be agitated periodically or continuously. Thus, the portable apparatus may in certain embodiments comprise an agitator (an agitator mechanism) for agitating sample within the culture vessel during transportation. This may be a mechanism for agitating the culture vessel itself and thereby agitating the sample, for example by moving the culture vessel relative to the portable apparatus. Alternatively, the vessel may remain fixed relative to the portable apparatus with the sample being moved within the vessel, such as by a magnetic stir bar or differential heating as discussed below.

Depending on the nature of the vessel, medium, suspected microorganism, clinical condition etc., the vessel and/or the sample within the vessel may be stirred or rotated, shaken etc. Agitation during heating ensures even heating of the sample as well as promoting effective culturing of the sample (e.g., by allowing even distribution of nutrients in the sample and/or allowing aeration of the sample, and/or to discourage biofilm formation and/or microbial clumping during pre-culture). In certain instances, the use of agitation has thus been found to be beneficial to the operation of the pre-culturing apparatus. Representative modes of agitation are discussed in reference to the arrangement of the portable apparatus below.

Pre-culture of the clinical sample is performed during the period of time between obtaining a clinical sample from a test subject and introducing (e.g., inserting) the first culture vessel containing the clinical sample into the clinical sample processing system. Typically, this might be at least 1, 2, 3, 4, 5 or 6 hours. Pre-culturing can take place for any suitable or desired time period, but in order to speed up the method it will preferably be for a short time period of less than 8 or less than 6 hours. For example, pre-culture may take place for up to 1, 2, 3, 4, 5 or 6 hours prior to the commencement of testing, or more particularly prior to removal of the test aliquot in step (c). Alternatively, preculturing can take place for less than 1 hour. Preculturing can also take place for more than 6 hours, for example for 7, 8 or 9 hours, or more than 9 hours, for example up to 10, or 12 hours, or even longer, but in the interests of providing a rapid method it is generally kept to a minimum, and short pre-culture periods of up to 6, or more particularly up to 4 or 3 hours are preferred. As noted above, preculture may take place for a period shorter than is required to see a positive culture result or it may take place until a positive culture result is obtained.

The step of culturing the clinical sample in the first culture vessel or of the portion removed from the first culture vessel, or indeed of culturing a test aliquot/aliquot fraction, may be performed in any convenient or desired way, as described in more detail below. In this regard, culture apparatus for culture of clinical samples for e.g., diagnostic or microbial detection purposes are known and may be used. Different culture apparatus or culture systems may be used for the separate culture of the culture vessel (e.g., the first and second culture vessels), and/or of any removed test aliquots/aliquot fractions and/or for the culture required during the AST test. Furthermore, as mentioned above and described in more detail below, it is envisaged according to the present invention also to provide an apparatus, or device, for performing the microbial detection and characterization method as described herein. Such a device, or system, may include apparatus or means for culturing the culture vessel. Accordingly, the various culture steps of the method, including the culture/continued culture of the first and/or second culture vessel, the culture of a test aliquot or aliquot fraction, or indeed also culture during an AST test (e.g., the AST test of step (f) according to the second aspect of the present invention) may be performed in the same or different culture systems or culture apparatus. Thus, in one embodiment, following pre-culturing step (b)(i), the first culture vessel may be introduced into a culture apparatus or culture system for continued culture of the clinical sample. Preferably, the culture apparatus or culture system may be a microorganism detection device as described in greater detail below. The first and/or second culture vessel may additionally, or alternatively, be transferred to a different culture system/apparatus, for example if there is a negative result from the identification test of step (e).

The surface of a culture vessel (e.g., the first and/or second culture vessel) may be cleaned or decontaminated prior to being placed in a culture apparatus (e.g., after the clinical sample or portion has been introduced into the culture vessel).

Thus, for example, in one embodiment, the culture vessel (e.g., the first culture vessel) may be cultured in one system whilst the testing steps are being performed. If an identification test (e.g., the identification tests of step (e) according to the second aspect of the present invention) is negative and/or inconclusive, or if an AST test (e.g., the AST test of step (f) according to the second aspect of the invention) is negative, inconclusive or incomplete, the culture vessel may then be transferred to a further, or separate culture system, e.g., to enable conventional identification tests and/or AST tests to be performed. For example, such a further or separate culture system may be a conventional culture cabinet, or a further automated microbial testing/detection system (e.g., diagnostic system).

In certain embodiments, the methods of the present invention thus may comprise a step of further culturing the clinical sample and/or portion if no microorganism strain is identified in step (e) to enable further microbial identification and antimicrobial susceptibility tests to be performed to identify the microorganism and determine its antimicrobial resistance profile.

By way of representative example, in one embodiment according to the second aspect of the invention, the clinical sample, collected from a test subject, is introduced into a culture vessel, and pre-cultured in a portable apparatus comprising a sealable container having a thermally insulated compartment for receiving the culture vessel prior to a test aliquot being removed (step (c)) and being subjected to steps (d) and (e). Whilst steps (d) and (e) are performed, the culture vessel is cultured. Optionally, the culture vessel may be introduced into a culture apparatus or culture system prior to step (c). If the identification test step (e) yields a positive result, a further aliquot may be removed from the culture vessel and subjected to the AST of step (f). If the identification test in step (e) is negative, the culture vessel containing the clinical sample may be subjected to further culturing, e.g., in a separate system.

In a further embodiment, a test aliquot is removed from the culture vessel (step (c) as above), and from this aliquot a fraction is subjected to steps (d) and (e) (nucleic acid separation and detection). During this time a further aliquot fraction or the remainder of the test aliquot is subjected to culture, as is the culture vessel from which the test aliquot is removed. This culture of the separate aliquot/aliquot fraction and culture vessel may take place in the same or different systems. If the identification test of step (e) yields a positive result, the cultured further aliquot fraction/remaining aliquot is subjected to the AST of step (f). If the identification test in step (e) is negative, the culture vessel containing the clinical sample is subjected to further culturing, e.g., in a separate system.

In yet another embodiment, a portion is removed from the first culture vessel after the period of preculture and introduced into a second culture vessel containing culture medium. A test aliquot is removed from the second culture vessel (step (c), and subjected to steps (d) and (e). During this time the second culture vessel is cultured. If the identification test of step (e) yields a positive result, a further aliquot is removed from the second culture vessel and subjected to the AST of step (f). If the identification test in step (e) is negative, the second culture vessel containing the sample aliquot is subjected to further culturing. In a further embodiment, the first culture vessel may additionally or instead be subjected to further culturing, e.g., in a separate system.

Any of the above embodiments may include continued culture of the first culture vessel containing the clinical sample irrespective of whether a positive or negative identification result in step (e) was obtained. In this way an additional result may be obtained from the sample.

Analogously, in embodiments according to the first aspect of the present invention the clinical sample, collected from a test subject, is introduced into a culture vessel, and pre-cultured in a portable apparatus comprising a sealable container having a thermally insulated compartment for receiving the culture vessel prior to a test aliquot being removed (step (c)) and being subjected to nucleic acid tests to identify a microorganism and/or to detect the presence or absence of one or more genetic antimicrobial resistance markers in the microorganism, and/or determining the antimicrobial susceptibility of a microorganism in the clinical sample. Whilst these steps are performed, the culture vessel is cultured. Optionally, the culture vessel may be introduced into a culture apparatus or culture system prior to step (c). A further aliquot or aliquots may be removed from the culture vessel and subjected to an additional test or tests, e.g., a test for the purpose of determining the antimicrobial susceptibility of a microorganism in the clinical sample if a test for the purpose of identifying said microorganism had been previously performed, or alternatively, if the result of a first test is negative (e.g., a microbial ID test) the test may be repeated following such a period of further culture. The culture vessel containing the clinical sample may alternatively or additionally be subjected to further culturing, e.g., in a separate system.

In a further embodiment, a test aliquot is removed from the culture vessel (step (c) as above), and from this aliquot a fraction is subjected to nucleic acid tests to identify a microorganism and/or to detect the presence or absence of one or more genetic antimicrobial resistance markers in the microorganism, and/or determining the antimicrobial susceptibility of a microorganism in the clinical sample. During this time a further aliquot fraction or the remainder of the test aliquot is subjected to culture, as is the culture vessel from which the test aliquot is removed. This culture of the separate aliquot/aliquot fraction and culture vessel may take place in the same or different systems. Additional testing on the cultured further aliquot fraction/remaining aliquot may then be performed as describe above, and the culture vessel containing the clinical sample may optionally be subjected to further culturing, e.g., in a separate system.

In yet another embodiment, a portion is removed from the first culture vessel after the period of preculture and introduced into a second culture vessel containing culture medium. A test aliquot is removed from the second culture vessel (step (c), and subjected to nucleic acid tests to identify a microorganism and/or to detect the presence or absence of one or more genetic antimicrobial resistance markers in the microorganism, and/or determining the antimicrobial susceptibility of a microorganism in the clinical sample. During this time the second culture vessel is cultured. A further aliquot may be removed from the second culture vessel and subjected to further testing as described above. The second culture vessel containing the sample aliquot and/or the first culture vessel may be subjected to further culturing, e.g., in a separate system.

It will be seen therefore that in certain preferred embodiments testing (e.g., molecular testing) takes place (i.e., the nucleic acid tests of step (e) according to the second aspect of the invention, or nucleic acid tests to identify a microorganism and/or to detect the presence or absence of one or more genetic antimicrobial resistance markers in the microorganism in the clinical sample according to the first aspect of the invention) without any further culture of the clinical sample (i.e., without any culture beyond the pre-culture which takes place within the transportation apparatus). In other embodiments, the testing (e.g., the molecular testing) may take place with a reduced period of further culture. In many microbial testing procedures as carried out today, identification tests (whether by conventional biochemical tests or by molecular tests) take place once there has been a positive result in a microbial culture, namely once microbial growth has been detected (a positive culture test). Thus, for example, a blood or other sample is introduced to a culture vessel (e.g., a blood culture flask), and this is cultured. The culture system may be designed or selected to indicate that (when) microbial growth has occurred, for example by including an indicator substance that yields a signal dependent on microbial growth (e.g., due to pH change, or conversion/consumption of a substrate, or generation of microbial metabolic product etc.) or simply by detecting microbial growth by any means. When/if sufficient microbial growth occurs to yield a signal/give detectable growth, this indicates a "positive" result in the culture/microbial detection (i.e., that there is growth of a microorganism in the clinical sample, although it is not known at this stage what is the identity of the microorganism). At this stage the identification and/or AST tests are usually performed. The microbial growth test may take some hours e.g., 6, 8, 10 or 12 hours or more, to perform.

The present invention has the advantage that a degree of microbial growth may take place prior to the point at which microbial culture would be initiated in a conventional micro-bial testing procedure as presently carried out. This may reduce the time between obtaining a clinical sample from a subject and obtaining a positive culture test, and may also reduce the time between obtaining a clinical sample from a subject and beginning to perform molecular testing to iden-tify the nature of the microorganism in the clinical sample. Furthermore, it is not necessary to wait until a positive result in a culture test has been obtained as a degree of microbial growth may take place in step (b), meaning that a microbial identification may be more rapidly obtained. Step (b) thus allows for a preculture step to take place during transpor-tation, e.g., before a first culture vessel is introduced into a culture apparatus and thus before a positive result may be achieved in a conventional culture test. Thus, in one repre-sentative embodiment according to the second aspect of the invention, steps (d) and (e) take place before there is a positive culture test result. In a further embodiment of this aspect, steps (d) and (e) are first performed before a positive culture result is obtained (or before the time that would be required to obtain a positive culture result) and may be repeated after a positive culture result (or the time period required for a positive result). In other words, in one preferred embodiment of this aspect of the invention at least one set of nucleic acid tests (step (e)) is performed before there is a positive culture result, or more particularly before the time that would be required for a positive culture result to be obtained. In a further representative embodiment of this aspect, step (f) (an AST step) may also be performed before a positive result is obtained or obtainable in a culture test. However, it is not precluded according to the method of this aspect of the present invention to perform the testing steps (e) and (f) after a positive culture result, e.g., to remove the test aliquot in step (c) after a positive test result. In such a case it can be seen that a preculture step (b) may involve culturing the first culture vessel until a positive culture test result is obtained or until such time as a positive culture test result would be expected.

Similarly, according to the first aspect of the invention, nucleic acid tests identify a microorganism and/or to detect the presence or absence of one or more genetic antimicrobial resistance markers in the microorganism, and/or determin-ing the antimicrobial susceptibility of a microorganism in the clinical sample take place before a positive culture test result. In a further embodiment of this aspect of the inven-tion, such tests are first performed before a positive culture result is obtained (or before the time that would be required to obtain a positive culture result) and may be repeated after a positive culture result (or after the time period required for a positive result. For example, at least one set of nucleic acid tests may be performed before there is a positive culture result, or more particularly before the time that would be required for a positive culture result to be obtained, and/or an AST assay may also be performed before a positive result is obtained or obtainable in a culture test. However, it is also contemplated nucleic acid tests identify a microorganism and/or to detect the presence or absence of one or more genetic antimicrobial resistance markers in the microorgan-ism, and/or determining the antimicrobial susceptibility of a microorganism in the clinical sample may take place after a positive result, i.e., a test aliquot is removed in step (c) after a positive test result. In such a case it can be seen that a preculture step (b) may involve culturing the first culture vessel until a positive culture test result is obtained or until such time as a positive culture test result would be expected.

In relation to the nucleic acid tests described herein (e.g., the tests of step (e) according to the second aspect of the invention), in one preferred embodiment a first set of nucleic acid probes are used which hybridize specifically to a nucleic sequence which is identificatory of a microorganism and a second set of probes which hybridize specifically to a nucleotide sequence which represents a genetic antimicro-bial resistance marker. In such an embodiment detection of probe hybridization may involve, or may take place by, probe amplification. Thus, detection of probe hybridization may be performed by detecting probe amplification. Accord-ingly, the methods of the invention may comprise (e.g., in step (e) according to the second aspect of the invention) the use of one or more amplification primers for the probe, that is primer(s) designed or selected for amplification of a probe which has hybridized to its target nucleotide sequence. As is described in more detail below, in a certain preferred embodiments the probe may be designed to be ligated if it has hybridized to its target nucleotide sequence, e.g., a ligation reaction designed to circularize the probe. Probe ligation is thus indicative of the presence of the target sequence. A ligated (e.g., circularized) probe may be detected by amplification of the ligated probe, for example by generating an amplification product using the ligated probe as template (e.g., a circularized probe may be a template for a RCA reaction) and the amplification product may be detected, either directly, or by using a detection probe which hybridizes to the amplification product.

The AST test (e.g., the test of step (f) according to the second aspect of the invention) may, as described further below, be performed in any convenient or desired way. Accordingly microbial growth may be assessed (or deter-mined) in the presence of different antimicrobial agents (e.g., antibiotics) and/or amounts or concentrations of anti-microbial agent (e.g., antibiotic). Growth may be assessed directly or by assessing (determining) markers of growth.

Accordingly, microbial growth may be assessed by deter-mining the amount of microbial cell matter (that is microbial biomass) present in a sample, particularly by assessing or determining this directly. In a preferred embodiment this is achieved by determining the amount of microbial biomass visually, and especially by imaging. In particular 2-D images may be obtained and assessed. Thus, in a preferred embodi-ment the area of microbial biomass may be determined (more particularly the area of microbial biomass in the field of view under investigation, e.g., in an image).

Microbial growth may be assessed by determining the amount of microbial cell matter (that is microbial biomass) present in a sample (here, specifically, in the test microbial cultures set up for the AST test) particularly by assessing or determining this directly. In a preferred embodiment this is achieved by determining the amount of microbial biomass visually, and especially by imaging. In particular, 2-D images aligned perpendicularly to the optical axis (here termed xy-aligned) may be obtained and assessed. A specific area of the specimen is covered in a single xy-aligned image the size of which is dependent on the optical properties of the imaging apparatus. For each position in xy-space, one or more 2D images can be collected at different intervals along the optical or z axis. Thus, a series, or stack of 2D images can be generated, providing 3D information of a sample volume. An alternative method of extracting 3D information from a sample is that employed by Unisensor (see e.g., U.S. Pat. No. 8,780,181), where the optical axis is tilted with respect to the xy-plane, and the sample or detector is moved along either the x or y plane. Here, a series of images with an extension into z space, in addition to xy space, is acquired. Through a subsequent transformation of the image data, stacks of 2D images aligned perpendicularly to the xy plane can be achieved also with this method.

Once extracted, the 3D information inherent in the 2D image stacks can be utilized to estimate/infer/deduce the total cell mass present in the analyzed volume. In a preferred embodiment, 2-D images may be generated from 3-D information by e.g., projections of z-stacks into one 2-D image. Analysis may then be performed using the resulting 2-D image. The area of microbial biomass may then be determined as the area of optical density indicating microbial biomass in the field of view under investigation, e.g., in the projected 2D image. Such a method is common practice in the art and may increase sensitivity, and algorithms for this for bright field images may be found in the publicly available software Cellprofiler™ from MIT, USA. Similar analysis may be performed for fluorescent images, and many alternative algorithms for this exist, e.g., in Cellprofiler,™, and also in most commercial image analysis systems.

In another embodiment, intensity variation in the z space stretching over each position in xy space is registered, indicating microbial mass in a specific position. Integrated over the entire xy space, this gives a measure of total microbial volume. Algorithms for this procedure also exist in commonly available image analysis software, e.g., in the freeware Cellprofiler™.

More generally, microbial growth may be assessed by determining the amount and/or number and/or size of microorganisms and/or microbial colonies or aggregates. As will be discussed in more detail below, in certain preferred embodiments, microbial growth is assessed (determined) by imaging, or alternatively expressed, by visualizing the microorganisms. Thus, microbial cells, which may include aggregates or clumps (clusters) of cells, or microbial colonies, may be visualized or imaged as a means of determining (or assessing or monitoring) growth. This may include counting of cells or colonies, but is not limited to such methods and includes any means of visually assessing the amount of microbial growth by assessing (or determining) the size, area, shape, morphology and/or number of microbial cells, colonies or aggregates (the term "aggregate" includes any collection of cells in physical proximity e.g., a clump or cluster; this may include non-clonal clumps/ clusters of cells which have aggregated or stuck together (e.g., neighboring cells which have become aggregated) as well as clonal colonies). The parameter used to measure microbial growth may, but need not, vary according to the identity of the microbe (e.g., as determined in step (e) according to the second aspect of the invention) and the antimicrobial agents used in the AST assay (e.g., step (f) according to the second aspect of the invention). Indeed, depending on the organism and the antimicrobial agents used, the morphology or growth pattern of the cells may be affected, and this may be altered or changed from the "normal" or "typical" morphology or growth pattern, e.g., in the absence of the antimicrobial agent. Whilst some AST growth monitoring methods may depend on detecting such changes, it is not essential according to the present invention to take such changes into account and the amount (e.g., area) of microbial growth or biomass may be determined irrespective of morphology and/or growth pattern. Thus, the same growth monitoring method may be used regardless of the microbial cell and/or antimicrobial agents used. Methods for performing the AST test are described further below.

According to the second aspect of the invention, advantageously, the clinical sample (e.g., a test aliquot) may be used directly in the AST test, after a positive result in step (e). The clinical sample/portion/test aliquot/aliquot fraction etc. would have been subjected to culture during the time that steps (d) and (e) have been performed, and it is not necessary for any further sub-culture to be performed before step (f). Indeed, in advantageous embodiments there is no further sub-culture step. In particular there is no sub-culture step in a further culture medium or culture vessel. More particularly, there is no step of sub-culturing to obtain a pure culture of a microorganism prior to AST. This means that a more rapid AST test may be performed.

Analogously to this, according to the first aspect of the invention, an AST test may be performed directly using the clinical sample (e.g., the test aliquot), and it is not necessary for any sub-culture to be performed prior to this. Indeed, in advantageous embodiments there is no further sub-culture step. In particular there is no sub-culture step in a further culture medium or culture vessel. More particularly, there is no step of sub-culturing to obtain a pure culture of a microorganism prior to AST. This means that a more rapid AST test may be performed.

Advantageously, a rapid AST test is performed. Accordingly, in preferred embodiments of the methods of the present invention, the AST test (e.g., the AST test of step (f)) may give a result in 8, 7, or 6 hours or less, for example in 4 or 5 hours or less.

The monitoring or assessing of microbial growth in the AST test may take place by monitoring growth continuously or at intervals over a time period (e.g., up to 6, 5, 6, 7 or 8 hours), or by comparing growth at the time the AST growth culture is initiated (to) with growth at a later time point (e.g., at up to 4, 5, 6, 7, or 8 hours), or indeed comparing growth at two or more different time points. In preferred embodiments, microbial growth is determined at more than one time point, i.e., at least two time points.

The method of the invention may be used for the detection and characterization of any microorganism. Generally speaking, clinically relevant microorganisms are concerned. As used herein, the term microorganism encompasses any organism which may fall under the category of "microorganism". Although not necessarily so, microorganisms may be unicellular, or may have a unicellular life stage. The microorganism may be prokaryotic or eukaryotic and generally will include bacteria, archaea, fungi, algae, and protists, including notably protozoa. Of particular interest are bacteria, which may be Gram-positive or Gram-negative or Gram-indeterminate or Gram-non-responsive, and fungi.

Particularly, clinically relevant genera of bacteria include *Staphylococcus* (including Coagulase-negative *Staphylococcus*), *Clostridium, Escherichia, Salmonella, Pseudomonas, Propionibacterium, Bacillus, Lactobacillus, Legionella, Mycobacterium, Micrococcus, Fusobacterium, Moraxella, Proteus, Escherichia, Klebsiella, Acinetobacter, Burkholderia, Enterococcus, Enterobacter, Citrobacter, Haemophilus, Neisseria, Serratia, Streptococcus* (including Alpha-hemolytic and Beta-hemolytic *Streptococci*), *Bacteroides, Yersinia*, and *Stenotrophomas*, and indeed any other enteric or coliform bacteria. Beta-hemolytic *Streptococci* would include Group A, Group B, Group C, Group D, Group E, Group F, Group G and Group H *Streptococci.*

Non-limiting examples of Gram-positive bacteria include *Staphylococcus aureus, Staphylococcus haemolyticus, Staphylococcus epidermidis, Staphylococcus saprophyticus, Staphylococcus lugdunensis, Staphylococcus schleiferei, Staphylococcus caprae, Staphylococcus pneumoniae, Staphylococcus agalactiae, Staphylococcus pyogenes, Staphylococcus salivarius, Staphylococcus sanguinis, Staphylococcus anginosus, Streptococcus pneumoniae, Streptococcus pyogenes, Streptococcus mitis, Streptococcus* agalactiae, Streptococcus anginosus, Streptococcus equinus, Streptococcus bovis, Clostridium perfringens, Enterococcus faecalis, and Enterococcus faecium. Non-limiting examples of Gram-negative bacteria include Escherichia coli, Salmonella bongori, Salmonella enterica, Citrobacter koseri, Citrobacter freundii, Klebsiella pneumoniae, Klebsiella oxytoca, Pseudomonas aeruginosa, Haemophilus influenzae, Neisseria meningitidis, Enterobacter cloacae, Enterobacter aerogenes, Serratia marcescens, Stenotrophomonas maltophilia, Morganella morganii, Bacteroides fragilis, Acinetobacter baumannii and Proteus mirabilis.

Clinically relevant fungi may include yeasts, particularly of the genus Candida, and fungi in the genera Aspergillus, Fusarium, Penicilium, Pneumocystis, Cryptococcus, Coccidiodes, Malassezia, Trichosporon, Acremonium, Rhizopus, Mucor and Absidia. Of particular interest are Candida and Aspergillus. Non-limiting examples of fungi include Aspergillus fumigatus, Candida albicans, Candida tropicalis, Candida glabrata, Candida dubliensis, Candida parapsilosis, and Candida krusei.

The term "detecting" refers broadly to any means of determining the presence or absence of a microorganism. Thus "detecting" may include determining, assessing or measuring in any way or form whether or not a microorganism is present—it may include qualitative, quantitative or semi-quantitative determinations.

The term "characterizing" means broadly any means of determining information about the nature and/or properties of the microorganism, and includes particularly identifying the microorganism. More particularly the microorganism may be identified in terms at least of its genus, and preferably its species. In some cases, even identification at the level of strain may be possible. The method of the invention also advantageously allows the microorganism to be characterized in terms of determining whether or not it is susceptible, or is expected to be susceptible, to given antimicrobial agents, or whether it demonstrates resistance or is expected to be resistant to any antimicrobial agents e.g., determining its antimicrobial susceptibility profile. This may be done by testing for the presence of molecular resistance markers, namely genetic variants or particular genetic sequences which are associated with, or indicative of resistance to one or antimicrobial agents, or classes of antimicrobial agent. Such molecular tests of course do not determine conclusively that the microorganism is susceptible and this is done by an AST test, such as the AST test of step (f) in the second aspect of the invention, in which the effect of the antimicrobial agent on the growth of the microorganism is tested directly.

The term "lysing" means breaking down of a cell. In particular, the cell is broken down to release cell contents, including particularly nucleic acid. This may be achieved by any means, as vast number of which are known in the art, for example n by viral, enzymatic, mechanical, electrical, chemical, heat, cold or osmotic mechanisms that compromise its integrity leading to the partial or full release of cellular components into surrounding solution.

The clinical sample may be any clinical sample that may be obtained from a test subject, which generally will be a human patient but may be any human or animal, generally mammalian, subject. It may thus be any sample of body tissue, cells or fluid, or any sample derived from the body, e.g., a swab, washing, aspirate or rinsate etc. Suitable clinical samples include, but are not limited to, blood, serum, plasma, blood fractions, joint fluid, urine, semen, saliva, feces, cerebrospinal fluid, gastric contents, vaginal secretions, mucus, a tissue biopsy sample, tissue homogenates, bone marrow aspirates, bone homogenates, sputum, aspirates, wound exudate, swabs and swab rinsates e.g., a nasopharyngeal swab, other bodily fluids and the like. In a preferred embodiment, the clinical sample is sample is blood or a blood-derived sample, e.g., serum or plasma or a blood fraction.

The microorganism may be any microorganism, in particular any pathogenic microorganism or any microorganism causing an infection in the body, and thus the method may be used in the context of detecting or diagnosing a microbial infection in or on any part of the body of a test subject (i.e., any microbial infection) and the nature of the clinical sample may be determined accordingly, e.g., according to the presentation of symptoms of the infection or suspected infection, or the general clinical condition of the subject. Although any microbial infection is encompassed, the method of the invention has particular utility in the detection or diagnosis of sepsis, or where sepsis is suspected. Thus, the clinical sample may be from a subject having, or suspected of having, or at risk of, sepsis. In such a case the sample will generally be blood or a blood-derived sample. Typically, the sample will be blood.

In the first step of the method (step (a)) the sample is introduced to a first culture vessel. This is a standard step which may be carried out according to standard procedures well known in the art and widely described in the literature. The first culture vessel may be any vessel or container suitable for the collection of a clinical sample and culture of microbial cells, e.g., a tube, bottle, flask etc. Preferably, the first culture vessel is a blood culture flask. Blood culture flasks are well-known in the art, and may be, for example a BacT/ALERT™ (Biomerieux) blood culture flask, a Bactec™ blood culture flask (Becton Dickinson) or Versa-Trek™ blood culture flask (Thermo Fisher), or indeed any tube, flask or bottle known for the sampling of blood, particularly for the purpose of culture to detect microorganisms.

The second culture vessel, i.e., where a portion of the clinical sample culture is removed from the first culture vessel prior to step (c) can include any vessel or container suitable for the culture of microbial cells, e.g., a plate, well, tube, bottle, flask etc. The second culture vessel may conveniently also be a blood culture flask as described above.

Conveniently the culture vessel (e.g., the first or second culture vessel) may be provided with the culture medium already contained therein. However, the culture medium may be separately provided and introduced into the culture vessel, either prior to, simultaneously with, or after the clinical sample has been added.

The culture medium may be any suitable medium and may be selected according to the nature of the clinical sample and/or the suspected microorganism, and/or clinical condition of the subject etc. Many different microbial culture media suitable for such use are known. Typically, the culture medium may contain sufficient nutrients to promote rapid growth of microorganisms, as is known in the art. In many cases appropriate media are complex growth media comprising media such as tryptic soy broth, Columbia broth, brain heart infusion broth, Brucella broth, as well as general purpose growth media known in the art, and may include the addition of particular growth factors or supplements. Culture media are available in various forms, including liquid, solid, and suspensions etc. and any of these may be used, but conveniently the medium will be a liquid medium. Where the culture vessel is a ready to use blood culture flask, as described above, these vessels may contain specified media especially modified to allow a wide range of microorganisms to grow. Typically, medium supplied in a blood culture flask by a manufacturer will contain an agent or additive to neutralize the presence of any antibiotics present in a clinical sample taken from a test subject. Flasks containing or not containing such neutralizing agents may be used, and neutralizing agents may be added to the culture vessel if desired.

As noted above, a first test aliquot for the identification tests of step (e) may be removed following a period of pre-culture during transport of the clinical sample.

Step (b) comprises pre-culturing the clinical sample in the first culture vessel during transit, and allows the microorganisms present in the sample to grow (i.e., multiple), before the molecular testing takes place. In the case of a blood sample for example (e.g., in a blood culture flask), the number microbial cells is generally expected to be low and thus the pre-culture is advantageous to increase the number of microbial cells available for molecular testing or to facilitate the recovery of microbial DNA etc.

In certain embodiments of the present invention, it may be beneficial to detect or measure whether microbial growth has occurred during the pre-culture of the clinical sample, e.g., prior to introducing the first culture vessel into the clinical sample processing system and/or prior to removing a test aliquot for molecular testing. Microbial growth may be detected using any convenient method as described herein, including turbimetric measurement, colorimetric determination, light detection, light scattering, pH measurement, spectroscopic measurements and fluorometric detection.

Removal of the test aliquot in step (c) may take place by any convenient means, depending on the nature of the culture vessel and how it is incubated. For example, in the case of a blood culture flask an aliquot may simply be withdrawn using a needle and syringe. According to normal clinical and microbiological practice steps may be taken to avoid or limit contamination, e.g., this may be done under aseptic conditions. For example, the septum of a culture vessel, such as a blood culture flask, may be cleaned or decontaminated, preferably prior to withdrawing an aliquot, and/or after withdrawing an aliquot.

In one convenient embodiment, the means for removal of the test aliquot (e.g., the needle, and optionally the syringe, may be provided in single-use form, i.e., as a consumable. In other words, it may be disposable and not re-used.

Step (c) of removing a test aliquot while continuing to culture may be performed more than once. Indeed, for performing the molecular tests of step (e) and the AST test of step (f) according to the second aspect of the invention, two separate aliquots will usually be taken and in each case culture will be continued. As mentioned above, however, a portion of the aliquot taken for performing the molecular tests may be retained and cultured. This portion may be used for repeat molecular tests (e.g., at a second time point) and/or may be used in the AST test. However, separate aliquots for repeat molecular tests may also be taken, for example at spaced intervals of time. Thus, a molecular test (step (e) may be performed more than once. In one such embodiment, an aliquot may be removed straight after step (b)(i) for an initial molecular test to be performed following transport of the clinical sample (i.e., upon arrival of the clinical sample at a laboratory for testing, or when the clinical sample is selected for testing). If the initial molecular test is negative or not fully conclusive for example, a second aliquot may be removed after a period of preculture to carry out a second molecular test. Thus, in one embodiment, a method according to the second aspect of the invention may comprise the following steps:

i) introducing a clinical sample to a culture vessel;

ii) simultaneously transporting and incubating the clinical sample, wherein said transporting and incubating comprises placing the culture vessel in a thermally insulated compartment of a sealable container, heating the clinical sample to a temperature suitable for pre-culturing of the sample, wherein the thermally insulated compartment and the heating are used to keep the clinical sample at the temperature suitable for pre-culturing during transport of the sample and optionally mechanically agitating the culture vessel to thereby agitate the sample during transport, thereby to pre-culture the clinical sample;

iii) removing a test aliquot from said culture vessel, iv) separating DNA from said test aliquot and performing nucleic acid tests as described in step (e) above;

v) whilst step (iv) is on-going culturing said clinical sample in said culture vessel;

vi) removing a further test aliquot from said culture vessel, and continuing to culture said clinical sample in said culture vessel;

vii) separating DNA from said further test aliquot and performing nucleic acid tests as described in step (e) above;

If this second (or any further) molecular test is negative the culture vessel may undergo further culture. Thus, culturing of the culture vessel may be continued to allow further tests to be performed.

Similarly, in an embodiment of the first aspect of the invention, a portion of the test aliquot taken for performing a molecular test (e.g., a nucleic acid test) may be retained and cultured, and the retained portion may be used for repeat molecular tests (e.g., at a second time point). However, separate aliquots for repeat molecular tests may also be taken, for example at spaced intervals of time. Thus, a molecular test may be performed more than once, e.g., once following step (b)(i) of the first aspect of the present invention, and at a further time point after a period of culture. According to this embodiment, the method comprises steps (i)-(iii) outlined above and a step of separating DNA from the test aliquot and performing a nucleic acid test, and whilst this step is on-going culturing the clinical sample in the culture vessel. Following this period of culture, a further test aliquot may be removed from said culture vessel (and optionally culture of the clinical sample in the culture vessel is allowed to continue), and DNA is separated from the further test aliquot and a nucleic acid test is performed as described above To enable a molecular nucleic acid test (e.g., the molecular nucleic acid tests of step (e) of the second aspect of the invention) to be performed, DNA is separated from the removed aliquot or aliquot fraction (in step (d)). It will be understood of course that microbial DNA is required for the molecular tests and depending on the nature of the clinical sample there may be a significant number of cells from the test subject present, which may complicate or interfere in the separation or subsequent testing. More particularly the non-microbial DNA, e.g., human DNA, present in the cells of the test subject in the clinical sample may make the detection and testing of microbial DNA difficult, particularly in the case of samples such as blood where there are very many more blood cells (particularly white blood cells) than microbial cells. Accordingly, it may be desirable to selectively separate, or enrich for, microbial DNA from the test aliquot. Indeed, the method may optionally comprise a step of separating or enriching microorganisms or microbial cells in or from the test aliquot, e.g., prior to or concurrently with the step of separating DNA, or separating microbial DNA.

Suitable methods for enriching the microorganisms in the sample can include lysing any non-microbial cells present in the aliquot, or selectively removing microbial cells from the aliquot (i.e., positive or negative selection of microbial cells from the aliquot). Methods for doing this are known in the art. Methods for selectively lysing non-microbial cells for selectively enriching microorganisms in a sample, which are not dependent on knowing the identity of the microorganisms, are described for example in US 2013/0171615, US 2012/0231446, US 2010/0184210, U.S. Pat. Nos. 7,893,251 and 8,481,265, and methods for selectively removing eukaryotic cells from a sample are described in US 2005/0202487.

Methods for separating DNA are known in the art, and any of the various different methods known and described may be used. Generally speaking, these involve lysing cells, which may be done by various means and ways, and recovering the released DNA, and again various means and procedures for this are known and available and any of these can be used. The lysis step may depend on the nature of the suspected microorganisms, although many procedures may lyse microorganisms in general.

As mentioned above, depending on the nature of the sample, preferably this step involves separating microbial DNA, more particularly selectively separating, or enriching for, microbial DNA. This may generally be done by selectively lysing test subject cells in the sample, whilst leaving the microbial cells intact. Many procedures, and indeed kits, are known and available which can achieve this, for example from Molzym (Germany). For example, human cells, e.g., human blood cells, may readily be lysed, without lysing microbial cells present in the aliquot. The same applies to other human or mammalian cells which may be present, depending on the sample. Separation, and in particular selective separation, of microbial DNA is preferred in the case of a blood or blood-derived sample.

Thus, any cells in the clinical sample which derive from the subject under test and which are present in the test aliquot may be lysed using lysis conditions which do not lyse microbial cells. For example, an appropriate lysis reagent, e.g., a lysis buffer, may be added to the test aliquot. The DNA, or nucleic acid more generally, released in this first lysis step may be removed, for example by degradation (e.g., with a DNA-degrading enzyme e.g., DNase), and/or by any method which can separate or remove DNA or nucleic acid from the sample and/or separate any non-lysed microbial cells, e.g., a separation method such as filtration, column separation, precipitation, centrifugation etc., although in one embodiment it is preferred feature of the method that it does not include centrifugation. Thus, in one embodiment the step of DNA separation does not include centrifugation, and indeed in a further preferred embodiment the method as a whole does not include centrifugation. Any enzymes, particularly any DNA-degrading enzymes, used in these steps may be inactivated or removed, e.g., by heating or by adding further protein-degrading enzymes.

Next, microbial cells remaining in, or from, the treated aliquot (e.g., the lysate from the first lysis step) are then lysed by introducing lysis conditions, e.g., adding an appropriate lysis reagent (e.g., lysis buffer) for lysis of microbial cells. Many such buffers are known in the art and/or commercially available e.g., from Molzym (Germany). Microbial DNA released in the second microbial lysis step may then be recovered, e.g., separated from the reaction mixture (lysate). As above, many techniques for this are available and any of these may be used. In a preferred embodiment this step does not include centrifugation.

The recovered DNA, or recovered microbial DNA, is then subjected to the molecular tests (e.g., in step (e)). It may be desirable to denature double-stranded DNA, particularly microbial DNA separated or enriched from the test aliquot, prior to performing the molecular nucleic acid tests of step (e). Further it may be advantageous or desirable (but is not necessary) to fragment the DNA prior to performing the molecular tests of step (e). Such steps may be achieved by routine methods known in the art, for example fragmentation may be achieved mechanically, by heat or by enzymatic degradation methods, e.g., using restriction or other endonucleases.

Essentially the molecular tests use nucleic acid probes or primers which are designed to hybridize to specific microbial nucleic acid sequences, or to be capable of selectively amplifying a specific microbial sequence, and which, based on whether or not they hybridize, or are extended (e.g., successfully prime an amplification reaction) can be used to detect whether or not a particular microorganism is present and whether or not it contains a genetic antimicrobial resistance marker. Such nucleic acid tests, and hybridization probes or primers for use in them, are known in the art and described in the literature.

A hybridization probe will comprise a nucleotide sequence which is capable of hybridizing to a desired or selected target sequence, preferably specifically hybridizing. Thus, it may comprise a sequence which is complementary to a target sequence. Absolute or 100% complementarity is not required as long as the probe is capable of hybridizing specifically to the target sequence in the presence of non-target nucleotide sequences. By detecting hybridization, it can be detected whether or not the target sequence is present, and many hybridization assay formats using different modalities for detecting hybridization of a nucleic acid probe are known and may be used. Generally speaking, the detection of step (e) may take place by detecting the hybridization probe.

As discussed above, detection of the hybridization probe may comprise or involve amplifying the hybridization probe. Accordingly, in addition to hybridization probes, one or more amplification primers for the hybridization probes may be provided.

In the case of the invention the target sequence is firstly (e.g., in step (e)(i) according to the second aspect of the invention, or step (i) of the nucleic acid test according to the first aspect of the invention) a nucleotide sequence identificatory of a microorganism, that is, a nucleotide sequence which is characteristic of a particular microorganism, e.g., of a genus, species or strain and which may be used as the basis for identifying that microorganism. Thus, the identificatory nucleotide sequence may accordingly be viewed as a motif or signature, or sequence characteristic of a given particular microorganism. Typically, it may be a sequence which is unique to that microorganism (e.g., at genus, species or strain level). A number of such identificatory sequences have been identified and reported and any of these could be used. For instance, the target sequence may be a nucleic acid sequence from the 16s rRNA gene. Alternatively, it would be a routine matter to identify such motif/signature/identificatory sequences, e.g., using bioinformatic tools to analyze microbial genomic sequences, and to design appropriate hybridization probes based on these, comprising sequences capable of hybridizing to the identified sequences.

Alternatively, rather than using hybridization probes, one or more primers may be used and a primer-based method, for example a polymerase primer extension-based method, may be used to detect and identify the microorganism. Typically, this will be an amplification method, most commonly PCR, but other amplification methods or primer extension methods may be used, including e.g., LCR, NASBA, MDA etc. A primer or set of primers may hybridize to the identificatory nucleotide sequence, or it (they) may hybridize in such a manner (e.g., flanking it) that an identificatory sequence may be amplified. The term "amplified" is used broadly in this context (see also above) to mean any method of providing a copy (including a complementary copy) of the identificatory or marker sequence and includes simple primer extension reactions, and linear as well as exponential amplification. For PCR, a primer pair will be used for each microbial identificatory sequence.

Put more simply, the hybridization probes or primers for use in the invention may be specific for (i) a nucleotide sequence which is identificatory of a microorganism or (ii) a nucleotide sequence representing a genetic antimicrobial resistance marker.

Thus, alternatively defined, in the method of the invention as set above, step (e) of the second aspect of the invention, or the nucleic acid test performed according to the first aspect of the invention may be expressed as follows:

performing nucleic acid tests on said DNA to identify the microorganism and to detect the presence or absence of one or more genetic antimicrobial resistance markers in said microorganism, wherein said nucleic acid tests are performed using:

i) one or more nucleic acid probes and/or primers for microbial identification, each said probe and/or primer being specific for a nucleotide sequence which is identificatory of a given microorganism; and ii) one or more nucleic acid probes and/or primers for antimicrobial resistance marker detection, each said probe and/or primer being specific for a nucleotide sequence representing a genetic antimicrobial resistance marker;

and it is detected whether or not said probes or primers have hybridized to said DNA and/or said primers have been extended (e.g., an amplification reaction has taken place).

As noted above, the detection step may comprise or involve amplifying a probe after it has hybridized to its target nucleotide sequence. As described in more detail below, amplification may be designed to be dependent on hybridization. Thus, only a probe which has hybridized may be amplified.

In this way a set or panel of hybridization probes or primers can be assembled and/or constructed which are capable of hybridizing to, or amplifying, the nucleic acids of selected microorganisms and thereby detecting whether or not that microorganism is present in the test aliquot (and thereby sample). By detecting which microorganism is present (i.e., which identification probe hybridizes or which primer/primer set is extended or primes an amplification reaction), it may be identified which microorganism is present in the sample. By way of example the hybridization probes or primers for microbial identification may comprise probes or primers each capable of specifically identifying one of a selected set of microorganisms, e.g., the major or most common known sepsis pathogens. For example, the lists of specific bacterial and fungal species provided above represent approximately 95% of the most common sepsis pathogens and may constitute a representative microorganism panel according to the invention.

Accordingly, in step (i) above (e.g., step (e)(i)) a multiplicity of identification probes and/or primers (or primer sets) will advantageously be used. A multiplicity is broadly defined herein as two or more, or more particularly, 3, 4, 5, 6, 7, 8, 9, 10, 15, 20, 30, 40, 50, 60, 70, 80, 100, 200, 300, 400 or 500 or more. As well as multiple different microorganisms for identification, different probes or primers/primer sets may be used for a given microorganism to be detected, e.g., 2, 3, 4 or 5 probes or primers, or more per target microorganism. Since a panel of microorganisms may include at least 10, 15, 20, 25, 30, 40, 50 or more (e.g., up to 60, 70, 80, 90 or 100 microorganisms, typically a panel or set of at least 30 or more, e.g., 50, 70, 80, 100, 200, 300, 400 or 500 or more identification probes or primers (or primer sets) will be used. According to procedures known in the art, probe or primer-based nucleic acid test may use thousands, or many tens or thousands, of probes or primers in multiplex and such procedures are encompassed by the present invention.

Secondly, in step (ii) above (e.g., step (e)(ii)) of the methods described herein, the target sequence for the hybridization probes or primers is a nucleotide sequence which is an antimicrobial resistance marker. A number of such markers have been identified and reported in the art and hybridization probes/primers to detect them have been devised. Any of these could be used or alternatively further probes or primers may be designed based on such identified marker sequences. Further, additional marker sequences may be identified by routine screening methods. An antimicrobial resistance marker may be a nucleotide sequence which codes for a component of a resistance mechanism e.g., an enzyme or a modified protein, or it may simply be a nucleotide sequence or sequence variant which has been identified to associate with resistance to an antimicrobial agent.

By way of example, β-lactamases represent an important mechanism of resistance against antibiotics for bacteria and are responsible for resistance to certain antibiotic classes. The emergence of bacteria capable of forming extended spectrum β-lactamases (ESBL-forming bacteria). ESBL represents a recent example of a rapidly developing resistance problem. Probes have been reported capable of identifying highly diverse β-lactamases (Barisic et al, 2013, Diagnostic Microbiology & Infectious Disease, 77(2), 118-125). Other known genetic resistance markers include mecA, mecC, vanA, vanB, CTX-M, KPC, VIM, NDM, and OXA-48. Ciprofloxacin resistance mutations have been identified e.g., in antibiotic-resistant *F. tularensis, B. anthracis*, and *Y. pestis*, and are available.

Hybridization probes may take various forms, and at their simplest comprise a nucleotide sequence capable of hybridizing to the target sequence and a further sequence or moiety by which they may be detected, directly or indirectly. Thus, such a probe may be provided with a directly or indirectly detectable label, e.g., a spectrophotometrically (e.g., fluorescently) detectable label, or a reporter molecule or moiety which may take part in a signal-giving or signal generating reaction e.g., an enzyme, or enzyme substrate or co-factor, or which may be an affinity tag by which the probe may be selectively labelled or selectively isolated or separated after the hybridization reaction. Different forms of labelling and labelled nucleic acid probes are widely known and reported e.g., molecular beacons and other FRET based probes. However, rather than directly detecting the presence of a hybridized probe by means of a label or reporter moiety provided in or on the probe, the probe may be detected indirectly, for example by detecting an amplification product to the probe. Different hybridization probe formats are known and any of these may be used, for example, molecular inversion probes, scorpion probes and padlock probes.

Molecular inversion probes and padlock probes for example are designed to be circularized by ligation following hybridization to their target sequence, and the resulting circularized probe may be detected by amplification, e.g., by RCA.

Padlock probes represent a preferred type of hybridization probe according to the present invention. Padlock probes were initially described in 1994 (Nilsson et al, 1994, Science, 265, 2085-2088) and have since been developed and widely used in the detection of various nucleotide sequences, and indeed more widely as reporters in the assay of wide range of molecules (see e.g., EP0745140, EP0964704, EP0951565 and Hardenbol, et al. 2003. Nat. Biotechnol. 21, 673-678). Padlock probes comprise sequences at their 5' and 3' ends that can hybridize to a target nucleotide sequence. In one embodiment, the 5' and 3' ends of the padlock probes can hybridize to said nucleotide sequence so that they are directly adjacent to each other. In another embodiment the 5' and 3' ends of the padlock probes can hybridize to said nucleotide sequence so that they are not directly adjacent to each other and the intervening gap may be filled in, either by polymerase extension of the hybridized 3' end, or by a gap-filling oligonucleotide. The ends are then ligated together to form a nucleic acid circle which can subsequently be detected, conveniently by rolling circle amplification (RCA)-based methods. The dual recognition (two target hybridizing regions) as well as the requirement for ligation means that padlock probes are highly specific and well suited to detecting unique sequences in a complex genomic background. The uni-molecular circularization approach and the RCA-based detection of the circularized probes both lend themselves well to multiplexed detection, and a large number of probes may be used in combination and amplified together without problems of interference.

However, although RCA is a preferred method for detecting a circularized padlock probe, the invention is not limited to this and other amplification methods, including e.g., PCR, or other detection methods e.g., based on selectively detecting circular as opposed to linear nucleic acids, may be used.

Strand-displacing polymerase enzymes suitable for RCA are known, e.g., CD-29 polymerase.

Amplification of a circularized padlock probe by RCA leads to the formation of a concatemeric RCA product comprising several hundreds of repeats of the complement of the padlock probe sequence. In one embodiment of the present invention an RCA product may be detected by hybridization of fluorescently-labelled detection oligonucleotides.

Since the RCA reaction is linear, and thus has slow amplification power, a number of methods have been developed which may enhance amplification and increase the signal from an RCA reaction, including for example hyper-branched RCA methods as described by Lizardi (U.S. Pat. Nos. 6,183,960 and 6,143,495). Any of these may be used. The RCA product can also be amplified further by PCR, or indeed any other method of nucleic acid amplification or any signal amplification method may be used.

A particularly useful method for enhancing RCA amplification is Circle-to-Circle Amplification (C2CA). This is described in Dahl et al, 2004, PNAS USA, 101, 4548-4553 and WO 03/012199. C2CA involves cleaving the concatemeric rolling circle amplification product (RCP) from a first RCA reaction into monomers (e.g., each corresponding to a tandem repeat of the concatemer, i.e., a complementary copy of the circularized padlock probe) and then recircularizing the monomers, each into a further circle which may be used as the template in a further RCA reaction (i.e., a further round of RCA). This may be repeated one or more times. The repeat RCAs lead to amplification of the signal.

Cleavage of the RCP may be achieved by hybridizing an oligonucleotide to a sequence (restriction site sequence) present in each repeat (monomer) of the RCA product to create a double-stranded restriction cleavage or recognition site and cleaving with a restriction enzyme to cleave the product into monomers. The same oligonucleotide, e.g., added in excess, may be used as the ligation template for circularization of the monomers released by the cleavage. A denaturation step may be included after cleavage to release single stranded monomers, which are available for hybridization to excess uncleaved or added oligonucleotide.

A modification of the C2CA reaction is described in our co-pending application UK patent application No. 1321123.0 filed on 29 Nov. 2013, herein incorporated by reference. In this modified C2CA procedure the efficiency of the second or any subsequent round of RCA is improved by reducing the size of the circularized monomers, such that the circular template for the second round of RCA is reduced in size as compared to the first RCA template (here the circularized padlock probe), and thereby the speed of the second (and subsequent) RCA reactions may be increased. Various means of cleaving the RCP such that the released monomers are reduced in size or for otherwise effecting a size reduction step on the monomers are described in the co-pending application.

Other ways of amplifying the signal from an RCA reaction by performing a second RCA reaction have also been reported and any of these may be used. One such method is the so-called superRCA (sRCA) method of Olink AB described in WO 2014/076209. In this procedure a second RCA reaction is performed, which is dependent upon a first RCA reaction, but which does not amplify the first RCA product. The second RCA product remains physically attached to the first RCA product, in order that the signal from the second RCA product is localized to the first RCA product. By utilizing an RCA primer which is hybridized (directly or indirectly) to the first RCA product to amplify a second RCA template circle, a second RCA product may be generated by extension of the RCA primer, which, by virtue of hybridization of the primer, is hybridized, and hence attached to the first RCA product. Since the first RCA product is a concatemer comprising tandem repeat complementary copies of the template circle for the first RCA reaction, the RCA primer for the second RCA will bind to repeated copies of its cognate primer-binding sequence, repeated throughout the first RCA product. In other words, the first RCA product will comprise repeated binding sites for the RCA primer for the second RCA, one in each of the tandem repeats ("monomers" of the concatemer). Each such primer can prime a second RCA reaction, leading to increased, more than linear, amplification.

The RCP of an RCA or C2CA reaction may be detected directly, as indicated above, e.g., by means of labelled detection oligonucleotides which can hybridize to sequences in the tandem repeats in the RCP or by incorporating labelled nucleotides into the RCP, or monomers released from an RCP may be detected.

An RCP, being a very long nucleic acid concatemer (typically comprising 500-1000 copies of the template circle sequence), collapses into a random-coiled amorphous "blob" or ball of DNA, which can readily be detected, and indeed visualized. Thus, such blobs may be imaged or detected microscopically or by any other convenient means, to detect (indirectly) hybridization of the padlock probes to their targets (and their subsequent ligation and detection by RCA/C2CA). Other means of detecting the RCP also exist, for example by flow cytometry, or by capturing the RCP on a solid support and detecting it by means of labelled detection oligonucleotides or other labelling means, e.g., incorporated labelled oligonucleotides or nucleic acid stains or dyes etc.

Detection of an RCP blob provides a convenient means of amplified single molecule detection (ASMD), The use of such a method based on C2CA and counting of RCP blobs to detect bacteria and spores is described by Göransson et al., 2012 PLOS one, 7(2), e31068 and such a method may be used according to the present invention. The concentration, or enrichment, of the label in the RCP blob means that there is a high concentration of label in the blob as compared to the surrounding solution. This eliminates the need for washes and enables homogenous methods to be used—reaction products can readily be detected in a flow cell, for example as described by Jarvius et al., 2006, Nature Methods, 3, 725-727.

Alternatively, rather than detecting the RCP concatemer as such, the RCP can be cleaved into monomers and the monomers may be detected. Again, this may be by means of label incorporated directly into the monomers, or by hybridizing detection oligonucleotides to the monomers, e.g., as described above, or according to principles well known in the art. For example, monomers may be bound onto a microarray and the array-bound (hybridized) monomers may be detected by hybridization of labelled detection oligonucleotides. Thus, an array may be provided which carries (e.g., by depositing on) oligonucleotides that are capable of binding to (hybridize) to the RCP monomers. The array oligonucleotides can be designed to be complementary to the RCP monomers and may be covalently coupled to the array substrate via amine, thiol or epoxide groups or by any known coupling chemistry, or they may be synthesized in situ on the array using known techniques e.g., photolithography. Such an array can then be scanned or imaged and analyzed, again according to methods well known in the art. Thus, it can be detected whether or not a particular padlock probe was hybridized to its target and therefore ligated and amplified, by detecting whether or not a particular RCP monomer has been hybridized to the array.

Thus, in certain embodiments of the present invention, solid phase-based methods may be used. A solid support may be employed in carrying out various stages or steps of the method. For example, as well as or alternatively to the possible array detection of RCP monomers discussed above, a solid phase may be used in earlier steps of the method. In one such embodiment the target DNA from or in the DNA separated from the test aliquot for use in molecular testing may be immobilized on a solid support. Thus, DNA fragments or DNA molecules which may comprise the nucleotide sequences which are the targets for the molecular tests to be carried out (e.g., in step (e) according to the second aspect of the invention), may be selectively captured from the separated DNA (e.g., of step (d) according to the second aspect of the invention) using capture probes, e.g., prior to or at the same time as the molecular testing. Capture probes may be used which hybridize to the target DNA (at sites distinct from the hybridization sites for the nucleic acid identification and resistance detection probes or primers). The capture probes may be added to the separated or enriched DNA, e.g., prior to or at the same time as the identification and resistance detection probes or primers. The capture probes may be immobilized or provided with means for immobilization such that they may be immobilized after binding to the target DNA. Such means for immobilization may include for example an affinity molecule capable of binding to its cognate binding partner, provided on a solid support. By way of representative example, the capture probe may be biotinylated, for binding to streptavidin or avidin (or a variant thereof) which is coupled to the solid support. Any convenient solid support may be used, as known in the art. For example, a solid support can include a microarray, blotting membrane, gel, microscope slide, well, tube or other container or vessel, or a bead or particle, e.g., a glass, polymer, plastic or magnetic bead or particle. A target DNA molecule may alternatively be immobilized on a solid support directly. Thus, in a preferred embodiment of the present invention a target DNA molecule may be immobilized on a solid support conjugated to streptavidin via a biotinylated capture oligonucleotide. In an alternative embodiment of the present invention, a target DNA molecule may be biotinylated and immobilized on a solid support conjugated to streptavidin.

While molecular tests (e.g., the molecular tests of step (e) in the second aspect of the invention) are being performed the first culture vessel containing the clinical sample (or second culture vessel containing the portion thereof) is kept in culture. As indicated above, culturing simply involves incubating the culture vessel under conditions suitable for, or conducive to, microbial growth. Thus, this step may be performed as indicated for pre-culture above. This step means that if positive microbial identification is not obtained from the molecular tests (e.g., from step (e), the sample is available for traditional culture based identification protocols based on conventional phenotypic and/or biochemical tests, or indeed for further ID testing by any other means—these tests are not delayed because the culture is on-going, and a further clinical sample does not need to be taken, or further culture started. Indeed, at this time, if no microorganism is identified in the molecular tests, e.g., in step (e), then the culture may be continued as is, or the culture vessel may be transferred to another culture system (e.g., an automated culture system or cabinet designed for microbial identification and optionally also antimicrobial susceptibility testing. After an appropriate period of culture such further ID tests and also susceptibility tests may be performed, the latter for example by conventional AST testing means, e.g., by turbidimetrically-assessed broth dilution cultures or disc-diffusion tests to determine MICs.

In the second aspect of the invention, if a microorganism is identified in the test aliquot, an antimicrobial susceptibility test is performed on the cultured clinical sample that has been kept in culture in step (c). Conveniently, this may involve withdrawing or removing a further (e.g., second or subsequent, depending on how many aliquots have been removed for molecular testing) aliquot from the culture vessel (first or second culture vessel), and performing AST testing on this.

However, in the first aspect of the invention, an antimicrobial susceptibility test may be performed without first performing a molecular test and identifying a microorganism, and such a test may be performed on the cultured clinical sample obtained from step (b)(i) or step (c). A test aliquot may therefore be removed from the culture vessel at this stage and without first performing any other tests, and an AST test performed.

The methods of the invention may also comprise a further step at this stage of enriching the aliquot or cultured clinical sample for microorganisms. Procedures suitable for this are discussed above, and may include removing or separating non-microbial cells (i.e., test subject cells) from the aliquot/ cultured sample. In one embodiment, microbial cells can be separated e.g., by filtration.

Recognized and prescribed conditions for AST testing exist, and may be followed in order that readily comparable results may be obtained which are comparable to, or may be compared with, tests performed in other laboratories. This may involve for example the use of a prescribed medium and culture conditions. Thus, the further removed aliquot (or aliquot fraction/remainder etc.) for AST testing, or separated or enriched microorganisms therefrom, may be transferred into a suitable medium for microbial culture, for example Mueller-Hinton medium (MH-media), prior to the commencement of the antimicrobial susceptibility test. Microorganisms may be grown in the presence of a variety of antimicrobial agents to determine their susceptibility to a given antimicrobial agent. According to the present invention the antimicrobial agents are selected based on the identity of the microorganism, and on the nature of any genetic antimicrobial resistance markers identified within the microorganism. The antimicrobial agents, and the amounts to be used, may also be selected according to current clinical practice, e.g., according to which antimicrobial agents are currently used in practice to treat the identified microorganism, in order that the susceptibility of the microorganism to the currently accepted or recognized antimicrobial treatment of choice can be assessed. Thus antimicrobial agents can be selected based on those known to be effective against the identified microorganism, or those currently used in practice to treat the microorganism, and excluding any agents to which resistance might be expected based on the presence of resistance markers, or such agents might be included and the amounts used might be selected to allow the determination of an amount or concentration of the antimicrobial agent that may be effective, despite the presence of the resistance marker. Antimicrobial agents are added to growth medium to a range of final concentrations or amounts. In a preferred embodiment of the present invention a serial dilution of the antimicrobial agent may be performed.

The step of growing, or culturing, the sample/microorganisms therefrom in the AST test may take place by any known or convenient means. Solid or liquid phase cultures may be used.

Thus, for example, in one preferred embodiment, the sample/microorganisms may be cultured on or in a plate or other solid medium containing the antimicrobial agent and microbial growth may be determined by visualizing (e.g., imaging) the microorganisms (i.e., imaging the plate etc.) Thus, the culture is visualized or imaged directly as a means of monitoring or assessing growth. Accordingly in one preferred embodiment the cultures are analyzed directly to monitor/assess growth. For example, the cultures may be grown in the wells of a plate and the wells may be imaged.

Alternatively, samples (or aliquots) may be removed (or taken) from the cultures, at intervals, or at different time points and the removed samples (aliquots) may be analyzed for microbial growth. This may be done by any means, including for example by means of molecular tests, e.g., nucleic acid based tests, Thus detection probes and/or primers may be used which bind to the microbial cells or to components released or separated from microbial cells. This may include for example nucleic acid probes or primers as described above for the identification test of step (e). In other embodiments, microbial cells may be detected directly, e.g., by staining, as described in more detail below.

Each antimicrobial agent is preferably used at least one concentration, in addition to a positive control in which the microorganism is allowed to grow in the absence of any antimicrobial agent. For example, 2, 3, 4, 5, 6, 7, or 8 or more concentrations of an antimicrobial agent are used. The concentrations used in a dilution series may differ two-fold between respective concentrations.

The term antimicrobial includes any agent that kills microorganisms or inhibits their growth. Antimicrobial agents of the present invention may particularly include antibiotics and antifungals. Antimicrobial agents may be microbicidal or microbiostatic. Various different classes of antibiotic are known, including antibiotics active against fungi, or particularly groups of fungi and any or all of these may be used. Antibiotics may include beta lactam antibiotics, cephalosporins, polymyxins, rifamycins, lipiarmycins, quinolones, sulfonamides, macrolides, lincosamides, tetracyclines, aminoglycosides, cyclic lipopeptides, glycylcyclines, oxazolidinones, lipiarmycins or carbapenams. Preferred antifungals of the present invention may include polyenes, imidazoles, triazoles and thiazoles, allylamines or echinocandins.

Accordingly, antimicrobial susceptibility may be determined by culturing the removed aliquot (or aliquot fraction etc.) or cultured clinical sample from step (c) in the second aspect of the invention, or the pre-cultured clinical sample from step (b)(i) or the cultured clinical sample from step (c) in the first aspect of the invention, or microorganisms separated or enriched therefrom, and analyzing the AST cultures over a range of time points. As for the culture step above, culture for AST may take place at any temperature that promotes microbial growth, e.g., between about 20° C. and 40° C., or 20 to 37° C., preferably between about 25° C. and 37° C., more preferably between about 30° C. and 37° C. or 30 to 35° C. In one embodiment the AST cultures may be cultured at about 35° C. The AST cultures may be analyzed at multiple time points to monitor microbial growth. For example, cultures may be analyzed at time points 0, 1, 2, 3, 4, 5, 6, 7, 8, 9, 10, 11, 12, 13, 14, 15, 16, 17, 18, 19, 20, 21, 22, 23 or 24 hours after the initiation of culture. A culture may be analyzed immediately after the initiation of culture, where t=0. Cultures may also be analyzed at time periods beyond 24 hours after the initiation of culture. Typically, cultures might be analyzed at 0, 1, 2, 3, 4, 6 and 24 hours after the initiation of culture. However, results obtained and reported in the Examples below show that short incubation times can be sufficient for detecting differential microbial growth e.g., 4 hours. Accordingly, shorter total incubation time of up to 8, 7, 6, 5, 4, 3 or 2 hours may also be used, e.g., analyzing every hour or every 2 hours or 90 minutes. As noted above, cultures are generally analyzed at two or more time points, e.g., at two or more time points up to 4, 5 or 6 hours of culture.

Microbial growth is monitored during the antimicrobial susceptibility test. Many methods for monitoring microbial growth are known and are used in AST tests, for example including turbimetric measurement, colorimetric determination, light detection, light scattering, pH measurement, spectroscopic measurements and fluorimetric detection. Any of these may be used. However, according to a preferred embodiment of the present invention growth may be detected and assessed by determining or assessing the number and/or amount and/or size and/or area of microbial cells in the sample by imaging methods, As noted above, the microbial cells can include cells in colonies and/or aggregates. This may be achieved by assessing or determining the number or amount of microorganisms present in the sample before and/or after growth in presence of antimicrobial agents by any of the methods known to measure or detect microorganisms. Such a determination may involve determining the number and/or size of microbial cells, aggregates and/or colonies. Again, techniques for this are known and available. Thus, growth may be measured by monitoring the number and/or amount and/or size of microorganisms and/or microbial cells and/or colonies and/or aggregates in a sample over time. This may be measured directly or indirectly. The number or amount of microorganisms in a sample may be measured directly by hemocytometry, flow cytometry, or automated microscopy. Microorganisms may be fixed and/or permeabilized prior to detection. Alternatively, microorganisms may be detected under in vivo conditions. Methods for AST testing by bacterial cell count monitoring using flow cytometry are described in Broeren et al., 2013, Clin. Microbiol. Infect. 19. 286-291. Methods for performing AST tests in which bacteria are grown and enumerated by automated microscopy in multi-channel fluidic cassettes are described by Price et al. 2014, J. Microbiol. Met. 98, 50-58 and by Metzger et al., 2014. J. Microbiol. Met. 79, 160-165, and by Accelerate Diagnostics (see for example WO 2014/040088 A1, US 2014/0278136 A1 and U.S. Pat. No. 8,460,887 B2). In these methods, bacteria are immobilized and grown on a surface, and individual bacteria and/or colonies are assessed for viability and/or growth (including measuring colony growth) by imaging the surface at two or more time points. Such methods may be used according to examples of the present invention. Other methods known are as described by Fredborg, et al., J. Clin. Microbiol. 2013 July; 51(7):2047-53, and by Unisensor (U.S. Pat. No. 8,780, 181) where bacteria are imaged in solution using bright-field microscopy by taking a series of stacked images (object planes) of the solution, and counting the bacteria present in the sample.

Whilst any of the methods based on using imaging to monitor microbial growth may be used, the methods of the invention preferably do not rely on counting individual cells or on monitoring the growth of individual cells or colonies (e.g., on monitoring an increase in size of an individual cell or colony e.g., according to the methods of Accelerate Diagnostics Inc.) Thus, the present invention is not limited to (and in preferred embodiments does not involve) using a fixed position for imaging an AST culture or AST culture sample. Rather, it is preferred according to the present invention to monitor the bulk growth of cells in the AST culture or culture sample, e.g., by imaging bulk cells in the field of view. The amount (e.g., area) of microbial cell matter (biomass) in the field of view may be determined by imaging. The cells/microbial biomass may be detected directly (e.g., by the microscope or camera etc.) e.g., using bright field microscopy or the microbial cells may be stained for detection, e.g., by adding stain to the AST culture or culture sample after the predetermined or required time period of growth.

In a further particular embodiment, the AST cultures or culture samples may be imaged or visualized directly without immobilizing the microbial cells, e.g., without applying a force, such as electrophoresis, to localize the cells to a detection location or surface for imaging.

In such imaging methods, algorithms may be applied to determine a value for the amount of microbial growth from the images according to methods and principles well known in the art. Thus, statistical methods may be applied to the images of microbial cells, based on the number, size, and/or area of microbial cell matter/biomass in the images (e.g., the amount of all the microbial cell matter in the image/field of view, for example total cell matter imaged). Algorithms may be written to take account of different growth patterns and/or morphologies, based on the identity of the microorganism and the antimicrobial agent present in the culture.

Such counting or imaging methods allow a digital phenotypic analysis of the microorganism in the AST test. Data has been obtained which shows that such digital phenotypic determinations deliver a MIC value similar to that of reference techniques (e.g., microbroth dilution).

A particular advantage of using such methods is that antimicrobial susceptibility testing may be performed on samples comprising a wide range of concentrations or amounts of microorganisms, and it is not necessary to use a standardized microbial titer prior to performing the antimicrobial susceptibility testing. A useful feature of the present invention is the ability to use different concentrations of microorganisms. A sample comprising at least $10^3$ CFU/ml may be used in the methods of the samples, for example samples comprising at least $10^4$, $10^5$, $10^6$, $10^7$ $10^8$ or $10^9$ CFU/ml may be used. Alternatively, a sample comprising less than $10^3$ CFU/ml may be used, for example at least $10^2$ CFU/ml. A sample comprising less than $10^2$ CFU/ml may also be used in the methods of the present invention.

In one embodiment of the present invention, microorganisms may be detected by adding a marker that stains microorganisms (i.e., a stain or dye) prior to determining the number or amount of microorganisms in a sample or by methods which utilize an intrinsic property of the microorganism such as e.g., phase contrast or any other method known in the art for quantifying the number of bacteria in the sample. Suitable stains might include colored or fluorescent dyes, for example Gram staining or other staining for peptidoglycan or DNA staining, as a means of visualizing the microorganism. In one particular embodiment of the present invention, DNA within a microorganism may be stained using Vybrant® DyeCycle™. Other DNA stains are well known and available. Indeed, the number of stains available in the art for staining bacteria is vast and large numbers of such stains have been documented, including in standard reference texts, and are commercially available, e.g., from Life Technologies. Direct labelling of microorganisms by staining is easy to perform, convenient and cost-effective, and therefore represents a preferred embodiment.

Thus, for example, the microorganisms may be grown for the AST test in wells of a microtiter plate, and the end of the growth periods the dye or stain may be added and the plate wells may be imaged and the number or amount of microorganisms may be assessed, by determining the number and/or size of microbial cells, aggregates or colonies e.g., by counting or imaging. Alternatively, microorganisms may be enumerated using a flow cytometer or similar type of instrument, for example the Aquila 400™ instrument from Q-linea AB (Sweden), e.g., as described in U.S. patent application No. 61/979,319.

In an alternative embodiment a microorganism may be specifically labelled via a biological feature within or on the microorganism. A "biological feature" may for example be a molecule in or on the microorganism e.g., a protein or other biomolecule expressed or located on the cell surface. For example, a label, e.g., a colored or fluorescent label, may be coupled to a protein or other affinity binding molecule that binds specifically to a particular biological feature. In one embodiment the protein may be a lectin, affibody or antibody, or antibody fragment. The microorganisms labelled in this way may be detected e.g., enumerated as previously described.

In a further embodiment proximity probes may be used to detect a specific biological feature within or on a microorganism.

In a further alternative embodiment of the present invention the microorganisms may be detected and enumerated using the padlock probe and RCA-based amplified single molecule detection (ASMD) method discussed above (for use in the molecular tests). Such methods enable single microbial cells to be detected and counted. Thus, the microorganism may be detected by binding of the padlock probe and the number of microorganisms in a sample may be measured indirectly by an amplified signal generated via RCA of the circularized padlock probe. Each RCA product (blob) may be indicative of a single microorganism. Microorganisms may be lysed and padlock probes may be used which are designed to hybridize to one or more nucleotide sequences of the microorganisms. This may include a step of separating DNA as discussed above, and preferably of selectively separating, or enriching for, microbial DNA, again as discussed above. Since in the AST test the cultures are usually less complex than in the step of initial clinical sample culture, a simplified protocol for separating or enriching microbial DNA may be used, involving for example filtration to separate microorganisms and microbial cell lysis or simply direct microbial cell lysis.

Alternatively, affinity binding molecules may be used which bind to one or more molecules present on a microorganism or within a lysed microorganism, such an affinity probe being provided with a nucleic acid label or tag to which a padlock probe may hybridize i.e., akin to an immunoRCA detection procedure. Similarly, proximity probes may be used to bind to a target in or on a microorganism and the nucleic acid domains of the proximity probes may be used to template the ligation of a padlock probe and optionally also prime its amplification by RCA. Procedures for this are widely known and described in the literature. As above C2CA may be used for signal amplification. The number of microorganisms in a sample can therefore be estimated by counting the number of blobs, which may be labelled e.g., fluorescently-labelled as described above 'blobs' within a sample. This thus provides another convenient means of obtaining a digital phenotypic susceptibility readout.

It is generally speaking advantageous in performing an AST test for the microbial culture under test to be pure, i.e., for there to be a single microorganism.

Thus, in a preferred embodiment according to the second aspect of the present invention, in step (f), the AST test is performed if a single microorganism is identified in the nucleic acid tests of step (e). That is, the AST test of step (f) is performed if the clinical sample is determined to contain only a single microorganism. This ensures that only a pure culture may be used in the AST test. Thus, in certain embodiments if two or more microorganisms are identified, the AST step of step (f) is not performed and the clinical sample is further cultured to enable further microbial identification and antimicrobial susceptibility tests to be performed to identify the microorganism and determine its antimicrobial resistance profile. However, this is not an essential feature, and it is possible to use microbial detection methods based on visualization or imaging to perform AST tests, for example methods as provided by Accelerate Diagnostics which use imaging of bacteria on a surface and not in solution, or indeed methods in which labelled microorganisms are detected in fluidic systems e.g., the automated microscopy fluidic cassette-based systems of Price et al. 2014, J. Microbiol. Met. 98, 50-58 and by Metzger et al., 2014. J. Microbiol. Met. 79, 160-165, discussed above. Any cell-by-cell detection and identification methods may be used for AST testing of samples which contain more than one microorganism.

Conveniently the methods of the present invention may be automated. Thus, any one of more of steps (b)(ii) to (f) in the method according to the second aspect of the invention may be automated, preferably any or all of steps (b)(ii) to (f). Analogously, any one or more of the steps following step (b)(i) in the method according to the first aspect of the invention (i.e., steps (b)(ii), (b)(iii), (c) and tests for the purpose of identifying a microorganism and/or determining the antimicrobial susceptibility of a microorganism in the clinical sample may be automated, preferably all such steps. Various specific or preferred steps discussed above lend themselves well to automation, for example the preferred padlock probe based ASMD methods for molecular testing and/or AST testing and the microbial/colony counting methods. Automatic culturing methods have already been developed, including for blood culture methods for microbial identification and/or AST testing and can be used or adapted for use according to the present invention. Automation would provide the advantage of speed and ease of operation, as well as multiplexing ability, which are of importance in clinical laboratory setting and especially important in the diagnosis of sepsis.

As mentioned above and explained further below, a dedicated instrument or device may be provided to perform any one or all of the steps of the methods described above, which device may be designed to receive the first culture vessel containing the clinical sample for testing of the clinical sample. Such a device may perform one or all of steps (b)(ii) to (f) of the method of the second aspect of the invention, which device may be designed to receive the first culture vessel containing the clinical sample culture for culturing and AST and ID testing. Alternatively, the device may perform any one or all of the steps of the method according to the first aspect of the invention, i.e., any one of steps (b)(ii) to (c) and/or to performing one or more tests on the medical sample for the purpose of identifying and/or determining the antimicrobial susceptibility of a microorganism in the clinical sample. Thus, preferably the clinical sample processing system is a microorganism detecting device. The present invention thus provides a clinical sample testing system comprising a portable apparatus as described herein, and a microorganism detection device.

Such a microorganism detection device may comprise a test aliquot extraction device for removing a portion of the contents of the first culture vessel for use as a test aliquot; a culturing device for culturing the medical sample in the first culture vessel after extraction of the test aliquot, and optionally before extraction of the test aliquot; and a DNA testing device for separating DNA from the test aliquot, and performing nucleic acid tests on the DNA to identify the microorganism and to detect the presence or absence of one or more genetic antimicrobial resistance markers in the microorganism.

In one embodiment, the clinical sample processing system for further testing of the clinical sample therefore comprises:

a microorganism detection device configured to receive said first culture vessel and being arranged for culturing the clinical sample, said device comprising:

optionally a second culture vessel containing a culture medium;

optionally a portion removal device for removing a portion of the contents of the first culture vessel and transferring the portion to the second culture vessel;

wherein the second culture vessel is arranged to receive a clinical sample culture as the portion of the contents of the first culture vessel, and is arranged to culture the portion;

the device further comprising:

a test aliquot extraction device for removing a portion of the contents of the first and/or second culture vessel for use as a test aliquot; and a DNA testing device for separating DNA from said test aliquot and performing nucleic acid tests on said DNA to identify the microorganism and to detect the presence or absence of one or more genetic antimicrobial resistance markers in said microorganism;

and/or an antimicrobial susceptibility test device for performing an antimicrobial susceptibility test on said cultured clinical sample and/or cultured portion by monitoring microbial growth by assessing growth or markers for growth; wherein the device is for culturing the clinical sample and/or portion after extraction of the test aliquot, and optionally before extraction of the test aliquot.

Thus, in one embodiment, the microorganism detection device comprises the DNA testing device as described above. In an alternative embodiment, the microorganism detection device comprises the antimicrobial susceptibility device for performing an antimicrobial susceptibility test. In another embodiment, the device comprises both the DNA testing device and the antimicrobial susceptibility device for performing an antimicrobial susceptibility test as described above.

In a representative embodiment, the DNA testing device is arranged to perform the nucleic acid tests using:

i. one or more nucleic acid probes or primers for microbial identification, a said probe or primer being capable of hybridizing specifically to, or a said primer being capable of selectively amplifying, a nucleotide sequence which is identificatory of a given microorganism; and ii. one or more nucleic acid probes or primers for antimicrobial resistance marker detection, a said probe or primer being capable of hybridizing to, or a said primer being capable of selectively amplifying, a nucleotide sequence representing a genetic antimicrobial resistance marker;

and it is detected whether or not said probes or primers have hybridized to said DNA and/or whether or not said primers have taken part in an amplification reaction.

In certain embodiments, the microorganism detection device is arranged such that: if the given microorganism is identified by the DNA testing device, then the cultured clinical sample produced by the culture vessel by culturing after extraction of the test aliquot is passed to an antimicrobial susceptibility test device for performing antimicrobial susceptibility test on the cultured clinical sample by monitoring microbial growth by assessing growth or markers for growth, and wherein the type and concentration of antimicrobial agents used in the antimicrobial susceptibility test is determined by the identity of the microorganism and antimicrobial resistance markers detected by the DNA testing device; and if the given microorganism is not identified by the DNA testing device, then the microorganism detection device further cultures the clinical sample in the culture vessel to enable further microbial identification and antimicrobial susceptibility tests to be performed after additional culturing in order to identify the microorganism and determine its antimicrobial resistance profile.

In a preferred embodiment, the present invention provides a clinical sample testing system comprising:

a portable apparatus for transport and incubation of a clinical sample in a first culture vessel, the apparatus comprising: a sealable container having a thermally insulated compartment for receiving the first culture vessel and a heater for heating the clinical sample to a temperature suitable for pre-culturing of the sample; and a microorganism detection device configured to receive said first culture vessel and being arranged for culturing the clinical sample, said device comprising:

optionally a second culture vessel containing a culture medium;

optionally a portion removal device for removing a portion of the contents of the first culture vessel and transferring the portion to the second culture vessel;

wherein the second culture vessel is arranged to receive a clinical sample culture as the portion of the contents of the first culture vessel, and is arranged to culture the portion;

the device further comprising:

a test aliquot extraction device for removing a portion of the contents of the first and/or second culture vessel for use as a test aliquot; and a DNA testing device for separating DNA from said test aliquot, and performing nucleic acid tests on said DNA to identify the microorganism and to detect the presence or absence of one or more genetic antimicrobial resistance markers in said microorganism, wherein the DNA testing device is arranged to perform the nucleic acid tests using:

i. one or more nucleic acid probes or primers for microbial identification, a said probe or primer being capable of hybridizing specifically to, or a said primer being capable of selectively amplifying, a nucleotide sequence which is identificatory of a given microorganism; and ii. one or more nucleic acid probes or primers for antimicrobial resistance marker detection, a said probe or primer being capable of hybridizing to, or a said primer being capable of selectively amplifying, a nucleotide sequence representing a genetic antimicrobial resistance marker;

and it is detected whether or not said probes or primers have hybridized to said DNA and/or whether or not said primers have taken part in an amplification reaction;

wherein the microorganism detection device is arranged such that: if the given microorganism is identified by the DNA testing device, then the cultured clinical sample and/or cultured portion produced by the first and/or second culture vessel by culturing after extraction of the test aliquot is passed to an antimicrobial susceptibility test device for performing antimicrobial susceptibility test on said cultured clinical sample and/or cultured portion by monitoring microbial growth by assessing growth or markers for growth, and wherein the type and concentration of antimicrobial agents used in said antimicrobial susceptibility test is determined by the identity of the microorganism and antimicrobial resistance markers detected by the DNA testing device; wherein the device is for culturing the clinical sample and/or portion after extraction of the test aliquot, and optionally before extraction of the test aliquot.

Viewed from a further aspect, the system comprises a microorganism detection device configured to receive said first culture vessel and being arranged for culturing the clinical sample, said device comprising:

a test aliquot extraction device for removing a portion of the contents of the first culture vessel for use as a test aliquot; and a DNA testing device for separating DNA from said test aliquot, and performing nucleic acid tests on said DNA to identify the microorganism and to detect the presence or absence of one or more genetic antimicrobial resistance markers in said microorganism, wherein the DNA testing device is arranged to perform the nucleic acid tests using:

i. one or more nucleic acid probes or primers for microbial identification, a said probe or primer being capable of hybridizing specifically to, or a said primer being capable of selectively amplifying, a nucleotide sequence which is identificatory of a given microorganism; and ii. one or more nucleic acid probes or primers for antimicrobial resistance marker detection, a said probe or primer being capable of hybridizing to, or a said primer being capable of selectively amplifying, a nucleotide sequence representing a genetic antimicrobial resistance marker;

and it is detected whether or not said probes or primers have hybridized to said DNA and/or whether or not said primers have taken part in an amplification reaction;

wherein the microorganism detection device is arranged such that: if the given microorganism is identified by the DNA testing device, then the cultured clinical sample produced by the first culture vessel by culturing after extraction of the test aliquot is passed to an antimicrobial susceptibility test device for performing antimicrobial susceptibility test on said cultured clinical sample by monitoring microbial growth by assessing growth or markers for growth, and wherein the type and concentration of antimicrobial agents used in said antimicrobial susceptibility test is determined by the identity of the microorganism and antimicrobial resistance markers detected by the DNA testing device;

wherein the device is for culturing the clinical sample after extraction of the test aliquot, and optionally before extraction of the test aliquot.

Viewed from yet a further aspect, the system comprises a microorganism detection device configured to receive said first culture vessel and being arranged for culturing the clinical sample, said device comprising:

a second culture vessel containing a culture medium;

a portion removal device for removing a portion of the contents of the first culture vessel and transferring the portion to the second culture vessel;

wherein the second culture vessel is arranged to receive a clinical sample/medium mixture or a clinical sample culture as the portion of the contents of the first culture vessel, and is arranged to culture the portion;

the device further comprising:

a test aliquot extraction device for removing a portion of the contents of the second culture vessel for use as a test aliquot; and a DNA testing device for separating DNA from said test aliquot, and performing nucleic acid tests on said DNA to identify the microorganism and to detect the presence or absence of one or more genetic antimicrobial resistance markers in said microorganism, wherein the DNA testing device is arranged to perform the nucleic acid tests using:

i. one or more nucleic acid probes or primers for microbial identification, a said probe or primer being capable of hybridizing specifically to, or a said primer being capable of selectively amplifying, a nucleotide sequence which is identificatory of a given microorganism; and ii. one or more nucleic acid probes or primers for antimicrobial resistance marker detection, a said probe or primer being capable of hybridizing to, or a said primer being capable of selectively amplifying, a nucleotide sequence representing a genetic antimicrobial resistance marker;

and it is detected whether or not said probes or primers have hybridized to said DNA and/or whether or not said primers have taken part in an amplification reaction;

wherein the microorganism detection device is arranged such that: if the given microorganism is identified by the DNA testing device, then the cultured portion produced by the second culture vessel by culturing after extraction of the test aliquot is passed to an antimicrobial susceptibility test device for performing antimicrobial susceptibility test on said cultured portion by monitoring microbial growth by assessing growth or markers for growth, and wherein the type and concentration of antimicrobial agents used in said antimicrobial susceptibility test is determined by the identity of the microorganism and antimicrobial resistance markers detected by the DNA testing device;

wherein the device is for culturing the portion after extraction of the test aliquot, and optionally before extraction of the test aliquot.

In certain embodiments, the microorganism detection device may be configured to further culture said clinical sample and/or cultured portion in the first and/or second culture vessel if the given microorganism is not identified by the DNA testing device, to enable further microbial identification and antimicrobial susceptibility tests to be performed after additional culturing in order to identify the microorganism and determine its antimicrobial resistance profile.

The portable apparatus comprises a sealable container having a thermally insulated compartment for receiving the first culture vessel and a heater for heating the clinical sample to a temperature suitable for pre-culturing of the sample.

The heater may preferably be for maintaining the sample at a temperature suitable for pre-culturing of the sample. Here, maintaining the temperature means holding the temperature of the sample within a given range (at which pre-culturing can still take place) for a predetermined length of time, or until the first culture vessel is removed from the container. Preferably the sample is maintained at a temperature which is within 5 degrees of the optimal temperature, more preferably within 2 degrees of the optimal temperature. In order to maintain the sample at a required temperature after heating the heater should be arranged to provide sufficient heat to replace the heat lost from the thermally insulated compartment during use of the device to transport the sample.

As briefly discussed above in reference to the methods of the present invention, in certain embodiments the portable apparatus may comprise an agitator to agitate the first culture vessel and/or the sample within the vessel during transport. Agitation during heating ensures even heating of the sample as well as promoting effective culturing of the sample. The use of agitation has been found to be beneficial to the operation of the pre-culturing apparatus. In such embodiments, the proposed apparatus can hence provide improved culturing compared to devices without an integrated agitator device. Microbiological agents in the sample can be kept in suspension and the agitation also allows the sample to be aerated. The agitator may roll, tilt, displace, shake, rotate, or repeatedly invert the culture vessel. Thus, the vessel may be moved relative to the rest of the portable apparatus. Alternatively, or additionally, the agitator may move the sample within the vessel, which may be done without movement of the vessel relative to the rest of the portable apparatus. For example, the culture vessel may include a magnetic stir bar and the agitator may comprise a means for generating a rotating magnetic field (for example, a rotating magnet or a set of stationary electromagnets), the agitator then being operable to cause the magnetic stir bar to spin, thereby stirring the sample. A further alternative is to use thermal convection by the use of a differential temperature on the different sides of the culture vessel.

The inventors have made the non-obvious realization that for some diagnostic systems, such as that described in WO2015/189390, pre-culturing is not problematic. For example, pre-culturing is acceptable if the analysis is not dependent on a positive determination of microbial growth, i.e., detecting a positive sample in a conventional culture cabinet. Where pre-culturing is acceptable, the container need not be cooled as there is no need to prevent (or reduce the degree of) pre-culturing. Furthermore, the inventors have realized that it is advantageous to pre-culture the sample as it is in transit to the laboratory, because this allows the sample testing to be run faster once it is received at the laboratory performing the testing. Therefore, the inventors have recognized that it is advantageous to heat the sample to above room temperature, whilst optionally agitating the sample periodically or continuously rather than cooling it or maintaining it at room temperature.

The thermally insulated compartment is provided inside the sealable container, that is, it is an interior space/volume within the sealable container. The thermally insulated compartment may comprise a sleeve for holding the first culture vessel. It is advantageous for the sleeve to be removable and preferably disposable. A removable sleeve allows for ease of handling of the sleeve with the culture vessel within it, as well as the possibility to insert and remove culture vessel with the sleeve outside of the apparatus. A disposable sleeve ensures that the risk of contamination from contact with the outside of the first culture vessel can be avoided. A new sleeve can be used for each use of the portable apparatus, with the portable apparatus never coming into direct contact with the first culture vessel. In this case the agitator may agitate the first culture vessel by movement of the sleeve.

The sleeve may be arranged to resiliently deform during insertion and removal of the first culture vessel, and to hold the culture vessel securely due to the resilience of the sleeve whilst the culture vessel is fully inserted. For example, the sleeve may comprise resilient tines arranged to clasp a shoulder of the culture vessel when the vessel is inserted, and to be pushed resiliently outwardly and pass around a circumference of the main body of the culture vessel when the vessel is being inserted or removed.

In this case where the first culture vessel itself moves to allow agitation, with or without a sleeve, the compartment and container must be sized appropriately so as to allow the required degree of movement. The compartment may hence be larger than the first culture vessel in order to allow for movement of the culture vessel within the compartment. The first culture vessel may be received within a sleeve within the compartment, and the sleeve may be moved by the agitator (relative to the stationary compartment) so as to control movement of the first culture vessel. The container may then receive the compartment snugly. Alternatively, the compartment may be sized so as to receive the first culture vessel snugly, and the container may be sized so as to allow movement of the compartment itself within the container.

The first culture vessel may be rotated and/or rocked about one or more axis whilst it is a generally horizontal position, a generally vertical position, or any other orientation. In this context horizontal and vertical references the orientation of the main axis of the flask, i.e., the axis of rotation for a bottle shaped flask. Typically, the opening of the first culture vessel will be at the top of this axis when the flask is held vertically.

One possible arrangement for an agitator is to place the first culture vessel in a horizontal position within the container, and for the agitator to be arranged to roll the culture vessel about its axis and/or to rock the axis in a see-saw motion in order to agitate the culture. It is preferred in this case for the portable apparatus to be arranged to be transported horizontally, and therefore the apparatus may be provided with markings or instructions indicating an orientation with the culture vessel horizontal during transport.

Another possibility is to provide an off-center (i.e., off-axial) rotational movement of one or both of the ends of the first culture vessel, e.g., the top of the culture vessel, the bottom of culture vessel or both the top and the bottom of the culture vessel. This could be done with the first culture vessel generally horizontal or generally vertical, for example by combining a horizontal rolling, off-axis, rotation producing a back and forth sloshing movement of the sample fluid, or combining a vertical spinning and off-axis rotation producing a vortex and a swirling motion within the fluid. Angles between the horizontal and the vertical can also be used, for example a 45° angle of the axis of the flask. Such off-axial rotating movement may be provided by an eccentric cam or a yoke/gimbal device, for example. The axis of symmetry of the first culture vessel can be misaligned with the axis of rotation of the cam, and the two axes are non-parallel, such that the culture vessel rotates in an off-axial manner.

The first culture vessel may be rotated continuously or intermittently, and optionally with changes in the direction of rotation. In this way the degree of agitation that is applied via the rotation can be controlled.

One example embodiment uses a swash plate type formation, with the first culture vessel coupled to a rotation device with an axis of symmetry of the first culture vessel out of alignment with the axis of rotation of the rotation device. One way to achieve this is to mount the first culture vessel with the base of the flask being non-perpendicular to the axis of rotation, for example by having a slanted surface, a spacer structure, a wedge or any other structure ensuring that the base of the culture vessel does not sit perpendicular to the axis of rotation of the rotation device. The mounting of the first culture vessel may be via a sleeve that holds the flask as explained above.

Another example uses a yoke with the first culture vessel hung vertically from a pivoted connection and the center of mass of the culture vessel below the pivot point. This yoke can be mounted for rotation and when the yoke is spun the hanging vessel will swing outward allowing for a swirling motion to be applied to the sample in the culture vessel.

The rotation device may include a wheel rotated by a motor, with the radial direction of the wheel being perpendicular to the axis of rotation, which may pass through the center of the wheel. An off-center axis could provide a further option for an agitation action. The apparatus may be arranged so that the first culture vessel is held on the wheel for rotation with the wheel, for example by means of a suitable key or other interconnection, including a yoke as described above, and so that the first culture vessel has its base non-parallel with the radial direction of the wheel during rotation. The off-center movement can be combined with a rolling movement while consuming only low energy for the agitation.

Another possibility is to allow a horizontal rolling movement of the first culture vessel, while horizontally positioned, to create agitation within the sample.

As indicated above, yet a further possibility for an agitator is to agitate the contents of the first culture vessel (a mixture of a suitable culture medium and the clinical sample) directly, e.g., without shaking, tilting, rocking or rolling the first culture vessel itself. Accordingly, in certain embodiments the culture vessel may contain a magnetic stirring device, e.g., a magnetic stir bar or magnetically driven spinner), and the agitator may comprise a means for generating a rotating magnetic field (for example, a rotating magnet or a set of stationary electromagnets), the agitator then being operable to cause the magnetic stir bar to spin, thereby stirring the sample. Alternatively, the culture vessel may contain a stirrer shaft comprising a central shaft mounted along the main axis of the first culture vessel comprising one or more stirrer paddles or blades which may be mounted radially to the central shaft) which may be mechanically rotated via a portion which extends outside the culture vessel, and the agitator may comprise a means for rotating the stirring device (for example a motor configured to drive the stirring device via its external portion, e.g., via an adaptor).

The agitator may be controlled by a controller. The agitation may be recorded by an accelerometer to measure the degree of agitation of the first culture vessel during transportation. In this case the controller may adjust the duration and/or the degree of agitation to provide a pre-set minimum agitation of the sample. The degree of agitation recorded by the accelerometer may be shown on the display on which the recorded by the timer is displayed, or on a separate display.

The agitator may agitate the sample constantly, or may agitate the sample intermittently, i.e., by cycling through a period of agitating constantly, followed by a period of no agitation. The lengths of the agitation period and non-agitation period can be chosen as appropriate and may be controlled by the controller.

The agitator may be mainly or entirely within the thermally insulated compartment. If the agitator, or at least the moving parts of the agitator, is within the thermally insulated compartment then the risk of loss of heat through openings within the thermally insulated compartment is minimized. Moreover, in the case where an electrical motor is used for agitation then the electrical motor can advantageously be within the insulated compartment since heat loss from the motor will then contribute toward heating of the thermally insulated compartment.

As noted above, the apparatus is suitable for transport of a clinical sample in a first culture vessel, and is therefore sized appropriately. Further, the apparatus may include a culture vessel (i.e., a first culture vessel) such as a blood culture flask as described elsewhere. Thus, in a preferred embodiment, the apparatus is suitable for transport of a clinical sample in a blood culture flask. It is to be noted that a blood culture flask is a recognized form of flask in the field of the invention and denotes a flask that is specifically designed for and provided for culturing of clinical samples such as blood samples. It would not, for example, be obvious to use such a flask in a device intended for purposes other than culturing of clinical samples, and thus even if a prior art device for preserving biological matter (such as the devices in GB 2055530 or U.S. Pat. No. 6,028,293) was capable of holding a blood culture flask it would nonetheless not be obvious to insert a blood culture flask into such a device. Instead, one skilled in the art would only look to blood culture devices when considering how to handle blood culture flasks. Moreover, it is not considered to be obvious to adapt specialized medical devices for other vessels, such as the vacuum collection tubes of US 2013/226032, to use a blood culture flask.

The apparatus may, for example, be suitable for transportation of a Becton Dickinson Bactec™ blood culture flask and may comprise such a flask. These have a maximum height of 147 mm and a maximum diameter of 39.7 mm. Alternatively, or additionally, the apparatus may be suitable for transportation of a Biomeriux BactAlert® blood culture flask. These have a maximum height of 117 mm and a maximum diameter of 35 mm. A further alternative is the apparatus may be suitable for transportation of a Thermo Fisher VersaTrek® blood culture flask and may comprise such a flask. The 40 ml VersaTrek® flask has a maximum height of 124 mm and a maximum diameter of 40 mm. The 80 ml VersaTrek® flask has a maximum height of 105 mm and a maximum diameter of 57 mm.

Alternatively, or additionally, the apparatus may be suitable for transportation of any other blood culture flask, preferably having a volume of less than 200 ml, more preferably less than 100 ml and most preferably less than 50 ml, and having known dimensions, and the apparatus may comprise such a blood culture flask.

In some examples the apparatus includes a first culture vessel and also a clinical sample within the first culture vessel. The clinical sample is preferably a sample as described above provided in the vessel in a state that requires culturing in relation to subsequent processing of the sample. The clinical sample may be a blood sample requiring culturing to enable identification of micro-organisms in the blood. The clinical sample may be a sample taken from a patient in order to provide information about the patient's medical condition. The sample may be a sample taken from a patient for the purpose of detecting and characterizing a microorganism in the sample, for example by using a method as described in WO2015/189390. The sample may be provided in the flask in an initially uncultured state, with culturing of the sample then occurring during transport of the sample in the flask within the apparatus. The apparatus may thus comprise an uncultured clinical sample that requires culturing, a partially cultured clinical sample, or a sample that has been cultured sufficiently to allow for further processing and/or testing of the sample, for example diagnostic testing such as that described in patent application WO2015/189390. However, as discussed in greater detail above, the diagnostic testing may perform one or more tests on the medical sample for the purpose of identifying a microorganism and/or determining the antimicrobial susceptibility of a microorganism in the clinical sample, e.g., an ID and/or an AST test, and the diagnostic testing performed by the device need not be limited to performing a detection method as described in the above patent application.

The apparatus may have outer dimensions allowing it to be transported in a pneumatic tube system.

The thermally insulated compartment is preferably designed with suitable dimensions for receiving the first culture vessel. In particularly preferred embodiments, the apparatus is for receiving a blood culture flask, for example it may include a cylindrical space, which may be arranged to receive a flask with a diameter of 57 mm or below and a height of 147 mm or below. However, in some embodiments the compartment may be larger in order to allow for movement of the flask within the compartment. It is preferred for the thermally insulated compartment to receive all of or at least the majority of the flask.

The thermally insulated compartment may be lined with a resilient material and/or be provided with deformable elements for securely holding the first culture vessel. This may include a sleeve as described above. With the use of deformable/resilient elements the interior of the compartment may be smaller than the culture vessel when no culture vessel is present, and then deform to accommodate the culture vessel when the culture vessel is inserted. In order to allow for a range of culture vessels with different sizes to be accommodated by a single design of apparatus the apparatus may be equipped with an adjustment mechanism for adjusting the size of the compartment to fit vessels of different sizes. The adjustment mechanism may include the resilient material and/or deformable elements mentioned above. The adjustment mechanism may alternatively or additionally include one or more sliding elements (or detachable and movable elements) as parts of the walls of the compartment. For example, on or more of the walls may have a Velcro attachment to the sides of the sealable container, and the point of attachment may be movable by detaching the Velcro and then re-attaching it in a different position.

The container may be configured to hold only one culture vessel. Alternatively, the apparatus may be configured to hold a plurality of culture vessels, for example, two, three, or four culture vessels. The apparatus may be configured to receive the plurality of culture vessels within a single thermally insulated compartment (i.e., the thermally insulated compartment is sized to accommodate a plurality of vessels) or may comprise a plurality of thermally insulated compartments, each for receiving a single culture vessel. Where a plurality of thermally insulated compartments is provided, each compartment may be heated (and/or monitored and controlled, as described below) separately. It may be possible to separate the thermally insulated compartment that holds the culture vessel from the container. The separable thermally insulated compartment may be a consumable. The separate compartments may be transported individually.

The apparatus may comprise a controller for controlling the heater to maintain a pre-set temperature. This may allow the sample to be maintained at a precise and accurate temperature. The controller for controlling the heater may be the same as the controller for controlling the agitator.

The apparatus may comprise a temperature sensor for monitoring the temperature in the interior of the thermally insulated compartment. Where both a controller and temperature sensor are provided, the controller may be in communication with the temperature sensor so as to receive the measured temperature output from the temperature sensor. The controller may be operable to adjust the heater in accordance with the temperature measured by the temperature sensor, preferably in a feedback control system.

The heater may include a chemical heater. The chemical heater may be a single-use disposable heater, such that a new chemical heater is used each time a first culture vessel is pre-cultured. The chemical heater may for example make use of the heat released by catalyzing rusting of iron or dissolving calcium chloride. The heater may for example make use of an exothermic reaction between a plurality of reagents. Alternatively, the heater may make use of exothermic reactions such as phase-change materials e.g., exothermic crystallization of a supersaturated sodium acetate solution for example. Such heaters may be re-usable (and may be regenerated for re-use by placing in boiling water, for example).

The heater may include an electrical heater such as resistance heater, for example a coil of wire, or a kapton heater, each preferably powered by a battery. The output of the electrical heater may be controlled by the controller, which, as mentioned above, may control the heater responsive to temperature measurements from a temperature sensor. This may allow the temperature to be more precisely controlled. The heater may comprise a combination of different heaters. For example, a chemical heater may be used to raise the temperature of the sample rapidly from room temperature to the desired temperature, and then a resistance heater may be used to more precisely control the temperature once the sample is close to the optimal temperature, with low energy consumption.

The heater may be flexible and/or formed in a curve such as a partial or full tube shape, so that it may be wrapped or placed around at least part of the first culture vessel.

The heater may be activated automatically, for example by loading the sample into the container or by closing the container lid. Alternatively, the heater may be manually turned on by the user. The heater may be operable to heat and preferably maintain the sample at a temperature of 25° C. or higher, and more preferably at a temperature of 30° C. or higher.

The heater may be operable to heat and preferably maintain the sample at a temperature of 45° C. or lower, more preferably at a temperature of 40° C. or lower and most preferably at a temperature of 37° C. or lower. The heater may be operable to heat and preferably maintain the sample at a temperature of 25° C. to 40° C., more preferably 30° C. to 37° C., and most preferably 35° C.

The heater may be operable to heat and preferably maintain the sample within the above temperature ranges for a period of up to 12 hours, 6 hours, 4 hours, 3 hours or 1 hour.

There is of course an interaction between the required heater performance, the thermal insulation of the apparatus, and the outside/ambient temperature. The heater may be arranged to provide the above characteristics for ambient temperatures of 15° C. and above, preferably 10° C. and above and more preferably 0° C. and above. Lower temperature operation will typically not be required, but could be designed for if necessary.

In example embodiments the apparatus includes a power source such as a battery. The battery may be used to power an electrical heater as discussed above, as well as supplying power to a controller of the apparatus. The battery may be accessible via a removable lid or panel in order to allow replacement of the battery. In preferred embodiments the battery is rechargeable, thereby enabling repeated usage of the device without the need to replace the battery. The portable apparatus may be arranged to receive power for recharging the battery from a charging point and the invention extends to a combination of one or more portable apparatus as discussed herein with a charging point for recharging the battery of the portable apparatus. The portable apparatus may receive power via a wired connection, such as a plug and socket arrangement, preferably with the socket on the portable apparatus and the plug on a lead connected to the charging point. Alternatively, or additionally the charging point may be arranged for wireless power transmission to the portable apparatus, for example via inductive power transfer. The charging point may be arranged for connection to mains electricity.

The portable apparatus may be arranged to be operable to heat and optionally agitate the first culture vessel whilst being charged. In this way the charging point could be used for storage of the portable apparatus whilst it is waiting for the sample to be processed further, and the heating and/or agitation of the sample can be done during this storage without risk of depleting the power level of the portable apparatus.

In general, a medical institution would use multiple portable apparatuses simultaneously to allow for handling of many samples at once, perhaps tens or even hundreds of samples. The charging point may be arranged to charge multiple portable devices at any one time, for example more than 10 or more than 50 devices. The charging point could hence be provided with multiple inductive charging pads and/or multiple leads allowing for connection to many portable devices.

The thermal insulation of the thermally insulated compartment may be designed to operate within the same temperatures and to provide a degree of insulation suitable to maintain the required temperature with a given heater. The thermal insulation may include a layer of one or more of silica aerogel, expanded polyurethane, expanded polystyrene, urea foam or the like, in a thickness sufficient to give the required thermal capabilities, for example, at least 1 cm, at least 2 cm, or at least 3 cm, at least 4 cm or more, dependent on the selected heater and the required temperature and time period for pre-culturing. Multiple layers of insulation may be included if necessary. The thermal insulation may fully enclose the thermally insulated compartment and hence may be also included in a lid or other removable opening of the thermally insulated compartment.

The apparatus may comprise a timer for recording the amount of time for which the sample has been pre-cultured. The timer may be set automatically by loading the sample into the container, or may be manually set running by the user. Preferably, the timer is set running automatically when the heater is turned on. The timer may also be in communication with the controller, and the controller may set the timer running at the same time as the controller activates the heater. The communication between the timer and controller may be via RFID or any other means.

Where a timer is provided, the apparatus preferably also comprises a display for showing the time recorded by the timer. As a result, when the sample arrives at the laboratory, the length of time for which the sample has been pre-cultured can readily be assessed.

In each of the foregoing three aspects, the microorganism detection device may be arranged to perform any or all of the method steps and preferred/optional steps set out above. Thus, the DNA testing device may be arranged to carry out any or all of the DNA testing steps described above, and the antimicrobial susceptibility test device may be arranged to carry out any or all of the antimicrobial susceptibility testing steps described above.

The apparatus may comprise a means for determining the amount of microbial cell matter (that is microbial biomass) present in a sample, particularly by assessing or determining this directly. This may be achieved by determining the amount of microbial biomass visually, and especially by imaging. Therefore, the apparatus may comprise an imaging means (for example, a microscope and optionally a camera) for obtaining 2D images. The apparatus may comprise a processor for processing the images to determine the amount of microbial cell matter. The processor may be configured to determine the area of microbial biomass (more particularly the area of microbial biomass in the field of view under investigation, e.g., in an image).

More generally, the imaging means and processor may be configured to determine the amount and/or number and/or size of microorganisms and/or microbial colonies or aggregates. This may include counting of cells or colonies, but is not limited to such methods and includes any means of visually assessing the amount of microbial growth by assessing (or determining) the size, area, shape, morphology and/or number of microbial cells, colonies or aggregates (the term "aggregate" includes any collection of cells in physical proximity e.g., a clump or cluster; this may include non-clonal clumps/clusters of cells which have aggregated or stuck together (e.g., neighboring cells which have become aggregated) as well as clonal colonies). The parameter used to measure microbial growth may, but need not, vary according to the identity of the microbe (determined in step (e)) and the antimicrobial agents used in step (f). Indeed, depending on the organism and the antimicrobial agents used, the morphology or growth pattern of the cells may be affected, and this may be altered or changed from the "normal" or "typical" morphology or growth pattern, e.g., in the absence of the antimicrobial agent. Whilst some AST growth monitoring methods may depend on detecting such changes, it is not essential according to the present invention to take such changes into account and the amount (e.g., area) of microbial growth or biomass may be determined irrespective of morphology and/or growth pattern. Thus, the same growth monitoring method may be used regardless of the microbial cell and/or antimicrobial agents used.

The first culture vessel containing the pre-cultured clinical sample is inserted into the microorganism detection device, and the microorganism detection device is configured to receive or accept the first culture vessel.

Culture medium may be added to the second culture vessel prior to operation of the device, or the second culture vessel may be filled with culture medium when it is supplied. Typically, the second culture vessel will be a consumable item.

The further culturing of the clinical sample or portion in the first and/or second culture vessel may occur in the same piece of apparatus as the earlier testing steps, or alternatively the first and/or second culture vessel may be passed to a separate apparatus, with the microorganism detection device hence including multiple separate parts. In the latter case the first and/or second culture vessel may be handled in such way during extraction that it can be cultured during the further culturing step in another dedicated apparatus, which may advantageously be an apparatus that is already in place at the facility in question, which may for example be a hospital. Thus, the first and/or second culture vessel is made available for continued culturing and this may be inside the same apparatus as the preceding steps, or outside that apparatus and in another separate part of the device.

Figure 1:
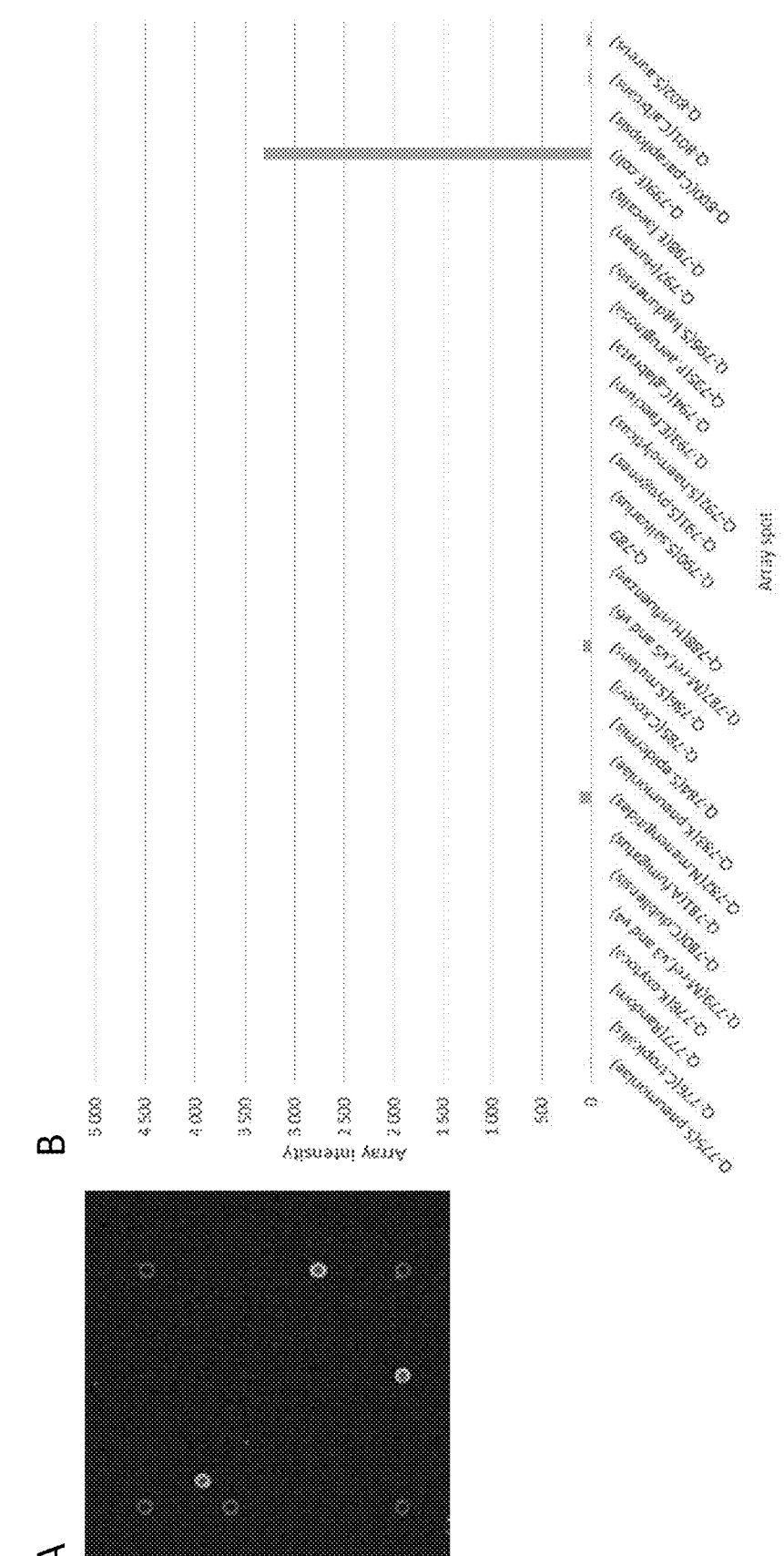
FIG. 1 depicts in (A) a sample microarray panel for the detection of microorganisms in a sample, and in (B) the fluorescence intensity of the signal generated for a range of microorganisms.

In FIG. 1A, the spots at the four corners and in the middle of the left hand side of the image are reference spots used for image alignment. The three brighter spots indicate that nucleotide sequences specific for *E. coli* are detected in the sample using the detection method of the present invention. FIG. 1B shows the signal generated for a range of different microorganisms when probes specific for *E. coli* are used.

Figure 2:
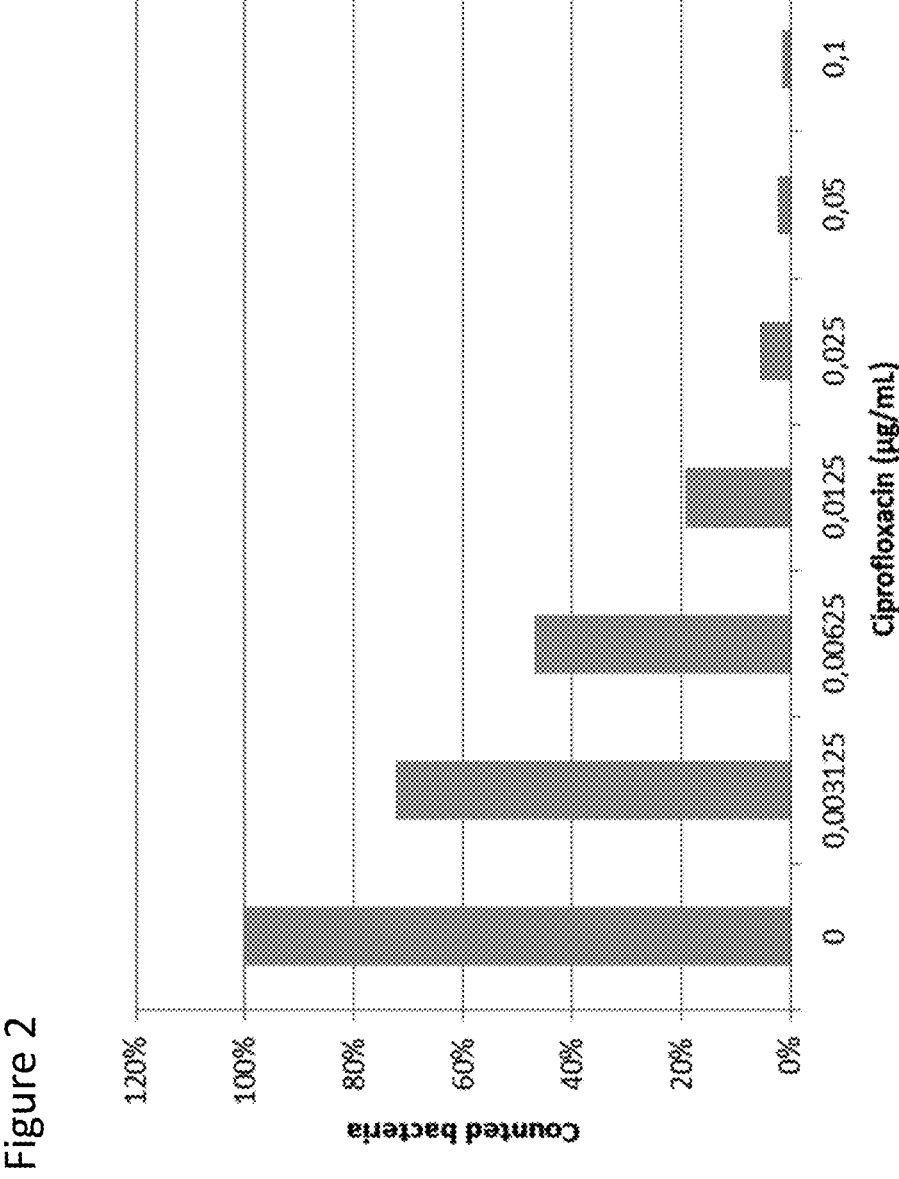
FIG. 2 shows the relative growth of bacteria grown in MH broth supplemented with ciprofloxacin at a range of different concentrations, relative to a positive control sample grown in the absence of ciprofloxacin.

FIG. 2 shows the relative growth of bacteria grown in MH broth supplemented with ciprofloxacin at a range of different concentrations, relative to a positive control sample grown in the absence of ciprofloxacin. Cells were stained with Vybrant® DyeCycle™ Orange stain and counted by automated microscopy.

Figure 3:
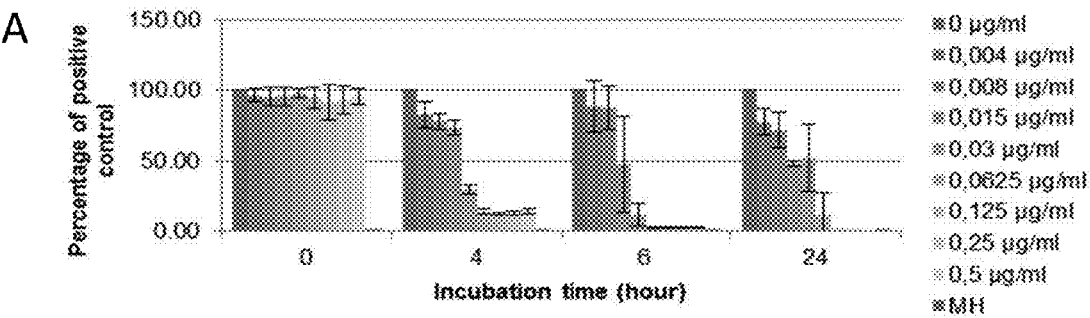
Figure 3:
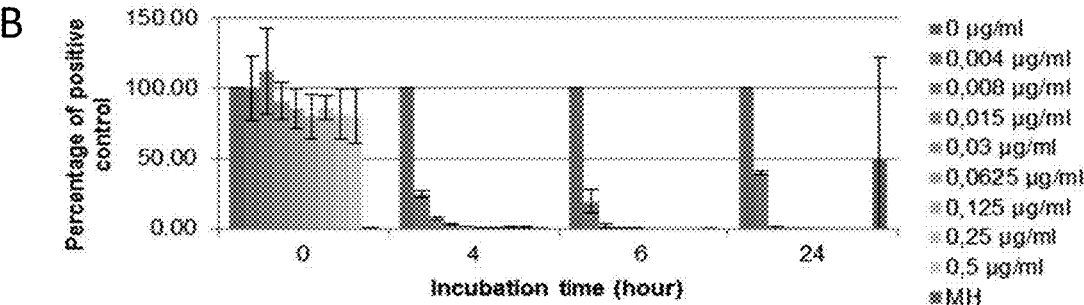
Figure 3:
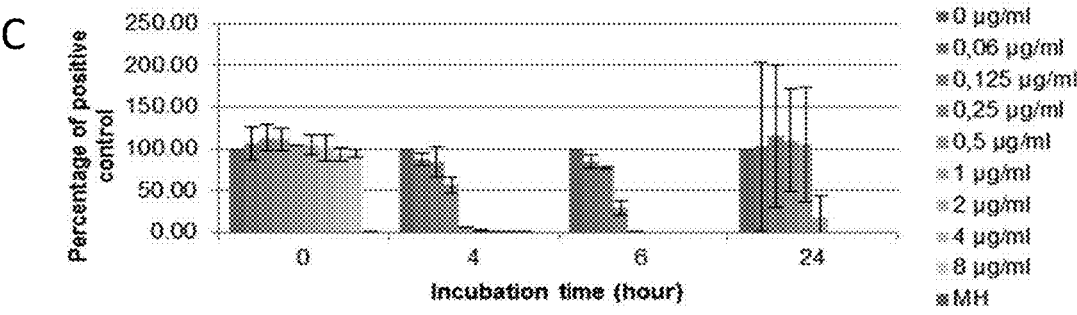
Figure 3:
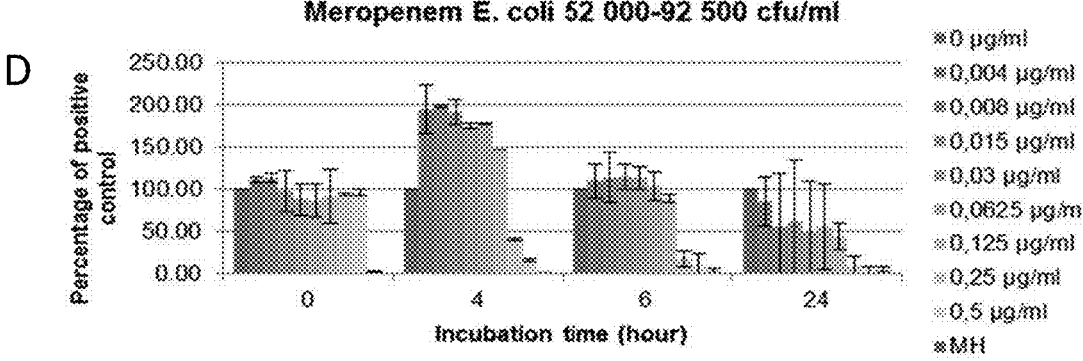
Figure 3:
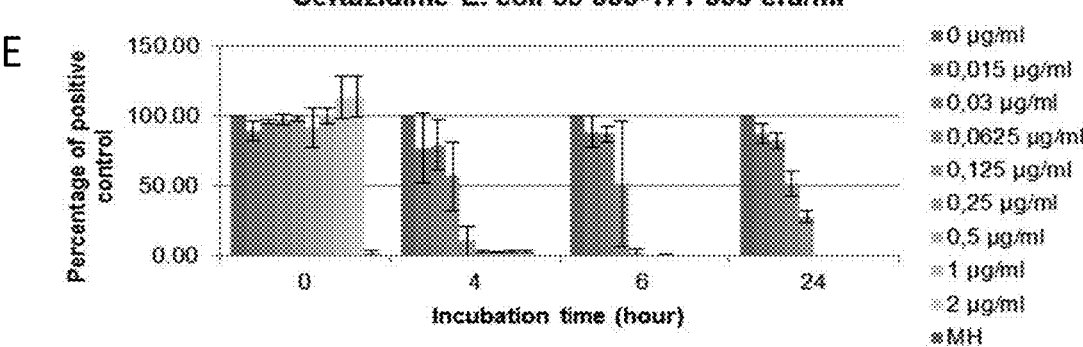
Figure 3:
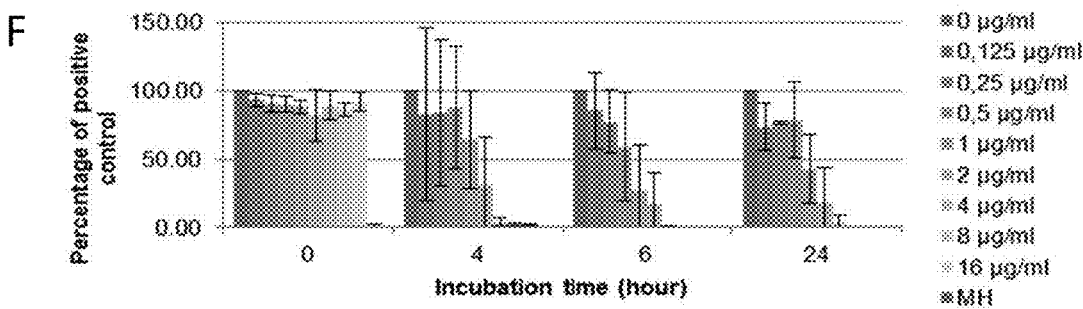

FIG. 3 shows the relative growth of bacteria grown in MH broth supplemented with a number of different antibiotics, each at a range of different concentrations, relative to positive control samples grown in the absence of any antibiotics (A—Cefotaxime, B—Ciprofloxacin, C—Gentamicin, D—Meropenem, E—Ceftazidime, F—Piperacillin+Tazobactam). Cells were stained with Vybrant® Dye-Cycle™ Orange stain and counted by Aquila 400. These data indicate that differential growth can be detected within 4 hours. MIC values were calculated for each of the antibiotics at 4, 6 and 24 hours, and at a range of cut-off values.

FIG. 4 depicts in (A) the workflow required for Amplified Single Molecule Detection (ASMD) of bacteria within a sample to determine antibiotic susceptibility of a microorganism, and in (B) shows the differential growth of bacteria grown in MH broth supplemented with Ciprofloxacin or Cefotaxime, relative to a positive control sample grown in the absence of either antibiotic. In FIG. 4B, the RCA products indicating the presence of specific microbial DNA sequences are detected by ASMD, and counted by Aquila 400.

FIG. 5 depicts a scheme for detecting specific microbial DNA sequences for use in probe design. A biotinylated capture oligonucleotide complementary to a region of microbial DNA binds a target DNA fragment and immobilizes it onto a solid phase. A padlock probe, comprising two target-complementary parts (5'/3'-arms) and a backbone with sites for detection (DO—generic), restriction digestion and priming (RO—generic), and array oligo hybridization (AO—unique) binds to its target via its complementary 5' and 3' end sequences, and can be ligated into a circle prior to RCA amplification and C2CA reaction.

FIG. 6 shows a portable apparatus for transport of a clinical sample in a culture vessel.

FIG. 7 shows a schematic of a controller, temperature sensor, heater, agitator, accelerometer, timer and display for use in a portable apparatus as shown in the Figures.

FIGS. 8a and 8b show further details of a part of another a portable apparatus for transport of a clinical sample in a culture vessel.

FIG. 9 shows a cross-section of another portable apparatus showing the details of a possible agitation mechanism.

FIG. 10 is a box-whisker diagram showing typical times for transport of samples from a patient to a diagnostic system.

FIGS. 11a-11c show growth of bacteria at room temperature (triangular data points) as compared to at 35° C. (circular data points) for (a) E. coli, (b) S aureus and (c) C. albicans.

The container 1 shown in FIG. 6 is a portable apparatus configured to hold a single culture vessel 2. The container 1 therefore comprises a single thermally insulated compartment 3 sized to accommodate snugly one culture vessel. Within the thermally insulated compartment 3 is provided a flexible chemical heater 4 which wraps around the culture vessel within the thermally insulated compartment 3. The chemical heater is activated manually either shortly before, or shortly after, placing the culture vessel 2 within the thermally insulated compartment 3. The apparatus is further provided with an agitator, which is not shown in FIG. 1. The agitator might have a similar arrangement to that described below in relation to FIG. 4, for example. The agitator could be within the container 1 to move the vessel 2 within the container 1. Or it could be fitted outside the container 1 to move the whole container and thereby also move the vessel 2 with the container 1.

The container 1 is sealed with a lid 5 which may comprise a sealing O-ring 19 (as shown in FIG. 9).

The exterior of the container may include a label (not shown) on which can be written the time at which the sample began pre-culturing (i.e., the time at which the heater was activated).

The container shown in FIG. 6 has a simple construction, which has the advantage that the container is robust and cheap to manufacture. On the other hand, it may be difficult to accurately maintain the culture vessel at a fixed temperature for a long period of time using this arrangement.

To address this, instead of the chemical heater of FIG. 6, a controllable electrical heater such as a resistance heater 11 (as shown in FIG. 7) may be used. Such a heater 11 may be used in the container 1 of FIG. 6 with appropriate modifications to the container 1. It may also be used in a container 1 as shown in FIGS. 8a-9, as discussed in more detail below. The resistance heater 11 is in communication with a controller 12, which controls the output of the heater responsive to information from a temperature sensor 13 which measures the temperature within the thermally insulated compartment 3.

The controller may also set running a timer 14 when the heater is activated. The time recorded on the timer may be displayed on an LCD display 15 mounted on an external surface of the container 1. The controller is also operable to control an agitator 16. The agitator 16 shakes the culture vessel continuously in order to aerate the sample. The agitator 16 device is controlled by the controller. The agitation may be recorded by an accelerometer 20 to measure the degree of agitation during transportation. The degree of agitation recorded by the accelerometer timer is displayed on the LCD display 15. Each of the resistance heater 11, controller 12, temperature sensor 13, timer 14, LCD display 15, agitator 16 and accelerometer 20 may be powered by a power supply unit (PSU) 17 (not shown on FIG. 7, but shown on FIG. 9). The PSU may for example be a battery pack, which may be rechargeable, and/or readily replaceable.

FIGS. 8a and 8b show details of the base of a portable apparatus including the lower part of a thermally insulated compartment 3. As shown in FIG. 8a, the compartment may have a double-walled structure comprising an inner aluminum shell 3a, to which is bonded a kapton resistance heater 11, and an outer plastic shell 3b. The compartment 3 may be sealed with a lid (not shown) attached to the main body of the compartment with a twist-lock connection 6. The lid might be similar to that shown in FIG. 9. The outer plastic shell 3b may comprise two diametrically opposed holes 7 that receive corresponding pins provided in the container (not shown). The pins and holes 7 perform the dual function of providing an electrical connection through to the kapton resistance heater 11, and also provide a pivotal axis about which the compartment 3 can be rotated in order to agitate the sample in the culture vessel 2. In this way the thermally insulated compartment 3 can be moved using mechanical means to hence mechanically agitate the contents of the culture vessel 2 within the compartment 3. Alternatively, the apparatus of FIGS. 8a and 8b could be adapted so as to include an internal agitator 16 as described with reference to FIG. 9.

FIG. 9 shows a cross-section of another example of a container 1 showing the details of a possible agitation mechanism. Again, the container is a portable apparatus with a thermally insulated compartment 3 for holding a culture vessel 2. The container 1 of FIG. 6 can include a resistance heater 11 as shown in FIG. 8a. The heater 11 together with the agitator 16 can be controlled as described above with reference to FIG. 7.

The agitator 16 comprises a motor 16a, a rotating wheel 16b, a sleeve 16c which receives the culture vessel 2, an off-center coupling engagement 16d between the sleeve 16c and the rotating wheel 16b, and a lock ring 16e which attaches the sleeve 16c to the compartment 3 approximately half way along the length of the culture vessel 2. As the motor 16a rotates, the rotating wheel 16b is also driven to rotate, and correspondingly rotates the culture vessel 2 via the connection of the coupling engagement 16d to the sleeve 16c which holds the culture vessel 2. The connection of the sleeve 16c to the rotating wheel 16b is such that the axis of symmetry of the culture vessel 2 is misaligned with the axis of rotation of the motor 16a and cam wheel 16b, and the two axes are non-parallel, such that the culture vessel 2 rotates in an off-axial manner, fixed in place at the lock ring 16e. In this example this axial misalignment is achieved by the use of a coupling arrangement 16d having a key that cannot be fully fitted within the corresponding recess, such that the key forces the base of the sleeve 16c at one side to be spaced apart from the surface of the rotating wheel 16b, whilst the base of the flask can be closer to or indeed touching the rotating wheel 16b on the other side. This means that the base of the sleeve 16c, and hence the base of the vessel 2, is not parallel with the radial direction of the wheel 16b and therefore the axis of rotational symmetry of the vessel 2 is not parallel with the axis of rotation of the wheel 16b.

The agitator 16 thus agitates the culture vessel 2 by movement of the sleeve 16c when the motor 16c rotates the wheel 16b. The sleeve 16c fits closely to the culture vessel 2, which is a vessel 2 of standardized size and hence known dimensions. The sleeve 16c has flexible tine portions at its open end that are arranged to resiliently deform during insertion and removal of the culture vessel 2. As shown in FIG. 9 these tines hold the vessel 2 securely by gripping the shoulder of the vessel 2 once it is fully inserted in the sleeve 16c.

The motor 16a is powered by a battery pack 17, which is accessed (for replacement or re-charging) via a bottom lid 18. The agitator 16 is controlled by a controller 12, which in this example is a PCB. The motor 16a is advantageously contained within the thermally insulated volume of the thermally insulated compartment 3 such that waste heat from the motor 16a can contribute to heating of the clinical sample in the culture vessel 2.

The thermally insulated compartment 3 comprises thermally insulating material (not shown in all Figures) about the container and with a thickness sufficient to allow the heater to maintain the required temperature. The nature of the thermal insulation can be varied, provided that it provides the necessary reduction in heat loss. Silica aerogel, expanded polyurethane, expanded polystyrene or urea foam may be used, for example.

Optionally the portable apparatus can include a sensor for determining if the sample is positive, as well as an indicator for showing if the sample is positive or not. The indicator may be a light or some other form of display, such as an LCD display. One possibility is to use an optical sensor such as a photodetector (as used, for example, in EP 2828398) to identify changes in the turbidity of the sample. The optical sensor can be mounted within the sleeve around the culture vessel in the example of FIG. 4 in order to ensure an accurate and repeatable reading of the turbidity of the sample even as the sample is agitated. Another possibility is the use of a pH sensor located within the culture vessel. This might be coupled to the controller by a wired or wireless connection to communicate power and/or data in order to allow an indicator on the apparatus to display information relating to the pH within the flask.

The proposed methods and devices described herein allow for pre-culturing of a clinical sample whilst it is in transport. This provides clear advantages in relation to the total time for processing of a sample. FIG. 10 is a box-whisker diagram showing typical times for transport of samples from a patient to a diagnostic system. In prior art systems without pre-culturing, where the sample is essentially inert during transport this time is wasted. Although devices for pre-culturing have been proposed for some purposes, for example as in US 2013/226032, such devices do not provide the agitation required for best performance of the pre-culturing stage.

In medical diagnostics the time to result is often communicated as the time from which a sample is put into a system to time lab result is obtained. For the patient the key issue is of course time to answer from when the clinical sample is taken from the patient to when a lab result is obtained, communicated to treating MD and action taken. The proposed methods and devices provide a way to reduce "time-to-action" for a microbiology in vitro diagnostic system, measured from the time that clinical sample taken until the time that action can be taken to treat the patient.

As an example, for patients with suspected sepsis then blood cultures should always be taken. In the prior art these are transported to the microbiology lab, either at the hospital that the patient is admitted to or to the closest laboratory with microbiology facilities. The time to corrective treatment is very important and it has been shown that mortality increases 7% per hour if not proper treatment is administered. Identifying the causative organism by blood culture enables more focused antibiotics to be used, reducing complications and the risk of emerging antibiotic resistance. Each hour of delay in antibiotic administration increases the risk of death—delay also leads to longer hospital stays and thus greater cost.

The plots of FIG. 10 show the results of analysis of the time to transport a patient sample to the laboratory. This reveals a surprisingly long transportation time, on average in excess of 12 hours. The ability to provide effective culturing during transportation drastically decreases the time to an actionable result. The box-whisker diagram of 500 samples collected at a medium-large sized hospital in Europe. In the box-whisker diagram 50% of the samples fall within the box, the median is shown in the box and the whiskers show minimum and maximum values within each category.

From this data it is evident that the provision of culturing during transportation is hugely beneficial both for samples transported within a hospital as well as between hospitals (hub) for systems that normally require pre-culturing. Examples of such systems are as described in WO2015/189390 as well as other systems today relying on so called positive blood culture flasks and such as e.g., Nanosphere Verigen™ (Nanosphere Inc.), Biofire BCID™ (Biomerieux), and AST/ID from Accelerate Diagnostics as described in e.g., US20150225762. The proposed methods and devices will also shorten time to so called positivity also in so called blood culture cabinets such as e.g., Biomerieux BacTec™, Becton Dickinson BactAlert™ and Thermo Fisher Versa-Trek™ (and similar) as long as the bacterial growth is detected using an absolute measurement and not delta growth after insertion in the system. On average a 5 hour reduction in the time to answer can be achieved within a hospital and a 16 hour reduction in time to answer is possible if samples are shipped between hospitals for systems relying on positive blood culture flasks.

An important aspect for a solution to contribute to faster time-to-action is to streamline workflow. Therefore, deposition of the sampled blood culture flasks from the patient at the site of routine transportation to the microbiology lab is crucial. To ensure pre-culturing the incubator then must be transportable and should be capable of both heating and agitating the clinical sample during transport.

As shown in the examples of FIGS. 11a to 11c it is clear that transportation at room temperature is considerably less effective for stimulation of pathogen growth than transportation at elevated temperature. Three samples with different bacteria were split and allowed to grow in growth media either at room temperature or at 35° C. to simulate transportation at the different conditions. Each hour the amount of bacteria present in the sample were measured using Ocelloscope™ (Philips, Netherlands) and the Biomass was determined based on images acquired from the Ocelloscope. For the *E. coli* 1E4 CFU/ml were used as a starting sample, for *S. aureus* 2.7E3 CFU/ml and for *C. Albicans* 3.6E2 CFU/ml as determined by viable count on non-selective agar plates. *E. coli* is a gram negative, *S. aureus* is a gram positive bacteria and *C. albicans* is a fungi. FIGS. 6a-6c show the growth of bacteria at room temperature (triangular data points) as compared to the growth of bacteria at 35° C. (circular data points) for (a) *E. coli*, (b) *S aureus* and (c) *C. albicans*. There are clear benefits in terms of pre-culturing in the context of diagnostic testing where pre-culturing is needed.

EXAMPLES

Example 1—Blood Culture and Microbial Identification and Characterization by Molecular Tests Blood spiked with 500 μl of *E. coli* bacterial suspension to give a concentration of $10^3$ CFU/ml was added to a BacT/ALERT™ FA plus (Biomerieux) blood culture flask with a needle through the septa. For pre-culture we used an own designed Multirotator from Grant Instruments (Grant-bio PTR-35™) re-designed to blood culture flask (BCF) agitators. Samples were incubated for 4 hours at 35° C.

5 ml of the sample was aspirated, equivalent to 1 ml of whole blood, using a syringe.

Enrichment of bacterial DNA was carried out by the method from Molzym (Germany) without the need for centrifugation.

Preparation of lysis buffer by addition of 800 μl ES to 160 μl MolDNase. Mix by pipetting 6× and add all of the MolDNase solution to 12800 μl lysis buffer followed by mix by pipetting 6×.

Preparation of Proteinase K. Add 1000 μl ES to 400 μl Proteinase K and mix by pipetting 6×.

Lysis

Add 5 ml sample withdrawn from the BCF to 4300 μl Lysis-MolDNase buffer and mix by pipetting 8×. Incubate at 45° C. for 10 min.

Inactivating MolDNase and add 350 μl Proteinase K to the lysate and mix by pipetting 8×. Incubate at 45° C. for 10 min.

Sample Capture to Column and Wash, 3 Loops

Add 605 μl lysate to a filter column (Molzym, Germany), apply 15 seconds vacuum. Add 500 μl RS to the filter column and apply 15 seconds vacuum. Add 605 μl lysate to a filter column (Molzym, Germany), apply 30 seconds vacuum. Add 500 μl RS to the filter column and apply 15 seconds vacuum. Add 605 μl lysate to a filter column (Molzym, Germany), apply 45 seconds vacuum. Add 500 μl RS to the filter column and apply 15 seconds vacuum. Continue with 45 seconds vacuum after sample addition until all sample have been added. More than one filter may be used in order to filter the lysate, if required, if the filter becomes clogged during filtration.

Preparation of Lysis Buffer for Microbes

Add 5.6 μl β-mercaptoethanol to 600 μl RL and mix by pipetting 6×. Add all pre-mixed BM-RL to 80 μl BugLysis and mix by pipetting 6×.

Lysis of Microbes

Add 170 μl of the prepared lysis mixture to the column and apply vacuum for 200 ms. Incubate at 45° C. for 10 min. Add 280 μl prepared Proteinase K-solution to 520 μl Buffer RP. Mix by pipetting 6×. Add 200 μl PK-RP to column. Apply vacuum for 200 ms. Incubate at 45° C. for 10 min.

Binding of Microbial DNA to Column

Move column to room tempered block. Wait for 2 minutes. Add 500 μl CSAB to column. Apply vacuum for 2 s.

Wash 1

Add 500 μl WB to column. Apply vacuum for 2 s.

Wash 2

Add 500 μl WS to column. Apply vacuum for 2 s.

Drying of Membrane

Apply vacuum for 10 min.

Elution

Add 200 μl ET to column.

Apply vacuum for 200 ms.

Incubate at RT for at least 5 min.

Apply vacuum for 1 min.

Repeat once to make two elutions.

The molecular test was carried out on the enriched bacterial DNA sample by the method in Göransson et al, 2012 (supra). During the process of molecular identification of the bacteria the remaining blood sample was kept under agitators.

Padlock probes and target capture probes were ordered from Integrated DNA Technologies (Munich, Germany). The probes were designed to detect unique motifs in each bacteria, selected via bioinformatics tools. The hybridization of capture probes and ligation of padlock probes to the target DNA were performed simultaneously, and was achieved by incubating fragmented and denatured genomic DNA in 20 mM Tris-HCl (pH 8.3), 25 mM KCl, 10 mM MgCl2, 0.5 mM NAD, 0.01% Triton® X-100, 100 nM padlock probe, 50 nM capture probe, 0.2 μg/μl BSA (New England Biolabs, MA, USA), and 250 mU/μl Ampligase™ (Epicentre Biotechnologies, WI, USA) at 55° C. for 5 min. The target DNA along with reacted padlock probes were captured onto magnetic particles via the biotinylated capture probes. This was achieved by adding 50 μg Dynabeads MyOne™ Streptavidin T1 beads (Invitrogen) to the hybridization/ligation reaction and incubating the sample at room temperature for 3 min. Excess probes were eliminated by washing once with 100 μl washing buffer containing 5 mM Tris-HCl (pH 7.5), 5 mM EDTA, 1 M NaCl, and 0.1% Tween-20. The elimination of excess linear padlock probes is performed, since these may otherwise interfere negatively with the subsequent RCA reaction.

Reacted probes were amplified by C2CA, which includes serial enzymatic reactions starting with RCA. The RCA reaction was initiated by the addition of 20 μl ligation mixture containing 1×phi29 DNA polymerase buffer (Fer-mentas, Lithuania; 33 mM Tris-acetate (pH 7.9 at 37° C.), 10 mM Mg-acetate, 66 mM K-acetate, 0.1% (v/v) Tween-20, 1 mM DTT), 100 µM dNTPs, 0.2 µg/µl BSA, 25 nM primer, and 100 mU/µl phi29 DNA polymerase. The reaction was incubated at 37° C. for 11 min, and inactivated at 65° C. for 1 min. The RCA products were digested at 37° C. for 1 min by the addition of 3 units of AluI™ (New England Biolabs), 600 nM replication oligonucleotide, 0.2 µg/µl BSA in 1×phi29 DNA polymerase buffer, and the reaction was terminated at 65° C. for 1 min. Ligation, amplification and labelling reactions were performed by the addition of a mixture containing 1.36 mM ATP, 100 µM dNTPs, 0.2 µg/µl BSA, 28 mU/µl T4 DNA ligase and 120 mU/µl phi29 DNA polymerase in 1×phi29 DNA polymerase buffer to a final volume of 50 µl. The reactions were incubated at 37° C. for 7 min, and terminated at 65° C. for 1 min. The above was repeated once. After the final RCA the products were digested once again into monomers. The RCPs were now ready for analysis.

The digested sample was transferred to a microarray, incubated at 55° C. for 30 minutes followed by a wash with 1×SSC in RT. The hybridized RCA monomers is then labelled via hybridization of a detector oligo at 10 nM concentration in 2×SSC at 55° C. for 30 minutes, washed twice in 1×SSC at RT and spun dry.

The array was then scanned in an array scanner and the result analyzed using array image analysis software as follows.

The array image is evaluated in order to detect spots corresponding to one or several pathogens. A lit spot corresponds to a detected pathogen, with a redundancy of three spots per pathogen. Further, the array has reference spots used for image alignment, which are always lit, and protocol reference spots which—if lit—verify that the individual steps of the molecular protocol succeeded. The analysis is divided into the following steps:

1. The reference spots are detected and the image is aligned accordingly.
2. The spot intensities and backgrounds are measured and the background corrected values are calculated.
3. The measured intensities are compensated for pathogen specific background, such as e.g., unspecific binding of DNA from probe sets corresponding to other pathogens.
4. The array intensity data is used to provide an answer on pathogen id(s) and a quality value.
   a. The algorithm takes the intensity value of all replicate spots corresponding to a specific pathogen into account when calculating the ID answer.
   b. The ID answer may be qualitative (reporting presence of pathogen), and/or quantitative (reporting an indication of the amount of pathogen present in the sample).
   c. The protocol reference spots are evaluated in order to verify that the molecular protocol succeeded.
5. The result is collected and may be transferred to downstream AST analysis and/or reported out in a result report. The result includes:
   a. The ID of the detected pathogen(s).
   b. Semi quantitative values for each detected pathogen.
   c. A quality value indicating the success rate of the molecular protocol.

A sample array image is shown in FIG. 1A. The five spots along the edges of the plate are reference spots and are used for image alignment. Brighter spots indicate a detected pathogen (E. coli). FIG. 1B shows that a fluorescent signal was specifically generated for E. coli.

Example 2—AST Testing on the Blood Culture of Example 1

5 ml from the remaining sample in the blood culture bottle, that had continued to be under culture conditions during the molecular typing, was drawn from the flask.

The drawn sample was enriched for bacteria and at the same time the culture media was changed, in this case to Mueller-Hinton media (MH-media). E. coli bacteria were recovered via filtration through a 0.2 µm filter and then the recovered bacteria were resuspended in MH-media. 63 µl aliquots of the bacterial suspension were transferred to selected wells in a microtiterplate.

Each well had a different concentration of antibiotics as well as different antibiotics. As the microorganism identified in Example 1 was E. coli in this case, the following antibiotics were selected for use in antimicrobial susceptibility testing: Ciprofloxacin, Piperacillin+Tazobactam, Cefotaxime, Ceftazidim, Meropenem and Gentamicin. A series of six different concentrations was prepared for each antibiotic based on known clinical MIC values. A seventh well containing MH broth and no antibiotic was used as a positive control. The microtiterplate was incubated at 35° C. for 4 hours before the plate was read. 7 µl 10 µM Vybrant® DyeCycle™ Orange stain (Molecular Probes® Life Technologies) was added to each well and incubated for 30 min at 37° C. Each microtiterplate well was imaged and the number of bacteria were counted. The differential growth relative to the positive control was used to determine a MIC value for the bacteria. The result for Ciprofloxacin is shown in FIG. 2.

Example 3—Determination of AST Profiles Using Counting of Individual Bacteria in a Flow Cytometry Type Instrument (Aquila 400, Q-Linea AB, Sweden)

Bacteria were grown in blood culture as described in Example 1. 5 ml from the remaining sample in the blood culture bottle, that had continued to be under culture conditions during the molecular typing, was drawn from the flask.

The sample was enriched for bacteria and at the same time the culture media was changed, in this case to Mueller-Hinton media (MH-media). E. coli bacteria were recovered via filtration through a 0.2 µm filter and the recovered bacteria were resuspended in MH-media to a concentration of approximately $10^8$ CFU/ml in Müller Hinton broth before being diluted to approximately $10^6$ CFU/ml in Müller Hinton Broth.

Antibiotic solutions were prepared in a series of 2:1 serial dilutions in Müller Hinton broth at 10× test concentrations. The range of antibiotic concentrations was chosen based on identity of the bacteria and the antibiotic. As the microorganism identified in Example 1 was E. coli in this case the following antibiotics were selected for use in the antimicrobial susceptibility test: Ciprofloxacin, Piperacillin+Tazobactam, Cefotaxime, Ceftazidim, Meropenem and Gentamicin. A series of eight different concentrations was selected based on known clinical MIC values. Eight sample tubes containing 100 µl antibiotic solution at eight different concentrations and 800 µl Müller Hinton broth were prepared. One additional tube contains 900 µl Müller Hinton broth and no antibiotic as positive control. 100 µl bacterial suspension ($10^6$ CFU/ml) was added to all nine tubes. A negative control sample comprising 1000 µl Müller Hinton broth (i.e., no bacteria) is prepared as negative control.

All tubes were incubated at 35° C. and samples were taken after 0, 4, 6 and 24 hours. Bacterial samples were prepared for counting as in Example 2. Bacterial AST profiles were determined using a flow cytometry based counting of individual bacteria in an Aquila 400™ instrument (Q-linea AB, Sweden). Aquila 400 analysis was performed using the alexa 488™ laser.

It was evident from the analysis performed at different time points that 4 hours was sufficient for detecting differential bacterial growth at the different concentration of antibiotics and thus to determine antibiotic susceptibility. Shorter times have been shown in the literature so this is not unexpected. Differential bacterial growth relative to the positive control sample for each antibiotic is shown in FIG. 3. MIC values for each antibiotic at different time points and cut-off values were calculated based on the differential bacterial growth. Values obtained by this method compared favorably with previously reported clinical MIC values and are shown below. The results show excellent precision and sensitivity obtained by counting individual bacteria instead of averaging measurements.

Cefotaxime

MIC with Macrobroth dilution is 0.125 µg/ml and another lab has determined MIC with E-test to ≤0.5 µg/ml.

|  | Cut-off | | |
|---|---|---|---|
|  | 4 hours | 6 hours | 24 hours |
| 5% | — | 0.06 | 0.125 |
| 10% | — | 0.06 | 0.125 |
| 15% | 0.06 | 0.03 | 0.06 |
| 20% | 0.06 | 0.03 | 0.06 |

Ciprofloxacin

MIC with Macrobroth dilution is 0.016 µg/ml and another lab has determined MIC with E-test to ≤0.03 µg/ml.

|  | Cut-off | | |
|---|---|---|---|
|  | 4 hours | 6 hours | 24 hours |
| 5% | 0.016 | 0.008 | 0.008 |
| 10% | 0.008 | 0.008 | 0.008 |
| 15% | 0.008 | 0.008 | 0.008 |
| 20% | 0.008 | 0.004 | 0.008 |

Gentamicin

MIC with Macrobroth dilution is 0.5-1 µg/ml and another lab has determined MIC with E-test to 1 µg/ml.

|  | Cut-off | | |
|---|---|---|---|
|  | 4 hours | 6 hours | 24 hours |
| 5% | 1 | 0.5 | 1 |
| 10% | 0.5 | 0.5 | 1 |
| 15% | 0.5 | 0.5 | 1 |
| 20% | 0.5 | 0.5 | 1 |

Meropenem

MIC with Macrobroth dilution is 0.25-0.5 µg/ml and another lab has determined MIC with E-test to ≤0.25 µg/ml. MIC estimated with Macrobroth dilution and with Aquila 400 is too high because old stock of antibiotics was used.

|  | Cut-off | | |
|---|---|---|---|
|  | 4 hours | 6 hours | 24 hours |
| 5% | — | — | 0.5 |
| 10% | — | — | 0.5 |
| 15% | — | 0.5 | 0.25 |
| 20% | 0.5 | 0.25 | 0.125 |

Ceftazidime

MIC with Macrobroth dilution is 0.25 µg/ml and another lab has determined MIC with E-test to ≤0.5 µg/ml.

|  | Cut-off | | |
|---|---|---|---|
|  | 4 hours | 6 hours | 24 hours |
| 5% | 0.25 | 0.125 | 0.25 |
| 10% | 0.25 | 0.125 | 0.25 |
| 15% | 0.125 | 0.125 | 0.25 |
| 20% | 0.125 | 0.125 | 0.25 |

Piperacillin and Tazobactam

MIC with Macrobroth dilution is 4-8 µg/ml and another lab has determined MIC with E-test to 2 µg/ml.

|  | Cut-off | | |
|---|---|---|---|
|  | 4 hours | 6 hours | 24 hours |
| 5% | 4 | 4 | 4 |
| 10% | 4 | 4 | 4 |
| 15% | 4 | 4 | 4 |
| 20% | 4 | 2 | 2 |

Example 4—Method with AST Determination by AST Using Padlock Probes and C2CA Amplification Blood cultures spiked with *E. coli* were set up and molecular typing was performed as described in Example 1. 5 ml from the remaining sample in the blood culture bottle, that had continued to be under culture conditions during the molecular typing, was drawn from the flask and the sample was enriched for bacteria and changed into MH-media as in Example 2.

63 µl aliquots were transferred to selected wells in a microtiterplate. Each well had a different concentration of antibiotics as well as different antibiotics. In one microtiterplate 12 different antibiotics had been placed, each at four different concentrations and one blank, i.e., no antibiotics. After 4 hours growth in the microtiterplate each well were subjected to bacterial lysis to release the bacterial DNA.

Antibiotic susceptibility testing was performed using Amplified Single Molecule Detection (ASMD) where the DNA from pathogens is extracted followed by digital counting of amplification products, rather than by direct labelling of bacteria. The molecular detection test was carried out on the bacterial DNA sample by the method in Göransson et al, 2012.

Padlock probes and target capture probes were ordered from Integrated DNA Technologies (Munich, Germany).

The probes were designed to detect unique motifs in each bacteria, selected via bioinformatics tools. the hybridization of capture probes and ligation of padlock probes to the target DNA were performed simultaneously, and was achieved by incubating fragmented and denatured genomic DNA in 20 mM Tris-HCl (pH 8.3), 25 mM KCl, 10 mM MgCl2, 0.5 mM NAD, 0.01% Triton® X-100, 100 nM padlock probe, 50 nM capture probe, 0.2 µg/µl BSA (New England Biolabs, MA, USA), and 250 mU/µl Ampligase™ (Epicentre Bio-technologies, WI, USA) at 55° C. for 5 min. The target DNA along with reacted padlock probes were captured onto magnetic particles via the biotinylated capture probes. This was achieved by adding 50 µg Dynabeads MyOne™ Streptavidin T1 beads (Invitrogen) to the hybridization/ ligation reaction and incubating the sample at room tem-perature for 3 min. Excess probes were eliminated by washing once with 100 µl washing buffer containing 5 mM Tris-HCl (pH 7.5), 5 mM EDTA, 1 M NaCl, and 0.1% Tween-20. The elimination of excess linear padlock probes is necessary, since these would otherwise interfere nega-tively with the subsequent RCA reaction.

Reacted probes were amplified by C2CA, which includes serial enzymatic reactions starting with RCA. The RCA reaction was initiated by the addition of 20 µl ligation mixture containing 1×phi29 DNA polymerase buffer (Fer-mentas, Lithuania; 33 mM Tris-acetate (pH 7.9 at 37° C.), 10 mM Mg-acetate, 66 mM K-acetate, 0.1% (v/v) Tween-20, 1 mM DTT), 100 µM dNTPs, 0.2 µg/µl BSA, 25 nM primer, and 100 mU/µl phi29 DNA polymerase. The reaction was incubated at 37° C. for 11 min, and inactivated at 65° C. for 1 min. The RCA products were digested at 37° C. for 1 min by the addition of 3 units of AluI™ (New England Biolabs), 600 nM replication oligonucleotide, 0.2 µg/µl BSA in 1×phi29 DNA polymerase buffer, and the reaction was terminated at 65° C. for 1 min. Ligation, amplification and labelling reactions were performed by the addition of a mixture containing 1.36 mM ATP, 100 µM dNTPs, 0.2 µg/µl BSA, 28 mU/µl T4 DNA ligase and 120 mU/µl phi29 DNA polymerase in 1×phi29 DNA polymerase buffer to a final volume of 50 µl. The reactions were incubated at 37° C. for 7 min, and terminated at 65° C. for 1 min. The above was repeated once.

After the last RCA reaction fluorescent labelled oligo-nucleotides complementary to the RCP was added at a concentration of 5 nM each. The reaction was incubated at 65° C. for 2 minutes followed by 5 minutes at 37° C. and allowed to cool down.

The samples were then injected into Aquila 400, (U.S. Patent Application No. 61/979,319) and number of RCP products were recorded as described in Jarvius et al, 2006 (Jarvius J., et al, Nature Methods 3, 725-727 (2006). The number of RCP products detected for the bacterial sample grown at each concentration of Ciprofloxacin and Cefotax-ime is shown in FIG. 4. This data was used to estimate an MIC concentration for each antibiotic.

Example 5—Strategy for Probe Design

Identification of the pathogen can be performed in mul-tiplex. For this each included pathogen has up to three specific capture oligonucleotides used to fish out the target DNA. Each pathogen also has up to three specific padlock probes hybridizing to the target near to the respective capture oligonucleotides. The process for designing ASMD probe sets can be divided into two main steps: finding optimal target regions and designing the probe sequences.

Below is a further breakdown of the design process: Finding genomic targets—Acquire microbial genome sequences from a genome database (e.g., NCBI)—Partition genome sequences into target and background groups. —If more than one target genome, search for sequences common to all. —Apply a set of filters to remove low-complexity candidates (homopolymers, high/low %-GC, repeats, etc.)— Background filtering: candidates with high sequence simi-larity to genomes in background partition are discarded. —Report accepted candidates. Make probes—Load genomic targets to which probes will be designed (selected in the step above)—Choose settings (probe length, melting temperatures, hetero/homodimer filter, ligation filter, etc.)— Find optimal probe sequences. —Present passed candidates and a short design summary.

The probes used for filtering and recognition of genomic DNA targets are made up as shown in FIG. 5. The capture probe brings target fragments onto solid phase, and the padlock then binds to its target, gets ligated into a circle and is amplified in the subsequent C2CA reaction. The padlock has two target-complementary parts (5/3'-arms) and a back-bone with sites for detection (generic), restriction digestion and priming (generic), and array oligo hybridization (unique). The backbone parts are referred to as DO, RO, and AO in FIG. 5. The capture oligo consists of a target complementary part, a CT-linker and a biotin for attachment to solid phase.

The invention claimed is:

1. A clinical sample testing system comprising:
   a) a portable apparatus for transport and incubation of a clinical sample in a first culture vessel, the apparatus comprising: a sealable container having a thermally insulated compartment for receiving the first culture vessel; and a heater for heating the clinical sample to a temperature suitable for pre-culturing of the clinical sample; and
   b) a microorganism detection device configured to receive said first culture vessel and being arranged for culturing the clinical sample, said microorganism detection device comprising:
      optionally a second culture vessel containing a culture medium;
      optionally a portion removal device for removing a portion of the contents of the first culture vessel and transferring the portion to the second culture vessel;
      wherein the second culture vessel is arranged to receive the portion of the contents of the first culture vessel, and is arranged to culture the portion;
      the microorganism detection device comprising:
      a test aliquot extraction device for removing a portion of the contents of the first and/or second culture vessel for use as a test aliquot; and
      one or both of:
      i. a DNA testing device for separating DNA from said test aliquot, and performing nucleic acid tests on said DNA to identify the microorganism and to detect the presence or absence of one or more genetic antimicro-bial resistance markers in said microorganism; and
      ii. an antimicrobial susceptibility test device for per-forming an antimicrobial susceptibility test on said clinical sample and/or portion by monitoring microbial growth by assessing growth or markers for growth;
      wherein the microorganism detection device is configured to continue culturing the clinical sample and/or portion after extraction of the test aliquot.

2. The clinical sample testing system of claim 1, wherein the microorganism detection device comprises the DNA testing device, and wherein the DNA testing device is arranged to perform the nucleic acid tests using:
   i. one or more nucleic acid probes or primers for microbial identification, a said probe or primer being capable of hybridizing specifically to, or a said primer being capable of selectively amplifying, a nucleotide sequence which is identificatory of a given microorganism; and ii. one or more nucleic acid probes or primers for antimicrobial resistance marker detection, a said probe or primer being capable of hybridizing to, or a said primer being capable of selectively amplifying, a nucleotide sequence representing a genetic antimicrobial resistance marker;

and it is detected whether or not said probes or primers have hybridized to said DNA and/or whether or not said primers have taken part in an amplification reaction.

3. The clinical sample testing system of claim 1, comprising:

the DNA testing device and the antimicrobial susceptibility device, wherein the DNA testing device is arranged to perform the nucleic acid tests using:

i. one or more nucleic acid probes or primers for microbial identification, a said probe or primer being capable of hybridizing specifically to, or a said primer being capable of selectively amplifying, a nucleotide sequence which is identificatory of a given microorganism; and ii. one or more nucleic acid probes or primers for antimicrobial resistance marker detection, a said probe or primer being capable of hybridizing to, or a said primer being capable of selectively amplifying, a nucleotide sequence representing a genetic antimicrobial resistance marker;

and it is detected whether or not said probes or primers have hybridized to said DNA and/or whether or not said primers have taken part in an amplification reaction;

wherein the microorganism detection device is configured to continue culturing the clinical sample and/or portion during the nucleic acid tests to produce a cultured clinical sample and/or a cultured portion, respectively, and wherein the microorganism detection device is arranged such that: if the given microorganism is identified by the DNA testing device, then the antimicrobial susceptibility test device is configured to performing the antimicrobial susceptibility test on the cultured clinical sample and/or the cultured portion, and wherein the type and concentration of antimicrobial agents used in said antimicrobial susceptibility test is determined by the identity of the microorganism and antimicrobial resistance markers detected by the DNA testing device.

4. The clinical system sample testing system of claim 1, wherein the test aliquot extraction device is for removing a portion of the contents of the first culture vessel for use as the test aliquot; and wherein the microorganism detection device comprises the DNA testing device and the antimicrobial susceptibility test device, wherein the DNA testing device is arranged to perform the nucleic acid tests using:

i. one or more nucleic acid probes or primers for microbial identification, a said probe or primer being capable of hybridizing specifically to, or a said primer being capable of selectively amplifying, a nucleotide sequence which is identificatory of a given microorganism; and ii. one or more nucleic acid probes or primers for antimicrobial resistance marker detection, a said probe or primer being capable of hybridizing to, or a said primer being capable of selectively amplifying, a nucleotide sequence representing a genetic antimicrobial resistance marker;

and it is detected whether or not said probes or primers have hybridized to said DNA and/or whether or not said primers have taken part in an amplification reaction;

wherein the microorganism detection device is configured to continue culturing the clinical sample during the nucleic acid tests to produce a cultured clinical sample, and wherein the microorganism detection device is arranged such that: if the given microorganism is identified by the DNA testing device, the antimicrobial susceptibility test device is configured to perform the antimicrobial susceptibility test on said cultured clinical sample, and wherein the type and concentration of antimicrobial agents used in said antimicrobial susceptibility test is determined by the identity of the microorganism and antimicrobial resistance markers detected by the DNA testing device.

5. The clinical sample testing system of claim 1, wherein the microorganism detection device comprises:

a second culture vessel containing a culture medium;

a portion removal device for removing a portion of the contents of the first culture vessel and transferring the portion to the second culture vessel;

wherein the second culture vessel is arranged to receive the portion of the contents of the first culture vessel, and is arranged to culture the portion;

wherein the test aliquot extraction device is for removing a portion of the contents of the second culture vessel for use as the test aliquot; and wherein the microorganism detection device further comprises the DNA testing device and the antimicrobial susceptibility test device, wherein the DNA testing device is arranged to perform the nucleic acid tests using:

i. one or more nucleic acid probes or primers for microbial identification, a said probe or primer being capable of hybridizing specifically to, or a said primer being capable of selectively amplifying, a nucleotide sequence which is identificatory of a given microorganism; and ii. one or more nucleic acid probes or primers for antimicrobial resistance marker detection, a said probe or primer being capable of hybridizing to, or a said primer being capable of selectively amplifying, a nucleotide sequence representing a genetic antimicrobial resistance marker;

and it is detected whether or not said probes or primers have hybridized to said DNA and/or whether or not said primers have taken part in an amplification reaction;

wherein the microorganism detection device is configured to continue culturing the clinical sample during the nucleic acid tests to produce a cultured clinical sample, and wherein the microorganism detection device is arranged such that: if the given microorganism is identified by the DNA testing device, the antimicrobial susceptibility test device is configured to perform the antimicrobial susceptibility test on said cultured portion, and wherein the type and concentration of antimicrobial agents used in said antimicrobial susceptibility test is determined by the identity of the microorganism and antimicrobial resistance markers detected by the DNA testing device.

6. The clinical sample processing system of claim 1, wherein the microorganism detection device comprises the DNA testing device and the antimicrobial susceptibility test device, and wherein the microorganism detection device further cultures said clinical sample and/or portion in the first and/or second culture vessel if the given microorganism is not identified by the DNA testing device to enable further microbial identification and antimicrobial susceptibility tests to be performed after additional culturing in order to identify the microorganism and determine its antimicrobial resistance profile.

7. The clinical sample testing system of claim 1, wherein the portable apparatus comprises a controller for controlling the heater to maintain a pre-set temperature and/or for controlling an agitator to apply a predetermined degree of agitation.

8. The clinical sample testing system of claim 1, wherein the portable apparatus comprises a temperature sensor for monitoring the temperature in the compartment.

9. The clinical sample testing system of claim 1, wherein the portable apparatus comprises an agitator for agitating the sample.

10. The clinical sample testing system of claim 9, wherein the portable apparatus comprises an accelerometer for monitoring the agitation of the sample.

11. The clinical sample testing system of claim 8, wherein the agitator comprises an eccentric cam coupled to the first culture vessel and a motor which drives the cam.

12. The clinical sample testing system of claim 9, wherein the agitator provides for mounting of the first culture vessel to a rotation device with an axis of symmetry of the first culture vessel out of alignment with the axis of rotation of the rotation device.

13. The clinical sample testing system of claim 12, wherein the rotation device is a wheel and the apparatus is arranged so that the first culture vessel is held on the wheel for rotation with the wheel, and so that the first culture vessel has its base non-parallel with the radial direction of the wheel.

14. The clinical sample testing system of claim 8, wherein the portable apparatus comprises a sleeve for holding the first culture vessel within the thermally insulated compartment, wherein the sleeve and the first culture vessel are moved by the agitator in order to mechanically agitate the first culture vessel and thereby agitate the sample.

15. The clinical sample testing system of claim 14, wherein the sleeve is arranged to resiliently deform during insertion and removal of the first culture vessel, and to hold the flask securely due to the resilience of the sleeve whilst the first culture vessel is fully inserted.

16. The clinical sample testing system of claim 15, wherein the sleeve comprises resilient tines arranged to clasp a shoulder of the first culture vessel when the first culture vessel is inserted, and to be pushed resiliently outwardly and pass around a circumference of the main body of the first culture vessel when the first culture vessel is being inserted or removed.

17. The clinical sample testing system of claim 1, wherein the clinical sample testing system comprises the first culture vessel and wherein the first culture vessel is a blood culture flask.

18. The clinical sample testing system of claim 1, wherein the portable apparatus comprises a sensor for determining if the sample is positive for microbial growth.

19. The clinical sample testing system of claim 1, wherein the microorganism detection device comprises the DNA testing device, and wherein the DNA testing device is arranged to use hybridization probes.

20. The clinical sample testing system of claim 19, wherein the hybridization probes are padlock probes comprising 5' and 3' ends that can hybridize to an identificatory or antimicrobial resistance marker nucleotide sequence and the DNA testing device is arranged to detect a circularized padlock probe by rolling circle amplification (RCA).

\*　\*　\*　\*　\*